US007270969B2

(12) United States Patent
Watt et al.

(10) Patent No.: US 7,270,969 B2
(45) Date of Patent: *Sep. 18, 2007

(54) METHODS OF CONSTRUCTING AND SCREENING DIVERSE EXPRESSION LIBRARIES

(75) Inventors: Paul Michael Watt, Perth (AU); Wayne Robert Thomas, Perth (AU); Richard Hopkins, North Perth (AU)

(73) Assignee: Phylogica Limited, Crawley (AU)

( * ) Notice: Subject to any disclaimer, the term of this patent is extended or adjusted under 35 U.S.C. 154(b) by 90 days.

This patent is subject to a terminal disclaimer.

(21) Appl. No.: 10/372,003

(22) Filed: Feb. 21, 2003

(65) Prior Publication Data

US 2003/0215846 A1    Nov. 20, 2003

Related U.S. Application Data

(63) Continuation-in-part of application No. 09/568,229, filed on May 5, 2000.

(60) Provisional application No. 60/132,711, filed on May 5, 1999.

(51) Int. Cl.
*C40B 50/06* (2006.01)
*C40B 30/04* (2006.01)

(52) U.S. Cl. .............................. 435/7.37; 435/6; 435/7; 435/7.32; 435/7.33; 435/7.34; 435/7.35; 435/243; 435/DIG. 5; 435/DIG. 7; 435/DIG. 8

(58) Field of Classification Search ................. 436/7.1, 436/6, DIG. 14, DIG. 15, 7.37, 7.32, 7.33, 436/7.35, 243, DIG. 5, DIG. 7, DIG. 8
See application file for complete search history.

(56) References Cited

U.S. PATENT DOCUMENTS

| 5,516,637 | A | 5/1996 | Huang et al. ................... 436/6 |
| 5,763,239 | A | 6/1998 | Short et al. ............. 435/172.1 |
| 5,783,431 | A | 7/1998 | Peterson et al. |
| 5,821,047 | A | 10/1998 | Garrard et al. ................. 435/5 |
| 6,083,715 | A | 7/2000 | Georgiou et al. .......... 435/69.1 |
| 6,174,673 | B1 | 1/2001 | Short et al. ..................... 435/6 |
| 6,190,908 | B1 | 2/2001 | Kang ...................... 435/320.1 |
| 6,238,884 | B1 | 5/2001 | Short et al. |
| 6,297,004 | B1 | 10/2001 | Russell et al. .................. 435/5 |
| 6,316,223 | B1 | 11/2001 | Payan et al. ............... 435/69.1 |
| 6,319,690 | B1 | 11/2001 | Little et al. ................ 435/69.6 |
| 6,361,969 | B1 | 3/2002 | Galeotti ...................... 435/69.1 |
| 6,579,675 | B2 * | 6/2003 | Kamb ........................... 435/6 |
| 6,583,275 | B1 | 6/2003 | Doucette-Stamm et al. |
| 6,720,139 | B1 * | 4/2004 | Zyskind et al. ................. 435/6 |
| 2002/0150906 | A1 | 10/2002 | Debe .............................. 435/6 |

FOREIGN PATENT DOCUMENTS

| WO | WO95/17412 | 6/1995 |
| WO | WO98/16835 | 4/1998 |
| WO | WO99/35282 | 7/1999 |
| WO | WO-2006/017913 A1 | 2/2006 |

OTHER PUBLICATIONS

Amann et al., "ATG vectors'for regulated high-level expression of cloned genes in *Escherichia coli*," Gene (1985), 40:183-190.
Balaban et al., "Autoinducer of virulence as a target for vaccine and therapy against *Staphylococcus aureus*," Science, (1998), 280:438-440.
Baud et al., "Measures of residue density in protein structures," PNAS (1999) 96: 12494-12499.
Berzofsky, Jay A., "Intrinsic and extrinsic factors in protein antigen structure." Science, (1995) 229:932-940.
Blum et al., "Isolation of peptide aptamers that inhibit intracellular processes," PNAS (2000) 97:2241-2246.
Bonaldo et al., "Normalization and subtraction: two approaches to facilitate gene discovery," Genome Research (1996) 6:791-806.
Bremnes et al., "Selection of phage displayed peptides from a random 10-mer library recognising a peptide target," Immunotechnology (1998) 4:21-28.
Britten et al., "Repeated sequence in DNA," Science (1968) 161:529-540.
Burioni et al., "A new subtraction technique for molecular cloning of rare antiviral antibody specificaties from phage display libraries," Res. Virol. (1998) 149:327-330.
Campbell et al., "Solution secondary structure of a bacterially expressed peptide from the receptor binding domain of pseudomonas aeruginosa pill strain pak: a heteronuclear multidimensional nmr study," Biochemistry (1997) 36:12791-12801.
Caponigro et al., "Transdominant genetic analysis of a growth control pathway," PNAS USA, (1998) 95:7508-7513.
Chapman et al., "Recognition of two *Dermatophagoides pteronyssinus*-specific epitopes on antigen $p_1$ by using monoclonal antibodies: binding to each epitope can be inhibited by serum from dust mite-allergic patients," Journal of Immunology (1984) 133: 2488-2495.
Colas et al., "Genetic selection of peptide aptamers that recognize and inhibit cyclin-dependent kinase 2," Nature, (1996) 380:548-550.
Colbere-Garapin et al., "A new dominant hybrid selective marker for higher eukaryotic cells," J. Mol. Biol. (1981) 150:1-14.
De Soultrait et al., "A novel short peptide is a specific inhibitor of the human immunodeficiency virus type 1 integrase," J. Mol. Biol. (2002) 318:45-58.
Dent et al., "The genetics of ivermectin resistance in *Caenorhabditis elegans*," PNAS USA, (2000), 97:2674-2679.
Derossi et al., "The third helix of the antennapedia homeodomain translocates through biological membranes," Journal of Biological Chemistry (1994) 269:10444-10450.

(Continued)

*Primary Examiner*—T. D. Wessendorf
(74) *Attorney, Agent, or Firm*—Morrison & Foerster LLP

(57) ABSTRACT

The present invention provides novel methods for producing nucleic acid fragment libraries that express highly diverse peptides or protein domains and, in particular, methods for producing nucleic acid fragment libraries wherein the nucleic acid fragments of the libraries are derived from two or more diverse characterized genomes.

14 Claims, 11 Drawing Sheets

OTHER PUBLICATIONS

Devereaux et al. "A comprehensive set of sequence analysis programs for the VAX," Nucleic Acids Research (1984) 12: 387-395.
DeVito et al., "An array of target-specific screening strains for antibacterial discovery," Nature Biotechnology (2002) 20:478-483.
Faber et al., "Polyglutamine-mediated dysfunction and apoptotic death of a caenorhabiditis elegans sensory neuron," PNAS USA (1999) 96:179-184.
Fabret et al., "Efficient gene targeted random mutagenesis in genetically stable *Escherichia coli* strains," Nucleic Acids Research (2000) 28: 5 pages.
Fahraeus et al., Inhibition of prb phosphorylation and cell-cycle progression by a 20-residue peptide derived from $p16^{cdkn2/ink4an}$, Current Biology (1996) 6:84-91.
Fehrsen et al., "Cross-reactive epitope mimics in a fragmented-genome phage display library derived from the rickettsia, *Cowdria ruminantium*", Immunotechnology (1999) 4:175-184.
FitzGerald, K., "In vitro display technologies—new tools for drug discovery," DDT (2000) 5:253-258.
Franzoni et al., "Structure of the C-terminal fragment 300-320 of the rat angiotensin II $AT_{1a}$ receptor and its relevance with respect to G-protein coupling," Journal of Biological Chemistry (1997) 272:9734-9741.
Gegg et al., "Probing minimal independent folding units in dihydrofolate reductase by molecular dissection," Protein Science (1997) 6:1885-1892.
Getzoff et al., "Mechanisms of antibody binding to a protein," Science (1987) 235:1191-1196.
Greene et al., "IgE binding structures of the major house dust mite allergen *DER P* I," Molecular Immunology (1992) 29:257-262.
Hengeveld et al., "Functional and structural characterization of a synthetic peptide representing the N-terminal domain of prokaryotic pyruvate dehydrogenase," Biochemistry (2002) 41:7490-7500.
Heymarin et al., "Antigenic and structural analysis of group II allergens (*Der* f II and *Der* p II) from house dust mites (*Dermatophagoides* spp)," J. Allergy Clin. Immunol. (1989) 83:1055-1067.
Hofmann et al., "Rapid retroviral delivery of tetracycline-inducible genes in a single autoregulatory cassette," PNAS USA, (1996) 93:5185-5190.
Hoogenboom et al., "Multi-subunit proteins on the surface of filamentous phage: methodologies for displaying antibody (Fab) heavy and light chains," Nucleic Acids Research (1991) 19:4133-4137.
Horng et al., "Characterization of large peptide fragments derived from the N-terminal domain of the ribosomal protein L9: definition of the minimum folding motif and characterization of local electrostatic interactions," Biochemistry (2002) 41:13360-13369.
Houshmand et al., "Use of bacteriophage T7 displayed peptides for determination of monoclonal antibody specificity and biosensor analysis of the binding reaction," Analytical Biochemistry (1999) 268:363-370.
Humphrey et al., "Chemical synthesis of natural product peptides; coupling methods for the incorporation of noncoded amino acids into peptides," Chem. Rev. (1997) 97:2243-2266.
Irback et al., "Evidence for nonrandom hydrophobicity structures in protein chains," PNAS USA (1996) 93:9533-9538.
Kinzler et al., "Whole genome PCR: application to the identification of sequences bound by gene regulatory proteins," Nucleic Acids Research (1989) 17:3645-3653.
Kolonin et al., "Targeting cyclin-dependent kinases in *Drosophila* with peptide aptamers," PNAS USA (1998) 95:14266-14271.
Koncz et al., "Expression and assembly of functional bacterial luciferase in plants," PNAS USA (1987) 84:131-135.
Kopczynski et al., "A high throughput screen to identify secreted and transmembrane proteins involved in *Drosophila* embryogenesis," PNAS USA (1998) 95: 9973-9978.
Lee et al., "Structure-antigenicity relationship of peptides from the pre-s2 region of the hepatitis B virus surface antigen," Biochemistry and Molecular Biology International (1994) 34:159-168.
Leitner et al., "A mimotope defined by phage display inhibits IgE binding to the plant panallergen profilin," Eur. J. Immunol. (1998) 28:2921-2927.
Lesley et al., "Use of in vitro protein synthesis from polymerase chain reaction-generated templates to study interaction of *Escherichia coli* transcription factors with core RNA polymerase and for epitope mapping of monoclonal antibodies," Journal of Biological Chemistry (1991) 266:2632-2638.
Lind et al., "The binding of mouse hybridoma and human IgE antibodies to the major fecal allergen, *Der p* I, of *Dermatophagoides pteronyssinus*," Journal of Immunology (1988) 140:4256-4262.
Marcello.et al., "Specific inhibition of herpes virus replication by receptor-mediated entry of an antiviral peptide linked to *Escherichia coli* enterotoxin b subunit," PNAS USA (1994) 91:8994-8998.
Marsh et al., "Expanded polyglutamine peptides alone are intrinsically cytotoxic and cause neurodegeneration in *Drosophila*," Human Molecular Genetics (2000) 9:13-25.
McCafferty et al., "Phage antibodies: filamentous phage displaying antibody variable domains," Nature (1990) 348:552-554.
McConnell et al., "Constrained peptide libraries as a tool for finding mimotopes," Gene (1994) 151:115-118.
Mennuni et al., "Identification of a novel type 1 diabetes-specific epitope by screening phage libraries with sera from pre-diabetic patients," J. Mol. Biol. (1997) 268:599-606.
Morris et al., "A peptide carrier for the delivery of biologically active proteins into mammalian cells," Nature Biotechnology (2001) 19:1173-1176.
Morris et al., "Translocating peptides and proteins and their use for gene delivery," Current Opinion in Biotechnology (2000) 11:461-466.
Mulligan et al., "Selection for animal cells that express the *Escherichia coli* gene coding for xanthine-guanine phosphoribosyltransferase," PNAS USA, (1981) 78:2072-2076.
Needleman et al., "A general method applicable to the search for similarities in the amino acid sequence of two proteins," J. Mol. Biol. (1970) 48:443-453.
Neidigh et al., "Designing a 20-residue protein," Nature Structural Biology (2002) 9:425-430.
Ness et al., "Synthetic shuffling expands functional protein diversity by allowing amino acids to recombine independently," Nature Biotechnology (2002) 20:1251-1255.
Norman et al., "Genetic selection of peptide inhibitors of biological pathways," Science (1999) 285:591-595.
O'Hara et al., "Transformation of mouse fibroblasts to methotrexate resistance by a recombinant plasmid expressing a prokaryotic dihydrofolate reductase," PNAS USA (1981) 78:1527-1531.
Patzkill et al., "Mapping protein-ligand interactions using whole genome phage display libraries," Gene (1998) 221:79-83.
Pande et al., "Nonrandomness in protein sequences: evidence for a physically driven stage of evolution?" PNAS USA (1994) 91:12972-12975.
Phelan et al., "Intercellular delivery of functional p53 by the herpesvirus protein VP22," Nature Biotechnology (1998) 16:440-443.
Pincus et al., "Peptides that mimic the group B streptococcal type III capsular polysaccharide antigen," Journal of Immunology (1998) 160:293-298.
Pini et al., "Design and use of a phage display library," Journal of Biological Chemistry (1998) 273:21769-21776.
Read et al., "Finding drug targets in microbial genomes," DDT (2001) 6:887-892.
Richter et al., "Refolding, purification, and characterization of human recombinant pde4a constructs expressed in *Escherichia coli*," Protein Expression and Purification (2000) 19:375-383.
Robben et al., "Selection and identification of dense granule antigen GRA3 by *Toxoplasma gondii* whole genome phage display," Journal of Biological Chemistry (2002) 277:17544-17547.
Roberts et al., "RNA-peptide fusions for the in vitro selection of peptides and proteins," PNAS USA, (1997) 94:12297-12302.
Rogers et al., "Behavioral and functional analysis of mouse phenotype: SHIRPA, a proposed protocol for comprehensive phenotype assessment," (1997) Mammalian Genome (1997) 8:711-713.

Sali et al., "Comparative protein modeling by satisfaction of spatial restrains," J. Mol. Biol. (1993) 234:779-815.

Santerre et al., "Expression of prokaryotic genes for hygromycin B and G418 resistance as dominant-selection markers in mouse L cells," Gene (1984) 30:147-156.

Satyal et al., "Polyglutamine aggregates alter protein folding homeostasis in *Caenorhabditis elegans*," PNAS (2000) 97:5750-5755.

Shafikhani et al., "Generation of large libraries of random mutants in *Bacillus subtilis* by PCR-based plasmid multimerization," BioTechniques (1997) 23:304-310.

Shimatake et al., "Purified λ regulatory protein cII positively activates promoters for lysogenic development," Nature (1981) 292:128-132.

Sleber et al., "Libraries of hybrid proteins from distantly related sequences," Nature Biotechnology (2001) 19:456-460.

Soares, M. B. "Identification and cloning of differentially expressed genes," Current Opinion in Biotechnology (1997) 8:542-546.

Stengelin et al., "Isolation of cDNAs for two distinct human Fc receptors by ligand affinity cloning," The EMBO Journal (1988) 7:1053-1059.

Studier et al., "Use of bacteriophage T7 RNA polymerase to direct selective high-level expression of cloned genes," J. Mol. Biol. (1986) 189:113-310.

Sugita et al., "Combined use of oligonucleotide and tissue microarrays identifies cancer/testis antigens as biomarkers in lung carcinoma," Cancer Research (2002) 62:3971-3979.

Thomas et al., "Expression in *Escherichia coli* of a high-molecular-weight protective surface antigen found in nontypeable and type b *Haemophilus influenzae*," Infection and Immunity (1990), 58:1909-1913.

Tokmakov et al., "Inhibition of MAPK pathway by a synthetic peptide corresponding to the activation segment of MAPK," Biochemical and Biophysical Research Communications (1998) 252:214-219.

Tokmakov et al., "Phosphorylation-sensitive secondary structure in a synthetic peptide corresponding to the activation loop of MAP kinase," Biochemical and Biophysical Research Communication (1997) 236:243-247.

Tripet et al., "Demonstration of coiled-coil interactions within the kinesin neck region using synthetic peptides," Journal of Biological Chemistry (1997) 272:8946-8956.

Van Regenmortel, Marc H.V., "Structural and functional approaches to the study of protein antigenicity," Immunol Today, (1989) pp. 266-272.

Vidal et al., "Yeast forward and reverse 'n'-hybrid systems," Nucleic Acids Research (1999) 27:919-929.

Vranken et al., "Solution structures of a 30-residue amino-terminal domain of the carp granulin-1 protein and its amino-terminally truncated 3-30 subfragment:implications for the conformational stability of the stack of two β-hairpins," Proteins: Structure, Function, and Genetics (2002) 47:14-24.

Wigler et al., "Transformation of mammalian cells with an amplifiable dominant-acting gene," PNAS USA, Genetics (1980) 77:3567-3570.

Wong et al., "Use of tagged random hexamer amplification (TRHA) to clone and sequence minute quantities of DNA-application to a 180 kb plasmid isolated from *Sphingomonas* F199," Nucleic Acids Research (1996) 24:3778-3783.

Xu et al., "Cells that register logical relationships among proteins," PNAS USA (1997) 94:12473-12478.

Xu et al., "Dominant effector genetics in mammalian cells," Nature Genetics (2001) 27:23-29.

Yang et al., "A 20-kilodalton N-terminal fragment of the D15 protein contains a protective epitope(s) against *Haemophilus influenzae* type a and type b," Infection and Immunity (1998) 66:3349-3354.

Yang et al., "An integrated approach to the analysis and modeling of protein sequences and structures. III. A comparative study of sequence conservation in protein structural families using multiple structural alignments," J. Mol. Biol. (2000) 301:691-711.

Yang et al., "Cloning, expression, and characterization of a DNA binding domain of gpNu1, a phage λ DNA packaging protein," Biochemistry (1999) 38:465-477.

Yasueda et al., "Species-specific measurement of the second group of *Dermatophagoides* mite allergens, Der p 2 and Der f 2, using a monoclonal antibody-based ELISA," Clinical and Experimental Allergy, (1996) 26:171-177.

Young, K.H., "Yeast two-hybrid: so many interactions, (in) so little time . . . ," Biology of Reproduction (1998) 58:302-311.

Zhang et al., "Whole genome amplification from a single cell: implications for genetic analysis," PNAS USA (1992) 89:5847-5851.

Arenkov, P. et al. (2000). "Protein Microchips: Use for Immunoassay and Enzymatic Reactions," *Analytical Biochemistry* 278:123-131.

Behrens, A. et al. (Mar. 1999). "Amino-Terminal Phosphorylation of c-Jun Regulates Stress-Induced Apoptosis and Cellular Proliferation," *Nature Genetics* 21:326-329.

Chong et al. (1997). In *The Yeast Two-Hybrid System* Bartel et al. eds. New York, NY pp. 289-297.

Estus, S. et al. (Dec. 1994). "Altered Gene Expression in Neurons During Programmed Cell Death: Identification of c-*Jun* as Necessary for Neuronal Apoptosis," *The Journal of Cell Biology* 127(6):1717-1727.

Fang, Y. et al. (2002). "G-Protein-Coupled Receptor Microarrays," *ChemBioChem* 3:987-991.

Filipe, S.R. (2001). "The Role of *murMN* Operon in Penicillin Resistance and Antibiotic Tolerance of *Streptococcus pneumoniae*," *Microbial Drug Resistance* 7(4):303-316.

Garcia, M. et al. (Mar. 15, 2002). "The Mitochondrial Toxin 3-Nitropropionic Acid Induces Striatal Neurodegeneration via a c-Jun N-Terminal Kinase/c-Jun Module," *The Journal of Neuroscience* 22(6):2174-2184.

Gargala, G. et al. (1999). "Enzyme Immunoassay Detection of *Cryptosporidium parvum* Inhibition by Sinefungin in Sporozoite Infected HCT-8 Enterocytic Cells," *International Journal of Parasitology* 29:703-709.

Hegde, S.S. et al. (Mar. 9, 2001). "FemABX Family Members Are Novel Nonribosomal Peptidyltransferases and Important Pathogen-Specific Drug Targets," *The Journal of Biological Chemistry* 276(10):6998-7003.

Hosen, N. et al. (2004). "Identification of a Gene Element Essential for Leukemia-Specific Expression of Transgenes," *Leukemia* 18:415-419.

Kabouridis, P.S. (Nov. 2003). "Biological Applications of Protein Transduction Technology," *Trends in Biotechnology* 21(11):498-503.

Lambros, C. et al. (Jun. 1979). "Synchronization of Plasmodium Falciparum Erythrocytic Stages in Culture," *J. Parasitol.* 65(3):418-420.

Lee, Y. et al. (2003). "ProtectChip: A Highly Sensitive Protein Microarray Prepared by a Novel Method of Protein Immobilization for Application of Protein-Protein Interaction Studies," *Proteomics* 3:2289-2300.

Maidof, H. et al. (Jun. 1991). "*femA*, Which Encodes a Factor Essential for Expression of Methicillin Resistance, Affects Glycine Content of Peptidoglycan in Methicillin-Resistant and Methicillin-Susceptible *Staphylococcus aureus* Strains," *Journal of Bacteriology* 173(11):3507-3513.

Mazmanian, S.K. et al. (Jul. 30, 1999). "*Staphylococcua aureus* Sortase, an Enzyme that Anchors Surface Proteins to the Cell Wall," *Science* 285:760-763.

Mazmanian, S.K. et al. (May 9, 2000). "*Staphylococcus aureus* Sortase Mutants Defective in the Display of Surface Proteins and in the Pathogenesis of Animal Infections," *Proc. Natl. Acad. Sci. USA* 97(10):5510-5515.

McElveen, J.E. (1998). "Primary Sequence and Molecular Model of the Variable Region of a Mouse Monoclonal Anti-Der p 1 Antibody Showing a Similar Epitope Specificity as Human IgE," *Clinical and Experimental Allergy* 28:1427-1434.

Nedelkov, D. et al. (2001). "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," *Biosensors & Bioelectronics* 16:1071-1078.

Nelson, R.W. et al. (2000). "Biosensor Chip Mass Spectrometry: A Chip-Based Proteomics Approach," *Electrophoresis* 21:1155-1163.

Nemoto, N. et al. (1999). "Fluorescence Labeling of the C-Terminius of Proteins with a Puromycin Analogue in Cell-Free Translation Systems," *FEBS Letters* 462:43-46.

Pavlickova, P. et al. (2003). "Microarray of Recombinant Antibodies Using a Streptavidin Sensor Surface Self-Assembled onto a Gold Layer," *BioTechniques* 34(1):124-130.

Rocco et al. (1998). "Wide-Spectrum Antibodic Activity of Synthetic, Amphiphathic Peptides," *Biochem & Biophys. Res. Comm.* 249:202-206.

Rohrer, S. et al. (Aug. 1999). "The Essential *Staphylococcus aureus* Gene *fmhB* Is Involved in the First Step of Peptidoglycan Pentaglycine Interpeptide Formation," *Proc. Natl. Acad. Sci. USA* 96:9351-9356.

Rosenthal, P.J. et al. (Jul. 1996). "Antimalarial Effects of Vinyl Sulfone Cysteine Proteinase Inhibitors," *Antimicrobial Agents and Chemotherapy* 40(7):1600-1603.

Sambrook et al. (1989). Chapters 12 and 13 *In Molecular Cloning: A Laboratory Manual*, Second Edition, Cold Spring Harbor Laboratory Press, USA.

Stranden, A. M. et al. (Jan. 1997). "Cell Wall Monoglycine Cross-Bridges and Methicillin Hypersusceptibility in a *femAB* Null Mutant of Methicillin-Resistant *Staphylococcus aureus*," *Journal of Bacteriology* 179(1):9-16.

Theiss, H.D. et al. (2003). "Enhancement of Gene Transfer With Recombinant Adeno-Associated Virus (rAAV) Vectors into Primary B-Cell Chronic Lymphocytic Leukemia Cells by CpG-oligodeoxynucleotides," *Experimental Hematology* 31:1223-1229.

Thumm, G. et al. (1997). "Studies on Prolysostaphin Processing and Characterization of the Lysostaphin Immunity Factor (Lif) of *Staphylococcus simulans* Biovar *Staphyloyticus*," *Molecular Microbiology* 23(6):1251-1265.

Davies, J.M. et al. (Jun. 2000). "Use of Phage Display Technology to Investigation Allergen-Antibody Interactions," *J. Allergy Clin. Immunol.* 105(6):1085-1092.

Furmonaviciene, R. et al. (1999). "The Use of Phage-Peptide Libraries to Define the Epitope Specificity of a Mouse Monoclonal Anti-Der p 1 Antibody Representative of a Major Component of the Human Immunoglobulin E Anti-Der p 1 Response," *Clin. Exp. Allergy* 29:1563-1571.

Yao, S.Q. et al. (1997). "Inhibiting Dimerization and DNA Binding of c-Jun," *In Peptides: Frontiers of Peptide Science, Proceedings of the 15th American Peptide Symposium*, Nashville, TN, Jun. 14-19, 1997, Tam, J.P. et al. eds. Kluwer Academic Publishers, Dordrecht, Netherlands, pp. 751-752.

Zhou, X-F. et al. (Feb. 1999). "Ligand-Activated Retinoic Acid Receptor Inhibits AP-1 Transactivation by Disrupting c-Jun/c-Fos Dimerization," *Mol. Endocrin.* 13(2):276-285.

Alekshun, M.N. (Dec. 2001). "Beyond Comparison—Antibiotics From Genome Data?" *Nature Biotechnology* 19:1124-1125.

Amstutz, P. et al. (2001). "In vitro Display Technologies: Novel Development and Applications," *Current Opinion in Biotechnology* 12:400-405.

Angrist, M. (1998). "Less is More: Compact Genomes Pay Dividends," *Genome Research* 8:683-685.

Cordwell, S.J. (1999). "Microbial Genomes and 'Missing' Enzymes: Redefining Biochemical Pathways," *Arch. Microbiol.* 172:269-279.

Erdos, G. et al. (2006). "Construction and Characterization of a Highly Redundant *Pseudonomas aeruginosa* Genomic Library Prepared From 12 Clinical Isolates: Application to Studies of Gene Distribution Among Populations," *Intl. Journal of Pediatric Otorhinolaryngology* 70:1891-1900.

Halstead, J.R. et al. (1999). "A Family 26 Mannanase Produced by *Clostridium thermocellum* as a Component of the Cellulosome Contains a Domain Which is Conserved in Mannanases from Anaerobic Fungi," *Microbiology* 145:3101-3108.

Michiels, F. et al. (2002). "Arrayed Adenoviral Expression Libraries for Functional Screening," *Nature Biotechnology* 20:1154-1157.

Nelson, K.E. et al. (Oct. 2000). "Status of Genome Projects for Nonpathogenic Bacteria and Archaea," *Nature Biotechnology* 18:1049-1054.

Nelson, R.W. et al. (1999). "BIA/MS of Epitope-Tagged Peptides Directly from *E. coli* Lysate: Multiplex Detection and Protein Identification at Low-Femtomole to Subfemtomole Levels," *Anal. Chem.* 71:2858-2865.

Oefner, P.J. et al. (1996). "Efficient Random Subcloning of DNA Sheared in a Recirculating Point-Sink Flow System," *Nucleic Acids Research* 24(20):3879-3886.

Postier, B.L. et al. (2003). "The Construction and Use of Bacterial DNA Microarrays Based on an Optimized Two-Stage PCR Strategy," *BMC Genomics*, vol. 4, 11 pages.

Supplementary Partial European Search Report for EP Application No. 04712970.5 mailed Apr. 26, 2006, five pages.

Supplementary Partial European Search Report for EP Application No. 04712970.5 mailed Aug. 3, 2006, seven pages.

Wittrup, K.D. (2001). "Protein Engineering by Cell-Surface Display," *Current Opinion in Biotechnology* 12:395-399.

Yao, S. et a. (1998). "Uncoiling c-Jun Coiled Coils: Inhibitory Effects of Truncated Fos Peptides on Jun Dimerization and DNA Binding In Vitro," *Biopolymers* 47:277-283.

Zhou, J-M. et al. (2002). "A Novel Strategy by the Action of Ricin That Connects Phenotype and Genotype Without Loss of the Diversity of Libraries," *J. Am. Chem. Soc.* 124(4):538-543.

\* cited by examiner 1  100 bp ladder (NEB), 2-20 BGF PCR products from all 19 bacterial species pDD

METHODS OF CONSTRUCTING AND SCREENING DIVERSE EXPRESSION LIBRARIES

RELATED APPLICATION DATA

The present invention is a continuation-in-part application of U.S. Ser. No. 09/568,229 filed May 5, 2000 which claims the benefit of priority under 35 USC § 119(e) from U.S. Provisional Application No 60/132,711 filed May 5, 1999, both of which are herein incorporated by reference in their entirety.

FIELD OF THE INVENTION

The present invention relates generally to methods for the production and of nucleic acid fragment libraries that express highly diverse peptides, polypeptides or protein domains and, in particular, methods for producing nucleic acid fragment libraries wherein the nucleic acid fragments of the libraries are derived from one and preferably from two or more prokaryote genomes or compact eukaryote genomes, such as, for example, organisms having diverse characterized genomes. In another embodiment, the nucleic acid fragments are expressed as protein domains capable of assuming a conformation that binds to a target protein or nucleic acid during library screening. The present invention further provides methods of screening such libraries to identify peptides, polypeptides or protein domains that bind to a target protein or nucleic acid such as, for example, to modulate the activity of the target protein or nucleic acid. Also provided are methods for identifying nucleic acid encoding such peptides, polypeptides or protein domains. The present invention extends to the nucleic acids, peptides, polypeptides and protein domains identified by the methods described herein.

BACKGROUND OF THE INVENTION

1. General Information

As used herein the term "derived from" shall be taken to indicate that a specified integer is obtained from a particular source albeit not necessarily directly from that source.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Unless specifically stated otherwise, each feature described herein with reference to a particular aspect or embodiment of the invention shall be taken to apply mutatis mutandis to each and every other aspect or embodiment of the invention. For example, any one or more features described herein with respect to methods for expression library construction shall apply to those embodiments relating to methods for screening expression libraries to identify a peptide or protein domain capable of binding a target protein or nucleic acid or nucleic acid encoding same.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein. Functionally equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts:

1. Sambrook, Fritsch & Maniatis, whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactiva, Germany);
10. Sakakibara, D., Teichman, J., Lien, E. Land Fenichel, R. L. (1976). *Biochem. Biophys. Res. Commun.* 73 336-342
11. Merrifield, R. B. (1963). *J. Am. Chem. Soc.* 85, 2149-2154.
12. Barany, G. and Merrifield, R. B. (1979) in *The Peptides* (Gross, E. and Meienhofer, J. eds.), vol. 2, pp. 1-284, Academic Press, New York.
13. Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart.
14. Bodanszky, M. (1984) *Principles of Peptide Synthesis*, Springer-Verlag, Heidelberg.
15. Bodanszky, M. & Bodanszky, A. (1984) *The Practice of Peptide Synthesis*, Springer-Verlag, Heidelberg.
16. Bodanszky, M. (1985) *Int. J. Peptide Protein Res.* 25, 449-474.
17. Handbook of Experimental Immunology, Vols. I-IV (D. M. Weir and C. C. Blackwell, eds., 1986, Blackwell Scientific Publications).
18. McPherson et al., *In: PCR A Practical Approach.*, IRL Press, Oxford University Press, Oxford, United Kingdom, 1991.
19. Methods in Yeast Genetics: A Cold Spring Harbor Laboratory Course Manual (D. Burke et al., eds) Cold Spring Harbor Press, New York, 2000 (see whole of text).

20. Guide to Yeast Genetics and Molecular Biology. In: Methods in Enzymology Series, Vol. 194 (C. Guthrie and G. R. Fink eds) Academic Press, London, 1991 2000 (see whole of text).

2. Description of the Related Art

As a response to the increasing demand for new lead compounds and new target identification and validation reagents, the pharmaceutical industry has increased its screening of various sources for new lead compounds having a unique activity or specificity in therapeutic applications, such as, for example, in the treatment of neoplastic disorders, infection, modulating immunity, autoimmunity, fertility, etc.

It is known that proteins bind to other proteins, antigens, antibodies, nucleic acids, and carbohydrates. Such binding enables the protein to effect changes in a wide variety of biological processes in all living organisms. As a consequence, proteins represent an important source of natural modulators of phenotype. Accordingly, peptides that modulate the binding activity of a protein represent attractive lead compounds (drug candidates) in primary or secondary drug screening. For example, the formation of a target biological interaction that has a deleterious effect (eg. replication of a pathogen or of a cancer cell), can be assayed to identify lead compounds that antagonize the biological interaction.

Similarly, the activity or expression of an antimicrobial target (eg., a protein produced by a particular microbe that is required for its survival or propagation), can be screened for novel compounds that modulate the survival or propagation of the microbe by antagonizing an activity or function of the antimicrobial target. Peptides that block the function of specific membrane channels, or disrupt cytoplasmic membranes of some organisms is represent attractive candidates for anti-microbial drugs. Antimicrobial effects have been demonstrated for certain natural peptides produced by animals and insects, and for synthetic cationic peptides (eg., azurocidin, cathepsin G, Cationic Antimicrobial Peptides CAP57 and CAP37, defensin, bactenecin and magainin).

A virulence determinant of a pathogen also presents an attractive target for identifying lead compounds having antimicrobial activity. For example, a peptide antagonist of an autoinducer of virulence in *Staphylococcus aureus* that controls the production of bacterial toxins involved in pathogenesis has been determined. The antagonist, designated REP (RNAIII inhibiting peptide) is produced by a non-pathogenic strain of *Staphylococcus aureus* and appears to inhibit the RNAIII gene that is induced by a threshold concentration of an endogenous protein, RNA III Activating Protein (RAP), in virulent strains.

In another example, differential gene expression between normal and diseased (eg., neoplastic or apoptotic) cells, such as, for example, differential expression of cellular receptors, and/or differential signal transduction processes between normal and diseased cells, implicate those differential patterns of gene expression in disease. Accordingly, the genes or proteins that are differentially expressed in diseased and normal cells, or the differential cellular processes between normal and diseased cells, form attractive targets for therapy. Similarly, cyclin proteins such as Cdc2, Cdc25, and cyclin-dependent kinases (CDKs) are attractive targets for cellular proliferation. Peptides that agonize or antagonize the expression of such target genes or target processes are suitable lead compounds for therapeutic applications.

In yet another example, certain allergen proteins (eg., DerpI) are attractive targets for screens to identify anti-allergenic compounds that prevent or inhibit immune responses to the allergen protein.

It is widely recognized that there is a need to develop methods for determining novel compounds, including nucleic acid-based products and peptide-based products, that modulate an activity or function of a particular target. In such approaches, an activity of a target protein or nucleic acid is screened in the absence and presence of a potential lead compound, which is a peptide, and modified activity of the target is determined.

Similarly, peptides can be used as dominant negative inhibitors or the validation of prospective drug targets using assays such as observing the phenotype resulting from over-expression of the peptides in ex-vivo assays or in transgenic mice.

In one known approach to identify novel lead compounds, random peptide (synthetic mimetic or mimotope) libraries are produced using short random oligonucleotides produced by synthetic combinatorial chemistry. The DNA sequences are cloned into an appropriate vehicle for expression and the encoded peptide is then screened using one of a variety of approaches. However, the ability to isolate active peptides from random fragment libraries can be highly variable with low affinity interactions occurring between the peptide-binding partners. Moreover, the expressed peptides often show little or none of the secondary or tertiary structure required for efficient binding activity, and/or are unstable. This is not surprising, considering that biological molecules appear to recognise shape and charge rather than primary sequence (Yang and Honig *J. Mol. Biol* 301(3), 691-711 2000) and that such random peptide aptamers are generally too small to comprise a protein domain or to form the secondary structure of a protein domain. The relatively unstructured 'linear' nature of these peptide aptamers also leads to their more rapid degradation and clearance following administration to a subject in vivo, thereby reducing their appeal as therapeutic agents.

To enhance the probability of obtaining useful bioactive peptides or proteins from random peptide libraries, peptides have previously been constrained within scaffold structures, eg., thioredoxin (Trx) loop (Blum et al. *Proc. Natl. Acad. Sci. USA,* 97, 2241-2246, 2000) or catalytically inactive staphylococcal nuclease (Norman et al, *Science,* 285, 591-595, 1999), to enhance their stability. Constraint of peptides within such structures has been shown, in some cases, to enhance the affinity of the interaction between the expressed peptides and its target, presumably by limiting the degrees of conformational freedom of the peptide, and thereby minimizing the entropic cost of binding.

It is also known to tailor peptide expression libraries for identifying specific peptides involved in a particular process, eg., antigen-antibody-binding activity. For example U.S. Pat. No. 6,319,690 (Dade Behring Marburg GmBH) teaches a PCR-based method of amplifying cDNA sequences encoding a population of antibodies, wherein oligonucleotide primers that are homologous to conserved regions of antibody-encoding cDNAs derived from a mixture of non-activated B-lymphocytes are used to amplify nucleic acids that encode antibody variable regions. The amplified sequences are expressed using a bacterial display system, for screening with selected antigens to determine those antibody fragments that bind the antigens. However, the expression libraries described in U.S. Pat. No. 6,319,690 show limited diversity, because the amplified fragments were all antibody-encoding fragments derived from a single complex eukaryote. Additionally, the antibody-encoding libraries described in U.S. Pat. No. 6,319,690 were screened for antigen-binding activity rather than for a novel bioactivity (ie. the expressed peptides were not mimotopes).

Several attempts have been made to develop libraries based on naturally occurring proteins (eg genomic expression libraries). Libraries of up to several thousand polypeptides or peptides have been prepared by gene expression systems and displayed on chemical supports or in biological systems suitable for testing biological activity. For example, genome fragments isolated from *Escherichia coli* MG1655 have been expressed using phage display technology, and the expressed peptides screened to identify peptides that bind to a polyclonal anti-Rec A protein antisera (Palzkill et al. *Gene*, 221 79-83, 1998). Such expression libraries are generally produced using nucleic acid from single genomes, and generally comprise nucleic acid fragments comprising whole genes and/or multiple genes or whole operons, including multiple linked protein domains of proteins. Additionally, as many bacteria comprise recA-encoding genes, the libraries described by Palzkill et al., were screened for an activity that was known for the organism concerned, rather than for a novel bioactivity (ie. the expressed peptides were not necessarily mimotopes).

U.S. Pat. No. 5,763,239 (Diversa Corporation) describes a procedure for producing normalized genomic DNA libraries from uncharacterized environmental samples containing a mixture of uncharacterized genomes. The procedure described by Diversa Corp. comprises melting DNA isolated from an environmental sample, and allowing the DNA to reanneal under stringent conditions. Rare sequences, that are less likely to reanneal to their complementary strand in a short period of time, are isolated as single-stranded nucleic acid and used to generate a gene expression library. However, total normalization of each organism within such uncharacterized samples is difficult to achieve, thereby reducing the biodiversity of the library. Such libraries also tend to be biased toward the frequency with which a particular organism is found in the native environment. As such, the library does not represent the true population of the biodiversity found in a particular biological sample. In cases where the environmental sample includes a dominant organism, there is likely to be a significant species bias that adversely impacts on the sequence diversity of the library. Furthermore, as many of the organisms found in such samples are uncharacterized, very little information is known regarding the constitution of the genomes that comprise such libraries. Accordingly, it is not possible to estimate the true diversity of such libraries. Additionally, since the Diversa Corp. process relies upon PCR using random primers to amplify uncharacterized nucleic acids, there is no possibility of accounting for biasing factors, such as, for example, a disproportionate representation of repeated sequences across genomes of the organisms in the environmental sample.

Accordingly, there remains a need to produce improved methods for constructing highly diverse and well characterized expression libraries wherein the expressed peptides are capable of assuming a secondary structure or conformation sufficient to bind to a target protein or nucleic acid, such as, for example, by virtue of the inserted nucleic acid encoding a protein domain.

SUMMARY OF THE INVENTION

The present invention is based upon the understanding of the present inventors that, in contrast to random synthetic peptide libraries produced by combinatorial approaches, or short random peptides produced by expression of PCR products, amino acids are not randomly distributed in nature (Pande et al., *Proc Natl Acad. Sci. USA* 91 12972-12975, 1994). Proteins that fold well in nature have non-random hydrophobicity distributions (Irback et al., *Proc Natl Acad. Sci. USA* 93, 9533-9538, 1996). In any native peptide, the distribution of amino acid residues according to their chemical properties (eg hydrophobicity, polarity, etc) is also non-random (Baud and Karlin, *Proc Natl Acad. Sci. USA* 96, 12494-12499, 1999). Accordingly, the present inventors realized that random peptide libraries have a low frequency of naturally occurring or native peptide conformational structures or secondary structures, such as, for example, those structures formed by protein domains.

In work leading up to the present invention, the inventors sought to take advantage of diverse and well-characterized prokaryotic genomes and/or compact eukaryotic genomes in the construction of highly diverse expression libraries for isolating bioactive peptides or proteins. In particular, the use of combinations of nucleic acid fragments from one or two or more well characterized genomes has allowed the inventors to control the degree the diversity of peptides/proteins expressed in their expression libraries, to enhance the possibility of isolating novel peptides having the ability to bind to a desired protein or nucleic acid. It will be understood from the disclosure herein that the bioactive peptides or proteins expressed by individual library clones of such libraries are screened for an activity of the encoded peptide, particularly a binding activity, which said encoded protein has not been shown to possess in the context of the protein from which it was derived (ie in its native environment). In the screening process, any library clone encoding a peptide that has the same activity as it would have in its native environment is excluded during the screening process, since an objective of the present invention is to isolate novel bioactive peptides or proteins.

Peptides encoded by genomes which differ from the genome of the drug target organism (eg. humans) are a particularly rich source of high affinity target binding agents. This is because in the evolution of the target organism itself, such high affinity peptide domains have been selected against other than the interaction interfaces which may exist in that organism for functional dimerization with natural partners.

In one embodiment, the libraries described in the present invention are constructed from nucleic acid fragments comprising genomic DNA, cDNA, or amplified nucleic acid derived from one or two or more well-characterized genomes.

Preferably, one or more well-characterized genomes is a compact genome of a eukaryote (ie. protist, dinoflagellate, alga, plant, fungus, mould, invertebrate, vertebrate, etc) such as, for example, a eukaryote selected from the group consisting of *Arabidopsis thaliana, Anopheles gambiae, Caenorhabditis elegans, Danio rerio, Drosophila melanogaster, Takifugu rubripes, Cryptosporidium parvum, Trypanosoma cruzii, Saccharomyces cerevesiae*, and *Schizosaccharomyces pombe*.

In another embodiment, one or more well-characterized genomes is a compact genome of a prokaryote (ie. bacteria, eubacteria, cyanobacteria, etc) such as, for example a prokaryote selected from the group consisting of *Archaeoglobus fulgidis, Aquifex aeolicus, Aeropyrum pernix, Bacillus subtilis, Bordetella pertussis* TOX6, *Borrelia burgdorferi, Chlamydia trachomatis, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis,*

*Pseudomonas aeruginosa, Pyrococcus horikoshii,* Synechocystis PCC 6803, *Thermoplasma volcanium* and *Thermotoga maritima.*

In a further embodiment, combinations of nucleic acid fragments from one or more eukaryote genomes and/or one or more prokaryote genomes are used.

Wherein the nucleic acid fragments are from mixtures of organisms, it is preferred that those organisms are not normally found together in nature. In accordance with this embodiment of the invention, the process of combining nucleic acid fragments derived from diverse organisms not normally found together in nature enhances and controls diversity of the expression library produced using such nucleic acid fragments.

It is to be understood that the nucleic acid fragments used in the production of the expression libraries of the present invention are generated using art-recognized methods such as, for example, a method selected from the group consisting mechanical shearing, digestion with a nuclease and digestion with a restriction endonuclease. Combinations of such methods can also be used to generate the genome fragments. In a particularly preferred embodiment, copies of nucleic acid fragments from one or two or more genomes are generated using polymerase chain reaction (PCR) using random oligonucleotide primers.

The nucleic acid fragments or cDNA or amplified DNA derived therefrom are inserted into a suitable vector or gene construct in operable connection with a suitable promoter for expression of each peptide in the diverse nucleic acid sample. The construct used for the expression of the diverse nucleic acid fragment library is determined by the system that will be used to screen for those peptides that have a conformation sufficient for binding to a target protein or nucleic acid. Thus, consideration is generally given to an expression format suitable for screening the library.

In one embodiment, the vector or gene construct is suitable for in vitro display of an expressed peptide. Preferred in vitro display formats include, ribosome display, mRNA display or covalent display.

In another embodiment, the vector or gene construct is suitable for expressing a peptide in a cellular host. Preferred cellular hosts in this context are capable of supporting the expression of exogenous or episomal DNA such as, for example, a cellular host selected from the group consisting of a bacterial cell, yeast cell, insect cell, mammalian cell, and plant cell.

In another embodiment, the vector or gene construct is suitable for expressing a peptide in a multicellular organism. Preferred multicellular organisms for this purpose will include organisms having a compact genome and/or short life cycle to facilitate rapid high throughput screening, such as, for example, a plant (eg., *Arabidopsis thaliana* or *Nicotinia tabaccum*) or an animal selected from the group consisting of *Caenorhabditis elegans, Danio rerio, Drosophila melanogaster, Takifugu rubripes,* Mus sp. and *Rattus* sp.

Accordingly, one aspect of the present invention provides a method of constructing an expression library for expressing a peptide having a conformation sufficient for binding to a target protein or nucleic acid, said method comprising:
  (a) producing nucleic acid fragments from nucleic acids derived from two or more microorganisms or eukaryotes containing compact genomes, each of said microorganisms or eukaryotes having a substantially sequenced genome; and
  (b) inserting the nucleic acid fragments at (a) into a suitable expression construct thereby producing recombinant constructs, wherein each fragment is in operable connection with a promoter sequence that is capable of conferring expression of that fragment.

By way of exemplification, FIG. 1 shows one embodiment of the method of generating the expression library of the present invention, wherein nucleic acid fragments are isolated from multiple evolutionary diverse organisms and pooled in such a way as to ensure about equal representation of each of the genomes. Nested PCR using degenerate PCR primers amplifies sequences from the pooled genomes in a first round, and specific PCR amplifies the nucleic acid fragments so as to permit their direct cloning into an expression vector.

Preferably, the poor representation of low copy number sequences is reduced or minimized by normalizing the nucleic acid according to the complexity and size of the genome of the microorganism or compact eukaryote (ie., relative genome size of content of each contributing genome of the expression library). Thus, where genomes from more than one organism are used in the construction of the library, each of those contributing genomes is preferably used in an amount that is proportional to that complexity and size of the genome (or transcriptome), such as, for example, in comparison to the complexity and size of another genome in the mixture of genomes. This process results in about equal representation of the genome fragments in the biodiverse nucleic acid fragment library.

Accordingly, a preferred embodiment of the present invention provides a method of constructing an expression library for expressing a polypeptide having a conformation sufficient for binding to a target protein or nucleic acid, said method comprising:
  (a) producing nucleic acid fragments from nucleic acids derived from two or more microorganisms or eukaryotes containing compact genomes, each of said microorganisms or eukaryotes having a substantially sequenced genome; and
  (b) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

Preferably, the nucleic acid fragments are selected such that the encoded peptides have an average length that is about the length of a protein domain, eg., at least about 12-15 amino acids in length and more preferably at least about 15 amino acids in length or at least about 20 amino acids in length or at least about 30 amino acids in length.

Alternatively, or in addition, the nucleic acid fragments will preferably encode peptides that, on average, comprise or consist of a protein domain. As used herein, the term "protein domain" shall be taken to mean a discrete portion of a protein that assumes a secondary structure or conformation sufficient to permit said portion to perform a specific function in the context of a target protein or target nucleic acid and, in particular, to bind with high affinity to the target protein or nucleic acid. Preferred protein domains are not required to be constrained within a scaffold structure to bind to the target nucleic acid or target protein, or for said binding to be enhanced. Accordingly, it is particularly preferred that nucleic acid fragments used in the generation of the expression libraries of the present invention encode peptides that form stable secondary structures or conformations in the absence of a Trx loop or catalytically inactive staphylococcal nuclease peptide.

It is also preferred for the nucleic acid fragments of the expression libraries of the invention to encode a single protein domain. Accordingly, in a particularly preferred embodiment, the nucleic acid fragments of the expression libraries of the present invention will encode a peptide having an upper length of about 50 amino acid residues.

Accordingly, a preferred embodiment of the present invention provides a method of constructing an expression library for expressing a polypeptide having a conformation sufficient for binding to a target protein or nucleic acid, said method comprising:
(a) producing nucleic acid fragments from nucleic acids derived from one or two or more microorganisms or eukaryotes containing compact genomes, each of said microorganisms or eukaryotes having a substantially sequenced genome;
(b) selecting nucleic acid fragments from the fragments at (a) that encode a peptide having an average length of at least about 12-15 amino acid residues and/or encode a protein domain; and
(c) inserting the selected fragments at (b) into a suitable expression vector thereby producing recombinant constructs, wherein each fragment is in operable connection with a promoter sequence that is capable of conferring expression of that fragment.

In an alternative embodiment, the present invention provides a method of constructing an expression library for expressing a polypeptide having a conformation sufficient for binding to a target protein or nucleic acid, said method comprising:
(a) producing nucleic acid fragments from nucleic acids derived from two or more microorganisms or eukaryotes containing compact genomes, each of said microorganisms or eukaryotes having a substantially sequenced genome;
(b) selecting nucleic acid fragments from the fragments at (a) that encode a peptide having an average length of at least about 12-15 amino acid residues and/or encode a protein domain; and
(c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

In a further preferred embodiment, nucleic acid fragments are selected having sufficiently different nucleotide sequences to thereby enhance the nucleotide sequence diversity between the selected nucleic acid fragments, prior to or following their insertion into an expression vector or gene construct. Preferably, such a selection is performed prior to insertion of the nucleic acid fragments into a vector or gene construct.

In one embodiment, selecting nucleic acid fragments having sufficiently different nucleotide sequences comprises subjecting a base nucleic acid fragment to mutagenesis to produce a mutated fragment and optionally combining the mutated fragment with the base nucleic acid fragment.

In another embodiment, selecting nucleic acid fragments having sufficiently different nucleotide sequences comprises mutating a nucleic acid fragment thereby permitting the nucleic acid fragment to be read in any one or more of three forward reading frames. By "mutating" in this context is meant that one or more nucleotide residues are added to the 5'-end or 3'-end of a nucleic acid fragment. Alternatively, or in addition, "mutating" in this context means that the nucleotide sequence of a nucleic acid fragment is subjected to mutation by the insertion of one or more nucleotides into an internal region of the fragment, or by deleting one or more nucleotides from the fragment, or by substituting one or more nucleotides of the nucleic acid fragment. For example, by adding or deleting one or two or three nucleotides from the 5'-end of a base nucleic acid fragment and inserting the base fragment and each mutated fragment produced therefrom into an expression vector, the first codon becomes positioned at different locations relative to the translation start site such that each three forward reading frame is used.

In another embodiment, selecting nucleic acid fragments having sufficiently different nucleotide sequences comprises cloning a nucleic acid fragment in a reverse orientation relative to the orientation of the fragment in the context of the gene from which it was derived. In accordance with this embodiment, a reverse open reading frame is used.

In another embodiment, selecting nucleic acid fragments having sufficiently different nucleotide sequences comprises deleting a nucleic acid fragment having a sequence that is over represented in the genome or in the expression library. For example, it is preferred to delete or remove nucleic acid fragments comprising highly repetitive nucleotide sequences, or additional copies of nucleic acid fragments that are repeated in a genome (ie., to remove nucleic acid fragments comprising redundant nucleotide sequences of multiple copy or high copy number genes). It is to be understood that "redundant nucleotide sequences" does not include each and every copy of a repeated sequence, since it is preferred to leave at least one copy of such sequences in the nucleic acid fragment pool used to construct the expression library of the present invention.

Accordingly, a preferred embodiment of the present invention provides a method of constructing an expression library for expressing a polypeptide having a conformation sufficient for binding to a target protein or nucleic acid, said method comprising:
(a) producing nucleic acid fragments from nucleic acids derived from one or two or more microorganisms or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome; and
(c) inserting the selected fragments at (b) into a suitable expression construct thereby producing recombinant constructs, wherein each fragment is in operable connection with a promoter sequence that is capable of conferring expression of that fragment.

In an alternative embodiment, the present invention provides a method of constructing an expression library for expressing a polypeptide having a conformation sufficient for binding to a target protein or nucleic acid, said method comprising:
(a) producing nucleic acid fragments from nucleic acids derived from two or more microorganisms or eukaryotes containing compact genomes, each of said microorganisms or eukaryotes having a substantially sequenced genome;
(b) selecting nucleic acid fragments from the fragments at (a) that have sufficiently different nucleotide sequences thereby enhancing nucleotide sequence diversity among the selected fragments compared to the diversity of sequences in the genome; and (c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

In a particularly preferred embodiment, the present invention provides a method of constructing an expression library for expressing a polypeptide having a conformation sufficient for binding to a target protein or nucleic acid, said method comprising:
  (a) producing nucleic acid fragments from nucleic acids derived from one or two or more microorganisms or eukaryotes containing compact genomes, each of said microorganisms or eukaryotes having a substantially sequenced genome;
  (b) selecting nucleic acid fragments from the fragments at (a) that have sufficiently different nucleotide sequences thereby enhancing nucleotide sequence diversity among the selected fragments compared to the diversity of sequences in the genome and selecting nucleic acid fragments from the fragments at (a) that encode a peptide having an average length of at least about 12-15 amino acid residues and/or encode a protein domain; and
  (c) inserting the selected fragments at (b) into a suitable expression construct thereby producing recombinant constructs, wherein each fragment is in operable connection with a promoter sequence that is capable of conferring expression of that fragment.

In an alternative particularly preferred embodiment, the present invention provides a method of constructing an expression library for expressing a polypeptide having a conformation sufficient for binding to a target protein or nucleic acid, said method comprising:
  (a) producing nucleic acid fragments from nucleic acids derived from two or more microorganisms or eukaryotes containing compact genomes, each of said microorganisms or eukaryotes having a substantially sequenced genome;
  (b) selecting nucleic acid fragments from the fragments at (a) that have sufficiently different nucleotide sequences thereby enhancing nucleotide sequence diversity among the selected fragments compared to the diversity of sequences in the genome and selecting nucleic acid fragments from the fragments at (a) that encode a peptide having an average length of at least about 12-15 amino acid residues and/or encode a protein domain; and
  (c) inserting the selected fragments at (a) into a suitable expression vector in an amount proportional to the size of the genome from which the fragments were derived thereby producing recombinant constructs, wherein each fragment is in operable connection with a promoter sequence that is capable of conferring expression of that fragment.

Preferably, if the library is to be expressed in either a cellular system or in an organism then the method of producing an expression library in accordance with the present invention further comprises introducing the recombinant vector or recombinant gene construct into a host cell such that a nucleic acid fragment contained therein is capable of being expressed as a peptide or protein domain having a conformation sufficient for binding to target protein or nucleic acid.

A second aspect of the present invention relates to an expression library described according to the procedures described herein. Such libraries will comprise isolated nucleic acid fragments from one or two or more prokaryote or compact eukaryote genomes, wherein said fragments comprise, on average, an open reading frame of about 36 to about 150 nucleotides or about 250 nucleotides in length or sufficient to encode a single protein domain having a conformation sufficient to bind to a target nucleic acid or target protein. Preferably, the fragments comprise nucleotide sequences that are non-redundant or alternatively, encode peptides or protein domains comprising non-redundant amino acid sequences.

Preferably, expression libraries comprising mixtures of nucleic acid fragments from 2 or 3 or 4 or 5 or 6 or 7 or 8 or 9 or 10 or 11 or 12 or 13 or 14 or 15 or 16 or 17 or 18 or 19 or 20 prokaryote or compact eukaryote genomes. Preferably, such mixed libraries are normalized.

The present invention also relates to the use of the expression libraries to isolate a nucleic acid that encodes a peptide or protein domain, in particular a peptide having a conformation sufficient for binding to a target protein or target nucleic acid. In accordance with this aspect of the invention, the expression library of the present invention is screened to identify a peptide encoded by an inserted nucleic acid fragment of the library that binds to a target protein or target nucleic acid, such as, for example to modulate a specific protein:DNA or protein:protein interaction or a structure such as a cell wall or a membrane transport component.

Accordingly, a further aspect of the present invention provides a method of determining a peptide that binds to a target nucleic acid or target protein comprising:
  (a) screening an expression library of the present invention to identify a peptide expressed by the library that binds to the target protein or target nucleic acid; and
  (b) selecting a peptide from (a) that does not bind to said target protein or nucleic acid in its native environment.

Screening approaches suitable for performing the invention include for example, a method selected from the group consisting of yeast-2-hybrid, n-hybrid, reverse-2-hybrid, reverse n-hybrid, split two hybrid, bacterial display, phage display, retroviral display, covalent display and in vitro display. In a particularly preferred embodiment, the expression library is screened using a phage display method.

Another aspect of the present invention provides an isolated peptide or protein domain that binds to an immunoglobulin, wherein said immunoglobulin was not raised against the peptide or protein domain and wherein said peptide or protein domain does not have a native function of the protein against which the immunoglobulin was prepared (ie., it is not functionally homologous and does not have the same primary structure as the peptide against which the immunoglobulin was prepared). In one particularly preferred embodiment, the peptide or protein domain binds to antibodies against an allergen, more preferably a pollen allergen and even more preferably against a Der p1 allergen.

This aspect of the present invention clearly extends to any isolated nucleic acid encoding the peptide or protein domain that binds to the immunoglobulin. Another aspect of the present invention provides an isolated peptide or protein domain that partially or completely inhibits or antagonizes or blocks an interaction between two or more proteins in a cell. Preferably, the isolated peptide or protein domain blocks an interaction between SCL and another protein, or between E47 and another protein. Even more preferably, the isolated peptide or protein domain blocks an interaction between SCL and E47 in a cell. In a particularly preferred embodiment, the isolated peptide comprises an amino acid sequence selected from the group consisting of SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 79 and SEQ ID NO: 81.

This aspect of the present invention clearly extends to any isolated nucleic acid encoding the peptide or protein domain that partially or completely inhibits or antagonizes or blocks an interaction between two or more proteins in a cell. Exemplary nucleic acids provided herein comprise a nucleotide sequence selected from the group consisting of: SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 78 and SEQ ID NO: 80.

Another aspect of the present invention provides a database comprising the nucleotide sequences of nucleic acid fragments of an expression library of the present invention in computer readable form.

A related embodiment provides a database comprising amino acid sequences of peptides encoded by nucleic acid fragments of the present invention. Preferably, the database incorporates information regarding the secondary structure of the peptides, including predicted structure or a structure as determined by X-ray crystallography or other empirical means.

A further aspect of the present invention provides a method for determining or validating a target comprising
(a) screening an expression library of the present invention to identify a peptide expressed by the library that binds to a target protein or target nucleic acid;
(b) selecting a peptide from (a) that does not bind to said target protein or nucleic acid in its native environment; and
(c) expressing the selected peptide in an organism and determining a phenotype of the organism that is modulated by the target protein or target nucleic acid.

In a preferred embodiment, the target comprises a therapeutic or prophylactic target (eg., an oncoprotein or interaction between oncoproteins, a protein or nucleic acid associated with cancer (eg., a cancer marker) or other disease of an animal or human, or an antibacterial target, antihelminthic target, antiparasitic target, or antiviral target.

For example, the phenotype of an organism that expresses a tumor is assayed in the presence and absence of a peptide or protein domain that blocks an interaction between SCL and E47 in a screen of the expression library of the invention. Amelioration of the oncogenic phenotype by the expressed peptide indicates that the SCL/E47 is a suitable target for intervention, wherein the peptide is then suitably formulated for therapeutic intervention directly, or alternatively, small molecules are identified that are mimetics of the identified peptide or protein domain.

Accordingly, a further aspect of the present invention provides a method for identifying a therapeutic or prophylactic compound comprising
(a) screening an expression library of the present invention to identify a peptide expressed by the library that binds to a target protein or target nucleic acid;
(b) selecting a peptide from (a) that does not bind to said target protein or nucleic acid in its native environment;
(c) expressing the selected peptide in an organism and determining a phenotype of the organism that is modulated by the target protein or target nucleic acid; and
(d) identifying a mimetic compound of a peptide that modulated the phenotype of the organism.

DETAILED DESCRIPTION OF THE PREFERRED EMBODIMENTS

Figure 1:
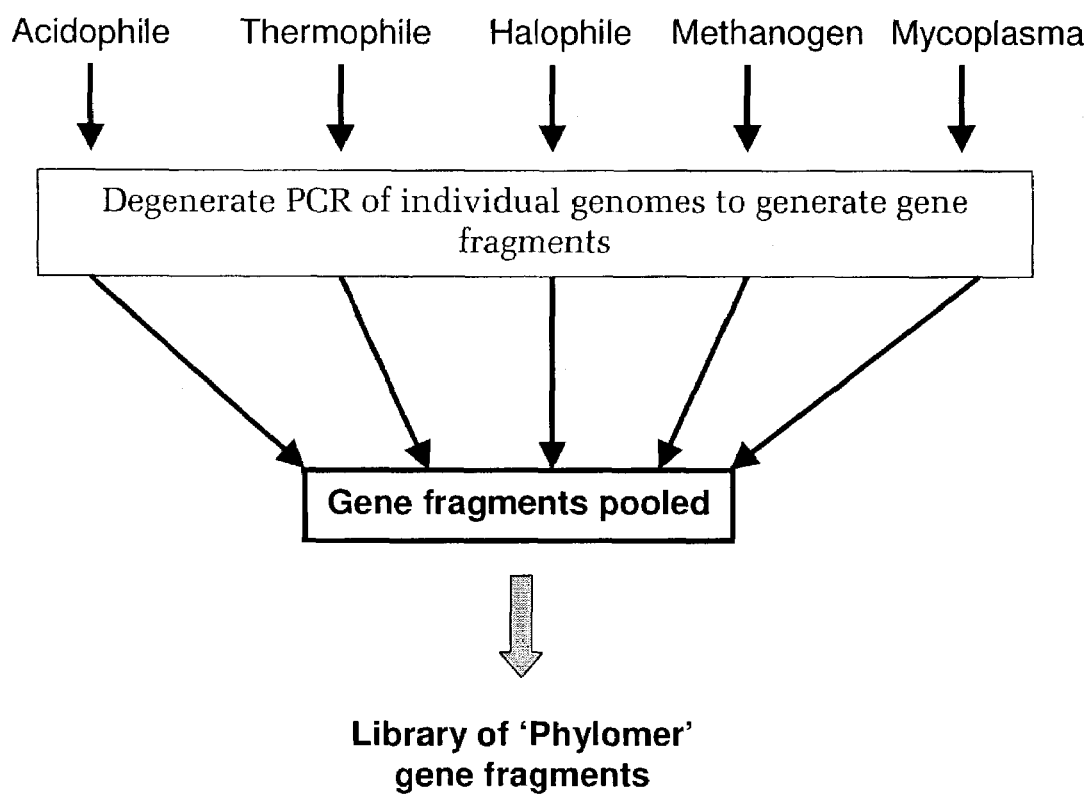
FIG. 1 is a schematic representation showing a simplified method of generating an expression library of the present invention, said library comprising nucleic acid fragments from multiple evolutionary diverse organisms. Initially nucleic acids are isolated from such organisms and pooled in such a way as to ensure equal representation of each of the genomes. Degenerate PCR is then used to amplify sequences from the pool of the genomes, before specific PCR is used to further amplify these nucleic acid fragments in such a way that they may be cloned into an expression vector.

One aspect of the present invention provides a method of constructing an expression library for expressing a polypeptide having a conformation sufficient for binding to a target protein or nucleic acid.

As used herein, the term "expression library" shall be taken to mean a plurality of nucleic acids cloned into a recombinant expression vector such that the cloned DNA fragments are expressed to produce peptides or proteins. As used herein, the terms "expression", "expressed" or "express" shall be taken to mean at least the transcription of a nucleotide sequence to produce a RNA molecule. The term "expression" "expressed" or "express" further means the translation of said RNA molecule to produce a peptide, polypeptide or protein.

As used herein, the term "having a conformation sufficient for binding to a target protein or nucleic acid" shall be taken to mean that an expressed peptide is capable of achieving a secondary structure or conformation sufficient for it to bind to a particular target protein or peptide or polypeptide, or alternatively, a target nucleic acid, preferably in the absence of a constraining peptide such as, for example a Trx loop. Such an affinity is to be interpreted in its broadest context to include, for example, the formation of a peptide:peptide complex, a peptide:protein complex, an antigen:antibody complex, and a peptide:nucleic acid complex.

One preferred embodiment of the present invention relates to the production of nucleic acid fragments from the genome of one or two or more prokaryotes or compact eukaryotes, each of said microorganisms or compact eukaryotes having a substantially sequenced genome.

The term "fragment" as used herein, shall be understood to mean a nucleic acid that is the same as part of, but not all of a nucleic acid that forms a gene.

As used herein, the term "gene" means the segment of nucleic acid, specifically DNA, capable of encoding a peptide or polypeptide, in the present context, a "nucleic acid fragment" is include regions preceding and/or following the coding region of a naturally occurring gene, eg. 5' untranslated or 3' untranslated sequences, as well as intervening sequences between individual coding sequences.

It will be apparent from the disclosure herein that the nucleic acid fragments used to produce the expression libraries in accordance with the present invention do not necessarily encode the same protein or peptide as in their native context (ie. the gene from which they were derived). In fact, the nucleic acid fragments will generally encode a hitherto unknown peptide, particularly if derived from a non-coding region of a native gene. All that is required is an open reading frame of sufficient length to encode a peptide or protein domain.

Nucleic acid fragments are generated by one or more of a variety of methods well known to those skilled in the art. Such methods include, for example, a method of producing nucleic acid fragments selected from the group consisting of mechanical shearing (eg by sonication or passing the nucleic acid through a fine gauge needle), digestion with a nuclease (eg Dnase 1), digestion with one or more restriction enzymes, preferably frequent cutting enzymes that recognize 4-base restriction enzyme sites and treating the DNA samples with radiation (eg. gamma radiation or ultra-violet radiation).

In another embodiment, copies of nucleic acid fragments isolated from one or two or more organisms are generated by polymerase chain reaction (PCR) using, for example, random or degenerate oligonucleotides. Such random or degenerate oligonucleotides include restriction enzyme recognition sequences to allow for cloning of the amplified nucleic acid into an appropriate nucleic acid vector. Methods of generating oligonucleotides are well known in the art and are described, for example, in Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151. Methods of performing PCR are also described in detail by McPherson et al., *In: PCR A Practical Approach.*, IRL Press, Oxford University Press, Oxford, United Kingdom, 1991.

In a preferred embodiment, the nucleic acid fragment comprises or consists of an open reading frame of nucleotides having a length sufficient to encode a protein domain and preferably, a single protein domain. Examples of protein domains include, for example protein domains selected from the group comprising, helix-loop helix (HLH), leucine zipper, zinc finger, SH2 domain, SH3 domain, WW domain, C2 domain, and proline rich region (PRR), amongst others.

Several studies have shown that the smallest natural domains that are able to fold autonomously consist of about 30 amino acids to about 50 amino acids in length (Yang, *Biochemistry* 38, 465, 1999, Horng. *Biochemistry*, 41:13360, 2002, Neidigh, *Nature Structural Biology*, 9:425, 2002). In this context, the term "autonomous" means independent of controlling factors, thus a protein that is able to fold autonomously does so in the absence of factors such as, for example disulphide bonds, ligand binding, or the use of a constraint such as, for example a Trx loop. Accordingly, in one preferred embodiment of the present invention, the nucleic acid fragments of the expression library will consist of an open reading frame sufficient to encode a peptide of about 30-50 amino acids in length.

It is also known that factors such as disulphide bonds control the folding of the peptides. U.S. Pat. Nos. 6,361,969 and 6,083,715 describe the expression of protein disulphide isomerases to induce disulphide bond formation in proteins. Studies by Vranken (In: *Proteins*, 47:14-24, 2002) have suggested that natural protein domains stabilized by disulphide bonding can be as small as 15 to 25 amino acids in length. Accordingly, an alternative embodiment of the present invention uses nucleic acid fragments that consist of an open reading frame sufficient to encode a peptide of about 15 amino acids to about 25 amino acids in length.

It will be apparent from the preceding description that the present invention preferably utilizes nucleic acid fragments having a length of about 45 to about 150 nucleotides in length or about 250 nucleotides in length. However, it is to be understood that some variation from this range is permitted, the only requirement being that, on average, nucleic acid fragments generated encode a protein domain or a peptide comprising about 15 to about 50 amino acids in length, and more preferably about 20 to about 50 amino acids in length and still more preferably about 30 to about 50 amino acids in length.

Methods of producing nucleic acid fragments and separating said fragments according to their molecular weight are well known in the art and include, for example, the fragmentation methods supra and a method of separation selected from the group comprising, agarose gel electrophoresis, pulse field gel electrophoresis, polyacrylamide gel electrophoresis, density gradient centrifugation and size exclusion chromatography. A number of other methods for separating DNA fragments by their size are known in the art and are described, for example in Sambrook et al (In:).

The genomic nucleic acid is isolated from a variety of sources. In one preferred embodiment, genomic DNA is isolated from a prokaryotic organism. Exemplary prokaryotic sources of nucleic acid fragments include, *Aeropyrum pernix, Agrobacterium tumeficians, Aquifex aeolicus, Archeglobus fulgidis, Baccilus halodurans, Bacillus subtilis, Borrelia burgdorferi, Brucella melitensis, Brucella suis, Bruchnera* sp., *Caulobacter crescentus, Campylobacter jejuni, Chlamydia pneumoniae, Chlamydia pneumoniae, Chlamydia trachomatis, Chlamydia muridarum, Chlorobium tepidum, Clostridium acetobutylicum, Deinococcus radiodurans, Escherichia coli, Haemophilus influenzae* Rd, *Halobacterium* sp., *Helicobacter pylori, Methanobacterium thermoautotrophicum, Lactococcus lactis, Listeria innocua, Listeria monocytogenes, Methanococcus jannaschii, Mesorhizobium loti, Mycobacterium leprae, Mycobacterium tuberculosis, Mycoplasma genitalium, Mycoplasma penetrans, Mycoplasma pneumoniae, Mycoplasma pulmonis, Neisseria meningitidis, Oceanobacillus iheyensis, Pasteurella multocida, Pseudomonas aeruginosa, Pseudomonas putida, Pyrococcus horikoshii, Rickettsia conorii, Rickettsia prowazekii, Salmonella typhi, Salmonella typhimurium, Shewanella oneidensis* MR-1, *Shigella flexneri* 2a, *Sinorhizobium meliloti, Staphylococcus aureus, Streptococcus agalactiae, Streptococcus agalactiae, Streptococcus mutans, Streptococcus pneumoniae, Streptococcus pyogenes, Streptomyces avermitilis, Streptomyces coelicolor, Sulfolobus solfataricus, Sulfolobus tokodaii, Synechocystis* sp., *Thermoanaerobacter tengcongensis, Thermoplasma acidophilum, Thermoplasma volcanium, Thermotoga maritima, Treponema pallidum, Ureaplasma urealyticum, Vibrio cholerae, Xanthomonas axonopodis* pv., *Citri, Xanthomonas campestris* pv., *Campestris, Xylella fastidiosa,* and *Yersinia pestis.*

Methods of isolating genomic DNA from prokaryotic organisms are well known in the art and are described in, for example, Ausubel et al (In: Current Protocols in Molecular Biology. Wiley Interscience, ISBN 047 150338, 1987) or (Sambrook et al., In:).

In an alternative embodiment, genomic nucleic acid is from a compact eukaryote. As used herein the term "compact eukaryote" shall be taken to mean any organism of the superkingdom Eukaryota that has a haploid genome size of less than about 1700 mega base pairs (Mbp), and preferably, less than 100 Mbp. Exemplary compact eukaryotes that are suitable for this purpose include *Arabidopsis thaliana, Anopheles gambiae, Brugia malayi, Caenorhabditis elegans, Danio rerio, Drosophila melanogaster, Eimeria tenella, Eimeria acervulina, Entamoeba histolytica, Oryzias latipes, Oryza sativa, Plasmodium falciparum, Plasmodium vivax, Plasmodium yoelii, Sarcocystis cruzi, Saccharomyces cerevesiae, Schizosaccharomyces pombe, Schistosoma mansoni, Takifugu rubripes, Theileria parva, Tetraodon fluviatilis, Toxoplasma gondii, Tryponosoma brucei,* and *Trypanosoma cruzi.*

Furthermore, it is preferred that said compact eukaryotes contain genomes have less repetitive nucleotide than, for example humans. Such information can be determined from information from NCBI or TIGR.

As used herein the term "NCBI" shall be taken to mean the database of the National Center for Biotechnology Information at the National Library of Medicine at the National Institutes of Health of the Government of the United States of America, Bethesda, Md., 20894.

As used herein the term "TIGR" shall be taken to mean the database of The Institute of Genomic Research, Rockville, Md., 20850.

A preferred example of an organism having a compact genome is the Japanese puffer fish, *Takifugu rubripes. T. rubripes* has a haploid genome size of approximately 400 Mbp, with a gene density of about 16%. This is compared to the human genome, which has a size in excess of 3000 Mbp of which only about 3% of nucleotide sequences encode proteins. The absolute number of native genes in the *T. rubripes* genome is comparable to that in the human genome, suggesting fewer repetitive sequences occur in *T. rubripes.* This feature makes *T. rubripes* particularly useful as a source of nucleic acid fragments of the expression libraries of the present invention. This is because a nucleic acid fragment derived from the genome of a compact eukaryote has an increased probability of encoding a protein domain that is contained within a naturally occurring protein in its native context, compared to a sequence derived from a non-compact eukaryote.

It is to be understood that, whilst such native domains of proteins is expressed by the libraries of the invention, the invention is not limited to the expression of known protein domains. Moreover, it is to be understood that the expression libraries of the invention are screened using a process that excludes the selection of clones that encode a known protein domain having its native function. Accordingly, the present invention is directed to products and processes for isolating peptides having new or enhanced functions.

Methods of isolating genomic DNA from eukaryotic organisms are well known in the art and are described in, for example, Ausubel et al (In: Current Protocols in Molecular Biology. Wiley Interscience, ISBN 047 150338, 1987) or (Sambrook et al (In:).

In a further embodiment of the present invention, the nucleic acid fragments are derived from complimentary DNA (cDNA). Those skilled in the art will be aware that cDNA is generated by reverse transcription of RNA using, for example, avian reverse transcriptase (AMV) reverse transcriptase or Moloney Murine Leukemia Virus (MMLV) reverse transcriptase. Such reverse transcriptase enzymes and the methods for their use are well known in the art, and are obtainable in commercially available kits, such as, for example, the Powerscript kit (Clontech), the Superscript II kit (Invitrogen), the Thermoscript kit (Invitrogen), the Titanium kit (Clontech), or Omniscript (Qiagen).

Methods of isolating mRNA from a variety of organisms are well known in the art and are described for example in, Ausubel et al (In: Current Protocols in Molecular Biology. Wiley Interscience, ISBN 047 150338, 1987) or Sambrook et al (In:).

Methods of generating cDNA from isolated RNA are also commonly known in the art and are described in for example, Ausubel et al (In: Current Protocols in Molecular Biology. Wiley Interscience, ISBN 047 150338, 1987) or (Sambrook et al (In: ).

In a preferred embodiment, the nucleic acid fragments generated from RNA or cDNA are normalized to reduce any bias toward more highly expressed genes. Methods of normalizing nucleic acids are well known in the art, and are described for example in, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001) and Soares et al Curr. Opinion Biotechnol 8, 542-546, 1997, and references cited therein. One of the methods described by Soares uses reasssociation-based kinetics to reduce the bias of the library toward highly expressed sequences. Alternatively, cDNA is normalized through hybridization to genomic DNA that has been bound to magnetic beads, as described in Kopczynski et al, Proc. Natl. Acad. Sci. USA, 95(17), 9973-9978, 1998. This provides an approximately equal representation of cDNA sequences in the eluant from the magnetic beads. Normalized expression libraries produced using cDNA from one or two or more prokaryotes or compact eukaryotes are clearly contemplated by the present invention.

In a particularly preferred embodiment, the nucleic acid fragments are derived from a prokaryote and/or compact eukaryote having a substantially sequenced genome. An advantage of using such fragments is that bioinformatic data can be assembled and used to provide more complete information about the composition of a library than would be possible using uncharacterized libraries. This facilitates the generation of DNA arrays containing sequences derived from many or all of the nucleic acid fragments of the library. Methods used in the generation and screening of DNA arrays are well known in the art and are described in for example, Schena (In: Microarray Analysis, John Wiley and Sons, ISBN: 0471414433, 2002). The use of DNA arrays in the high-throughput analysis of the screening of a biodiverse nucleic acid fragment to determine the sequences of positive clones is particularly contemplated.

As used herein "substantially sequenced genome" shall be taken to mean that at least about 60% of the genome has been sequenced. More preferably at least about 70% of the genome has been sequenced, and more preferably at least about 75% of the genome has been sequenced. Even more preferably at least about 80% of the genome has been sequenced.

Methods for determining the amount of a genome that has been sequenced are well known in the art. Furthermore, information regarding those sequences that have been sequenced is readily obtained from publicly available sources, such as, for example, the databases of NCBI or TIGR, thereby facilitating determination of the diversity of the genome.

Organisms having a substantially sequenced genome include, for example, an organism selected from the group consisting of *Aeropyrum pernix, Agrobacterium tumeficians, Anopheles gambiae, Aquifex aeolicus, Arabidopsis thaliana, Archeglobus fulgidis, Baccilus halodurans, Bacillus subtilis, Borrelia burgdorferi, Brucella melitensis, Brucella suis, Bruchnera* sp., *Brugia malayi, Caenorhabditis elegans, Caulobacter crescentus, Campylobacter jejuni, Chlamydia pneumoniae, Chlamydia pneumoniae, Chlamydia trachomatis, Chlamydia muridarum, Chlorobium tepidum, Clostridium acetobutylicum, Danio rerio, Deinococcus radiodurans, Drosophila melanogaster, Eimeria tenella, Eimeria acervulina, Entamoeba histolytica, Escherichia coli, Haemophilus influenzae* Rd, *Halobacterium* sp., *Helicobacter pylori, Methanobacterium thermoautotrophicum, Lactococcus lactis, Listeria innocua, Listeria monocytogenes, Methanococcus jannaschii, Mesorhizobium loti, Mycobacterium leprae, Mycobacterium tuberculosis, Mycoplasma genitalium, Mycoplasma penetrans, Mycoplasma pneumoniae, Mycoplasma pulmonis, Neisseria meningitidis, Oceanobacillus iheyensis, Oryzias latipes, Oryza sativa, Pasteurella multocida, Plasmodium falciparum, Plasmodium vivax, Plasmodium yoelii, Pseudomonas aeruginosa, Pseudomonas putida, Pyrococcus horikoshii, Rickettsia conorii, Rickettsia prowazekii, Saccharomyces cerevisiae, Salmonella typhi, Salmonella typhimurium, Sarcocystis cruzi, Schistosoma mansoni, Schizosaccharomyces pombe, Shewanella oneidensis* MR-1, *Shigella flexneri* 2a, *Sinorhizobium meliloti, Staphylococcus aureus, Streptococcus agalactiae, Streptococcus agalactiae, Streptococcus mutans, Streptococcus pneumoniae, Streptococcus pyogenes, Streptomyces avermitilis, Streptomyces coelicolor, Sulfolobus solfataricus, Sulfolobus tokodaii, Synechocystis* sp., *Takifugu rubripes, Tetraodon fluviatilis, Theileria parva, Thermoanaerobacter tengcongensis, Thermoplasma acidophilum, Thermoplasma volcanium, Thermotoga maritima, Toxoplasma gondii, Treponema pallidum, Tryponosoma brucei, Trypanosoma cruzi Ureaplasma urealyticum, Vibrio cholerae, Xanthomonas axonopodis* pv, *Citri, Xanthomonas campestris* pv., *Campestris, Xylella fastidiosa,* and *Yersinia pestis.*

In a particularly preferred embodiment, nucleic acid fragments are selected that have sufficiently different or divergent nucleotide sequences to thereby enhance nucleotide sequence diversity among the selected fragments compared to the diversity of sequences in the genome from which they were derived.

In one embodiment a nucleic acid fragment is selected such that the encoded polypeptide varies by one or more amino acids with regard to the amino acid sequence of the polypeptide encoded by another fragment in the library, a process that is facilitated using genomes that are substantially sequenced.

In an alternative embodiment, the nucleotide sequence of a nucleic acid fragment is mutated by a process such that the encoded peptide varies by one or more amino acids compared to the "template" nucleic acid fragment. The "template" may have the same nucleotide sequence as the original nucleic acid fragment in its native context (ie. in the gene from which it was derived). Alternatively, the template may itself be an intermediate variant that differs from the original nucleic acid fragment as a consequence of mutagenesis. Mutations include at least one nucleotide difference compared to the sequence of the original fragment. This nucleic acid change may result in for example, a different amino acid in the encoded peptide, or the introduction or deletion of a stop codon. Accordingly, the diversity of the nucleic acids of the expression library and the encoded polypeptides is enhanced by such mutation processes.

In one embodiment, the nucleic acid fragments are modified by a process of mutagenesis selected from the group consisting of, mutagenic PCR, expressing the nucleic acid fragment in a bacterial cell that induces a random mutation, site directed mutagenesis and expressing a nucleic acid fragment in a host cell exposed to a mutagenic agent such as for example radiation, bromo-deoxy-uridine (BrdU), ethylnitrosurea (ENU), ethylmethanesulfonate (EMS) hydroxylamine, or trimethyl phosphate amongst others.

In a preferred embodiment, the nucleic acid fragments are modified by amplifying a nucleic acid fragment using mutagenic PCR. Such methods is include a process selected from the group consisting of: (i) performing the PCR reaction in the presence of manganese; and (ii) performing the PCR in the presence of a concentration of dNTPs sufficient to result in misincorporation of nucleotides.

Methods of inducing random mutations using PCR are well known in the art and are described, for example, in Dieffenbach (ed) and Dveksler (ed) (In: PCR Primer: A Laboratory Manual, Cold Spring Harbour Laboratories, NY, 1995). Furthermore, commercially available kits for use in mutagenic PCR are obtainable, such as, for example, the Diversify PCR Random Mutagenesis Kit (Clontech) or the GeneMorph Random Mutagenesis Kit (Stratagene).

In one embodiment, PCR reactions are performed in the presence of at least about 200 μM manganese or a salt thereof, more preferably at least about 300 μM manganese or a salt thereof, or even more preferably at least about 500 μM or at least about 600 μM manganese or a salt thereof. Such concentrations manganese ion or a manganese salt induce from about 2 mutations per 1000 base pairs (bp) to about 10 mutations every 1000 bp of amplified nucleic acid (Leung et al *Technique* 1, 11-15, 1989).

In another embodiment, PCR reactions are performed in the presence of an elevated or increased or high concentration of dGTP. It is preferred that the concentration of dGTP is at least about 25 μM, or more preferably between about 50 μM and about 100 μM. Even more preferably the concentration of dGTP is between about 100 μM and about 150 μM, and still more preferably between about 150 μM and about 200 μM. Such high concentrations of dGTP result in the misincorporation of nucleotides into PCR products at a rate of between about 1 nucleotide and about 3 nucleotides every 1000 bp of amplified nucleic acid (Shafkhani et al *BioTechniques* 23, 304-306, 1997).

PCR-based mutagenesis is preferred for the mutation of the nucleic acid fragments of the present invention, as increased mutation rates is achieved by performing additional rounds of PCR.

In another preferred embodiment, the nucleic acid of the expression library is mutated by inserting said nucleic acid into a host cell that is capable of mutating nucleic acid. Such host cells are deficient in one or more enzymes, such as, for example, one or more recombination or DNA repair enzymes, thereby enhancing the rate of mutation to a rate that is rate approximately 5,000 to 10,000 times higher than for non-mutant cells. Strains particularly useful for the mutation of nucleic acids carry alleles that modify or inactivate components of the mismatch repair pathway. Examples of such alleles include alleles selected from the group consisting of mutY, mutM, mutD, mutT, mutA, mutC and mutS. Bacterial cells that carry alleles that modify or inactivate components of the mismatch repair pathway are well known in the art, such as, for example the XL-1Red, XL-mutS and XL-mutS-Kan$^r$ bacterial cells (Stratagene).

Alternatively the nucleic acid fragments are cloned into a nucleic acid vector that is preferentially replicated in a bacterial cell by the repair polymerase, Pol I. By way of exemplification, a Pol I variant strain will induce a high level of mutations in the introduced nucleic acid vector, thereby enhancing sequence diversity of the nucleic acid used to generate the expression library of the present invention. Such a method is described by Fabret et al (*In: Nucl Acid Res*, 28, 1-5 2000), which is incorporated herein by reference.

In a further preferred embodiment the mutated nucleic acid fragments are combined with the non-mutated fragments from which they were derived, for subcloning into an expression vector. In this way, the nucleotide diversity of the expression library of the present invention is enhanced, as is the diversity of the conformations of the expressed peptides and proteins.

In another embodiment, the sequence diversity of a nucleic acid fragment is increased, such as, for example, using a synthetic shuffling technique, such as, for example, the process described by Ness et al, *Nature Biotechnology*, 20, 1251-1255, 2002, which is incorporated herein by reference. In adapting such a technique to the present invention, functionally homologous nucleic acid fragments are selected from the expression library, using methods described herein. By "functionally homologous" in this context means that the selected fragments bind to the same target protein or target nucleic acid. The amino acid sequence of each peptide that binds to the target is determined using methods well known in the art, and the sequences are aligned using an algorithm well known in the art. A consensus sequence is determined from the alignment that provides for highly conserved residues, as well as elucidating those residues that are structurally similar albeit not strictly conserved. The structural features of the peptides are also derived using X-ray crystallography and/or computer-based modelling procedures. Accordingly, the divergence in the identified peptides from an individual screen permits the identification of both primary and secondary structural features that are required for binding to the target protein or target nucleic acid to occur. Based upon the bioinformatic data obtained, oligonucleotides (eg., degenerate oligonucleotides or non-degenerate oligonucleotides as appropriate) are designed that encode all of the possible peptides that bind to the target protein or target nucleic acid. These oligonucleotides are then assembled using PCR employing multiple rounds of amplification, to generate a plurality of nucleic acids encoding all possible peptide combinations. Accordingly, an amino acid sequence that is not normally found in nature is produced.

In a further embodiment, a significant proportion of the nucleic acid fragments are cloned into a gene construct in at least two forward open reading frames, and preferably three forward open reading frames, to thereby enhance the number of divergent peptides or proteins that are encoded by a particular nucleic acid fragment. In this context, the term "significant proportion" means at least about 30% to 50%, preferably at least about 40% to 60%, more preferably at least about 50% to 70%, still more preferably at least about 60% to 80% and still more preferably greater than about 70% or 80% of the total nucleic acid fragments that are subcloned successfully into a suitable gene construct such that more than one open reading frame can be utilized for expression. As will be known to those skilled in the art, procedures for cloning a single nucleic acid into a gene construct in multiple reading frames are well known.

Particularly preferred methods of subcloning a nucleic acid fragment in multiple three reading frames comprise a process selected from the group consisting of:
(a) ligating the nucleic acid fragment to a linker or adaptor, such as for example, one or more linkers modified to contain an additional one or two or three base pairs, or a multiple of one or two or three nucleotides;
(b) Placing each nucleic acid fragment operably under the control of a Kozak consensus sequence and at different distances therefrom (eg. one or two or three nucleotides or a multiple of one or two or three nucleotides) from said Kozak consensus sequence;
(c) Placing a fragment under control of sequences that confer transcriptional and/or translational slippage.

By ligating the nucleic acid fragment to a linker or adaptor, the number of introduced nucleotides can be varied such that a significant proportion of the nucleic acid fragments are introduced into an expression vector or gene construct in at least two and preferably three reading frames. Linkers or adaptors are ligated to the 5'-end of the nucleic acid fragment such that, on average, a different length linker or adaptor is added to each nucleic acid fragment having the same sequence. This is generally achieved by varying the relative proportions of each linker/adaptor to the nucleic acid fragments. Naturally, each linker/adaptor of differing length is generally in equimolar concentration in the ligation reaction, and the total concentration of linker/adaptor 3'-ends is held in equimolar concentration to the total concentration of 5'-ends of the nucleic acid fragments being ligated. Methods of ligating adaptors to nucleic acids are well known in the art and are described in for example, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

As an alternative to separately adding the linkers/adaptors to the nucleic acid fragments prior to subcloning into a suitable gene construct, a suitable gene construct is used that comprises additional nucleotides 3' of a translation initiation signal, and provides for sub-cloning of nucleic acid fragments in each reading frame. As will be known to those skilled in the art, each reading frame in a gene construct is generally accessed by digesting the gene construct with a different restriction endonuclease and then sub-cloning nucleic acid fragments into the digested, linearized vector. By "sub-cloning" means a process involving or comprising a ligation reaction.

Alternatively, site directed mutagenesis is used to introduce additional nucleotides after the translation initiation site of the gene construct. Methods of site-directed mutagenesis are well known in the art, and are described for example, in Dieffenbach (eds) and Dveksler (ed) (In: PCR Primer: A Laboratory Manual, Cold Spring Harbour Laboratories, NY, 1995). Furthermore, kits containing instruction and reagents necessary for site-directed mutagenesis are commercially available, such as, for example, the Quikchange site directed mutagenesis kit (Stratagene).

Furthermore, expression vectors are commercially available that have been modified to include an additional one or two nucleotides after the transcription start codon to allow for cloning of a nucleic acid in at least two and preferably three reading frames. Such vectors include, for example, the pcDNA (A, B, or C) vector suite (Invitrogen).

By positioning each nucleic acid fragment so that expression is placed operably under the control of a Kozak consensus sequence and at different distances therefrom, a significant proportion of the nucleic acid fragments is inserted into the vector in at least two and preferably three reading frames. A preferred Kozak sequence has the core sequence RNNATG (SEQ ID NO: 1), wherein R is a purine (ie. A or G) and N is any nucleotide. A particularly preferred Kozak sequence for expression of a polypeptide in eukaryotic cells comprises the sequence CCRCCATG (SEQ ID NO: 2) or GCCAGCCATGG (SEQ ID NO: 3). A preferred Kozak sequence for the expression of polypeptides in plants is CTACCATG (SEQ ID NO: 4).

A Kozak consensus sequence is generated using synthetic oligonucleotides in a process that is well known in the art and described, for example, in, Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151. Alternatively a Kozac sequence is isolated from a natural or recombinant source using methods well known in the art, such as for example using from the group, restriction enzyme digestion or PCR.

In one embodiment, the Kozak sequence is generated as an oligoniucleotide or nucleic acid fragment and then ligated 5' of the nucleic acid fragment (ie. the nucleic acid fragment being sub-cloned). Methods of ligating such oligonucleotides or fragments are well known in the art and are described in for example, Ausubel et al (In: Current Protocols in Molecular Biology. Wiley Interscience, ISBN 047 150338, 1987) or (Sambrook et al (In: Molecular Cloning: Molecular Cloning: A Laboratory Manual, Cold Spring Harbor Laboratories, New York, Third Edition 2001). As with other ligations, the total concentration of nucleic acid of each ligating species (ie. the Kozak containing fragment and the nucleic acid ) should preferably be equimolar. Naturally to ensure that a significant proportion of nucleic acid fragments are ligated in each reading frame, the Kozak-containing fragments of differing length should also be present in approximately equimolar concentration.

As an alternative to separately adding the Kozak consensus sequence oligonucleotide or fragment to the nucleic acid fragment prior to subcloning into a suitable vector, an expression vector is used that comprises a translation start site and provides for subcloning of nucleic acid fragments in each reading frame. As will be known to those skilled in the art, each reading frame in such a vector is generally accessed by digesting the vector with a different restriction enzyme and then subcloning fragments into the digested, linearized vector.

When the nucleic acid fragment of the present invention is to be expressed in prokaryotic cells, it is particularly preferred that the Kozak sequence of the above embodiments is replaced with a ribosome binding sequence, or Shine Dalgarno sequence. A particularly preferred Shine Dalgarno sequence consists of nucleic acids having the nucleotide sequence GAAGAAGATA (SEQ ID NO: 5).

By placing a fragment under control of sequences that confer transcriptional and/or translational slippage is meant that the fidelity of the start site for transcription and/or translation is reduced such that translation is initiated at different sites. Accordingly, such a sequence is cause the expression of several different polypeptides.

In one embodiment translational slippage (or translational frameshifting) is induced using nucleic acid comprising of the consensus sequence $N_1N_1N_1N_2N_2N_2N_3$, wherein N represents any nucleotide and all nucleotides represented by $N_1$ are the same nucleotide, all nucleotides represented by $N_2$ are the same nucleotide. In accordance with this embodiment, $N_1$ and/or $N_2$ and/or $N_3$ are the same or different. A particularly preferred translational slippage sequence for use in a eukaryote will comprise a sequence selected from the group consisting of: AAAAAAC (SEQ ID NO: 6), AAATTTA (SEQ ID NO: 7), AAATTTT (SEQ ID NO: 8), GGGAAAC (SEQ ID NO: 9), GGGCCCC (SEQ ID NO: 10), GGGTTTA (SEQ ID NO: 11), GGGTTTT (SEQ ID NO: 12), TTTAAAC (SEQ ID NO: 13), TTTAAAT (SEQ ID NO: 14), TTTTTA (SEQ ID NO: 15), and GGATTTA (SEQ ID NO: 16). In an alternative embodiment, a sequence that induces translational slippage in yeast is CTTAGGC (SEQ ID NO: 17) or GCGAGTT (SEQ ID NO: 18). In yet another embodiment a sequence that induces translational slippage in mammals is TCCTGAT (SEQ ID NO: 19).

In another embodiment, a translational slippage sequences for use in prokaryotic organisms includes, but is not limited to s sequence selected from the group consisting of AAAAAAG (SEQ ID NO: 20); AAAAAAA (SEQ ID NO: 21), AAAAAAC (SEQ ID NO: 22), GGGAAAG (SEQ ID NO: 23), AAAAGGG (SEQ ID NO: 24), GGGAAAA (SEQ ID NO: 25), TTTAAAG (SEQ ID NO: 26) and AAAGGGG (SEQ ID NO: 27). It is particularly preferred that this translational slippage sequence is positioned about 7 to about 19 nucleotides downstream of a Shine Dalgarno sequence. In an alternative embodiment, a nucleic acid that induces translational slippage in bacterial cells comprises the nucleotide sequence CTT (SEQ ID NO: 28), and is positioned 3 nucleotides upstream of a Shine Dalgarno sequence controlling the expression of the nucleic acid fragment.

A translational slippage sequence is generated using synthetic oligonucleotides, or isolated from a natural or recombinant source, for example the prfB gene, the dnaX gene, the mammalian ornithine decarboxylase antizyme, in addition to various retroviruses, coronaviruses, retrotransposons, virus-like sequences in yeast, bacterial genes and bacteriophage genes. Such a sequence is isolated using a method that is well known in the art, such as for example, restriction enzyme digestion or PCR.

It is preferred that sequences that confer translational slippage are ligated to the 5'-end of the nucleic acid fragment in the same manner as for adaptor addition. Methods of ligating adaptors are well known in the art and are described in for example, Ausubel et al (In: Current Protocols in Molecular Biology. Wiley Interscience, ISBN 047 150338, 1987) or (Sambrook et al (In: Molecular Cloning: Molecular Cloning: A Laboratory Manual, Cold Spring Harbor Laboratories, New York, Third Edition 2001).

It is also preferred that the sequences that confer transcriptional or translational slippage are incorporated into the expression vector or gene construct into which the nucleic acid fragment is inserted, such that it is positioned upstream (ie. 5') of the translational start site in the fragment.

In another embodiment, transcriptional slippage is induced by the introduction of a stretch of nucleotides with a sequence such as, for example, $T_9$ or $A_9$. Transcriptional slippage sequences are preferably cloned downstream (ie. 3') of the site of initiation of transcription. It is also preferred to position a transcriptional slippage sequence upstream (5') of a translational start site in the nucleic acid fragment. Accordingly, the transcriptional slippage sequence is included in the expression vector or gene construct into which the nucleic acid fragment is inserted.

Accordingly, the nucleic acids that form the transcriptional slippage sequence is ligated to the 5' end of a nucleic acid fragment, in conjunction with a translation start site.

It will be apparent from the preceding description that the transcriptional slippage sequence is incorporated into the expression vector or gene construct upstream of the translation start site, and downstream of the site of initiation of transcription.

Preferably, the nucleic acid fragments derived from the prokaryote or compact eukaryote genome are inserted into a gene construct in both the forward and/or reverse orientation, such that 1 or 2 or 3 or 4 or 5 or 6 open reading frames of said nucleic acid fragments are utilized. Methods of bi-directionally inserting fragments into vectors are well known in the art.

It will be apparent to the skilled artisan that, by subcloning the nucleic acid fragments in multiple reading frames into a suitable expression vector, it is possible to encode a peptide or protein domain that does not occur in nature, as well as producing a variety of natural peptide domains. Accordingly, the diversity of the nucleic acids of the expression library and their encoded peptides are greatly enhanced in these modified nucleic acid fragment expression libraries.

In a preferred embodiment, the expression libraries of the present invention are normalized to remove any redundant nucleic acid from the genome. As cited herein the term "redundant nucleic acid" shall be taken to mean those nucleic acid fragments having the same sequence, such as, for example, high copy number or repetitive sequences. Nucleic acid fragments derived from multiple homologous sequences, whether derived from the same or a different species can be subject to normalization to reduce the presence of redundant sequences in the expression library. Similarly, nucleic acid fragments derived from repetitive DNA and nucleic acid fragments derived from pseudogenes can be subject conveniently to normalization. Methods of normalizing libraries to remove redundant nucleic acid are well known in the art and are described, for example, by Ausubel et al., In: Current Protocols in Molecular Biology. Wiley Interscience, ISBN 047 150338, 1987, or Diversa Corporation (U.S. Pat. No. 5,763,239), or Sambrook et al., In: Molecular Cloning: Molecular Cloning: A Laboratory Manual, Cold Spring Harbor Laboratories, New York, Third Edition 2001, or Bonaldo et al., *Genome Res.* 6(9), 791-806, 1997. In one embodiment, the nucleic acid fragments are subjected to hydroxyapatite chromatography to remove redundant or highly repetitive sequences. The success of such a normalization process can be determined, for example, by hybridizing labelled non-normalized and normalized DNA to Southern blots of genomic DNA and comparing the amount of label bound to each blot. The amount of bound label is comparable to the amount of hybridized DNA. A reduced hybridization signal for normalized libraries indicates that iterative sequences have been reduced in the normalized pool.

In one embodiment the nucleic acids used to produce the expression libraries of the present invention are isolated from a single organism. In this case, nucleic acid fragments are generated from nucleic acid derived from a distinct prokaryote or compact eukaryote.

In another embodiment of the present invention the nucleic acids are derived from two or more prokaryotes and/or compact eukaryotes including any and all combinations thereof.

It is especially preferred that the prokaryote(s) and/or compact eukaryote(s) used to produce expression libraries from combined genomes are evolutionarily diverse organisms. As used herein the term "evolutionary diverse" shall be taken to mean those organisms that when compared at the genetic level, show a significant degree of genetic diversity. As used herein the term "significant degree of genetic diversity" shall be taken to mean, that the genes of the prokaryotes or compact eukaryotes differ, by at least about 10% to 30% at the nucleic acid level. More preferably the genetic sequences of the prokaryotes or compact eukaryotes differ by at least about 30% to 40% at the nucleic acid level. More preferably the genetic sequences of the prokaryotes or compact eukaryotes differ by at least about 50% at the nucleic acid level. More preferably the genetic sequences of the prokaryote or compact eukaryotes differ by at least about 70% at the nucleic acid level, or more preferably at least about 80% at the nucleic acid level or 90% at the nucleic acid level.

In determining whether or not two nucleotide sequences fall within these defined percentage identity limits, those skilled in the art will be aware that it is possible to conduct a side-by-side comparison of the nucleotide sequences. In such comparisons or alignments, differences will arise in the positioning of non-identical residues depending upon the algorithm used to perform the alignment. In the present context, references to percentage identities and similarities between two or more nucleotide sequences shall be taken to refer to the number of identical and similar residues respectively, between said sequences as determined using any standard algorithm known to those skilled in the art. In particular, nucleotide identities and similarities are calculated using software of the Computer Genetics Group, Inc., University Research Park, Maddison, Wis., United States of America, eg., using the GAP program of Devereaux et al., *Nucl. Acids Res.* 12, 387-395, 1984, which utilizes the algorithm of Needleman and Wunsch, *J. Mol. Biol.* 48, 443-453, 1970. Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment. Nucleotide sequence alignments can also be performed using a variety of other commercially available sequence analysis programs, such as, for example, the BLAST program available at NCBI.

In an alternative embodiment, the genetic sequences of the prokaryotes or compact eukaryotes fail to cross hybridize in a standard Cot analysis. The skilled artisan will be aware that standard Cot analyzes determine the similarity between two nucleotide sequences at the nucleotide level by using renaturation-kinetics of the corresponding nucleic acids (eg., Britten and Kohne *Science,* 161, 529-540, 1968).

Where more than one substantially sequenced genome used to produce the expression library of the present invention, it is also preferred that the fragments from each distinct prokaryote or compact eukaryote are used in an amount proportional to the complexity and size of the genome of said prokaryote or compact eukaryote. As the genomes of the prokaryotes and/or compact eukaryotes are substantially sequenced the approximate size of said genome's is determined. Accordingly, library is normalized to ensure that the amount of nucleic acids from all of the incorporated genomes to the final expression library is equal. In a particularly preferred embodiment, the nucleic acid fragment expression libraries are normalized such that nucleic acid fragments from each of the prokaryotes or compact eukaryotes are incorporated in equimolar amounts. In one exemplified embodiment, the sizes (in Mbp or molecular weight) of the genomes to be used in the expression library are compared and nucleic acid from each genome is used in an amount that is proportional to the ration of genome size to the size of the smallest contributing genome for the library. For example, the genome of *T. rubripes* is about 400 Mb in size, compared to the genome of *A. thaliana*, which is only about 120 Mb. Accordingly, for a combination of genomic *T. rubripes* and *A. thaliana* nucleic acid fragments, the ration of *T. rubripes* nucleic acid fragments to *A. thaliana* nucleic acid fragments would be about 4:1.2 (w/w). The relative contributions of nucleic acid fragments for constructing expression libraries from multiple genomes are readily calculated from the information presented in Table 1.

TABLE 1

Sizes of genomes of organisms from which nucleic acid fragments are derived for construction of expression libraries

| Source of nucleic acid fragments | Approx. genome size (Mb) |
| --- | --- |
| *Aeropyrum pernix* | 1.6–1.7 |
| *Agrobacterium pernix* | 1.67 |
| *Anopheles gambiae* | 26–27 |
| *Arabidopsis thaliana* | 120 |
| *Aquifex aeolicus* | 1.5–1.6 |
| *Archaeoglobus fulgidis* | 1.7 |
| *Bacillus subtilis* | 4.2 |
| *Bordetella pertussis* | 3.91 |
| *Borellia afzelii* | 0.95 |
| *Borellia garinii* | 0.95 |
| *Borrelia burgdorferi* | 0.91–0.96 |
| *Brugia malayi* | 100 |
| *Brucella suis* | 3.29 |
| *Buchnera sp.* | 0.64 |
| *Caenorhabditis elegans* | 97–102 |
| *Campylobacter jejuni* | 1.64 |
| *Caulobacter crescentus* | 4.01 |
| *Chlamydia muridarum* | 1.07 |
| *Chlamydia pneumoniae* | 1.22 |
| *Chlamydia trachomatis* | 1.0–1.1 |
| *Chlorobium tepidum* | 2.10 |
| *Chlostridium acetobutylicum* | 4.1 |
| *Danio rerio* | 1700 |
| *Deinococcus radiodurans* | 3.28 |
| *Drosophila melanogaster* | 120 |
| *Eimeria acervulina* | 70 |
| *Eimeria tenella* | 70 |
| *Entamoeba hystolitica* | 40 |
| *Escherichia coli* | 4.6–5.6 |

TABLE 1-continued

Sizes of genomes of organisms from which nucleic acid fragments are derived for construction of expression libraries

| Source of nucleic acid fragments | Approx. genome size (Mb) |
|---|---|
| Haemophilus influenzae | 1.83 |
| Halobacterium sp. | 2.57 |
| Helicobacter pylori | 1.66 |
| Lactococcus lactus | 2.36 |
| Listeria innocua | 3.01 |
| Listeria monocytogenes | 2.94 |
| Mesorhizobium loti | 7.59 |
| Methanobacterium thermoautotrophicum | 1.75 |
| Methanococcus jannaschii | 1.66 |
| Mycobacterium leprae | 2.8 |
| Mycobacterium tuberculosis | 4.4 |
| Mycoplasma genitalium | .58 |
| Mycoplasma penetrans | 1.36 |
| Mycoplasma pneumoniae | 0.81 |
| Mycoplasma pulmonis | 0.96 |
| Neisseria meningitidis | 2.18–2.27 |
| Oceanobacillus iheyensis | 3.6 |
| Oryza sativa | 400 |
| Pasturella multocida | 2.4 |
| Plasmodium berghei | 25 |
| Plasmodium falciparum | 25 |
| Plasmodium yoelii | 23 |
| Plasmodium vivax | 30 |
| Pseudomonas aeruginosa | 6.3 |
| Pseudomonas putida | 6.1 |
| Pyrococcus horikoshii | 1.74 |
| Ricketsia prowazekii | 1.1 |
| Saccharomyces cerevesiae | 13.0 |
| Salmonella typhi | 4.8 |
| Salmonella typhimurium | 4.8 |
| Sarcocystis cruzi | 201 |
| Schizosaccharomyces pombe | 13.8–14.0 |
| Schistosoma mansoni | 270 |
| Shewanalla oneidensis | 5.14 |
| Shigella flexneri | 4.7 |
| Sinorhizobium meliloti | 6.7 |
| Staphylococcu aureus | 2.8 |
| Streptococcus agalactiae | 2.21 |
| Streptococcus mutans | 2.03 |
| Streptococcus pneumoniae | 2.2 |
| Streptococcus pyogenes | 1.85 |
| Streptomyces avermitilis | 9 |
| Streptomyces coelicolor | 8.7 |
| Sulfolobus solfataricus | 2.99 |
| Sulfolobus tokodaii | 2.81 |
| Synechocystis PCC 6803 | 3.57 |
| Takifugu rubripes | 400 |
| Thermoplasma volcanium | 1.56–1.58 |
| Thermoanaerobacter tengcongensis | 2.69 |
| Thermoplasma acidophilum | 1.56 |
| Thermoplasma volcanium | 1.58 |
| Thermotoga maritima | 1.80 |
| Thermotoga pallidum | 1.14 |
| Toxoplasma gondii | 89 |
| Trypanosoma brucei | 35 |
| Trypanosoma cruzi | 40 |
| Ureaplasma urealyticum | 0.75 |
| Vibrio cholerae | 4 |
| Xanthomonas axonopodis | 5.17 |
| Xanthomonas campestris | 5.07 |
| Xylella fastidiosa | 2.68 |
| Yersinia pestis | 4.65 |

Preferred combinations of genomes are selected from the group consisting of:

a) nucleic acid fragments derived from two organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis PCC 6803, Takifugu rubripes, Thermoplasma volcanium,* and *Thermotoga maritima;* b) nucleic acid fragments derived from three organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis PCC 6803, Takifugu rubripes, Thermoplasma volcanium,* and *Thermotoga maritima;* c) nucleic acid fragments derived from four organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis PCC 6803, Takifugu rubripes, Thermoplasma volcanium,* and *Thermotoga maritima;* d) nucleic acid fragments derived from five organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis PCC 6803, Takifugu rubripes, Thermoplasma volcanium,* and *Thermotoga maritima;* e) nucleic acid fragments derived from six organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis PCC 6803, Takifugu rubripes, Thermoplasma volcanium,* and *Thermotoga maritima;* f) nucleic acid fragments derived from seven organisms selected from the group consisting of: *Aeropyrum pernix, Anopheles gambiae, Arabidopsis thaliana, Aquifex aeoli-* cus, *Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* g) nucleic acid fragments derived from eight organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* h) nucleic acid fragments derived from nine organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* i) nucleic acid fragments derived from ten organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* j) nucleic acid fragments derived from eleven organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* k) nucleic acid fragments derived from twelve organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* l) nucleic acid fragments derived from thirteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* m) nucleic acid fragments derived from fourteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* n) nucleic acid fragments derived from fifteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* o) nucleic acid fragments derived from sixteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cer-* evesiae, Schizosaccharomyces pombe, Synechocystis PCC 6803, *Takifugu rubripes, Thermoplasma volcanium,* and *Thermotoga maritima;* p) nucleic acid fragments derived from seventeen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and Thermotoga maritima;

q) nucleic acid fragments derived from eighteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* r) nucleic acid fragments derived from nineteen organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* s) nucleic acid fragments derived from twenty organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* t) nucleic acid fragments derived from twenty one organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* u) nucleic acid fragments derived from twenty two organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* v) nucleic acid fragments derived from twenty three organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* w) nucleic acid fragments derived from twenty four organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* x) nucleic acid fragments derived from twenty five organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* y) nucleic acid fragments derived from twenty six organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans,*

*Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima;* and z) nucleic acid fragments derived from twenty seven organisms selected from the group consisting of: *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima.*

In a particularly preferred embodiment, the nucleic acid fragments are derived from the organisms *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Saccharomyces cerevesiae, Schizosaccharomyces pombe, Synechocystis* PCC 6803, *Takifugu rubripes, Thermoplasma volcanium,* and *Thermotoga maritima.*

In a particularly preferred embodiment, nucleic acid fragments derived from the following bacteria are combined into a single expression library: *Aeropyrum pernix, Aquifex aeolicus, Archaeoglobus fulgidis, Bacillus subtilis, Bordetella pertussis, Borrelia burgdorferi, Chlamydia trachomatis, Escherichia coli, Haemophilus influenzae, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima.*

The nucleic acid fragments, unmodified or modified by the addition of one or more linkers, adaptors, Kozak containing oligonucleotides, Kozak containing fragments, or nucleic acids comprising a sequence that confers transcriptional or translational slippage, are placed in operable connection with a promoter sequence, thereby producing a recombinant gene construct.

The term "gene construct" is to be taken in its broadest context and includes a promoter sequence that is placed in operable connection with a nucleic acid fragment of the present invention. The nucleic acid comprising the promoter sequence is isolated using techniques well known in the art, such as for example PCR or restriction digestion. Alternatively the nucleic acid comprising the promoter sequence is synthetic, that is an oligonucleotide. The methods of producing oligonucleotides are well known in the art and are described, for example, in Oligonucleotide Synthesis: A Practical Approach (M. J. Gait, ed., 1984) IRL Press, Oxford, whole of text, and particularly the papers therein by Gait, pp1-22; Atkinson et al., pp35-81; Sproat et al., pp 83-115; and Wu et al., pp 135-151.

The term "promoter" is to be taken in its broadest context and includes the transcriptional regulatory sequences of a genomic gene, including the TATA box or initiator element, which is required for accurate transcription initiation, with or without additional regulatory elements (ie. upstream activating sequences, transcription factor binding sites, enhancers and silencers) which alter gene expression in response to developmental and/or external stimuli, or in a tissue specific manner. In the present context, the term "promoter" is also used to describe a recombinant, synthetic or fusion molecule, or derivative which confers, activates or enhances the expression of a nucleic acid molecule to which it is operably linked, and which encodes the peptide or protein. Preferred promoters can contain additional copies of one or more specific regulatory elements to further enhance expression and/or alter the spatial expression and/or temporal expression of said nucleic acid molecule.

Placing a nucleic acid molecule under the regulatory control of, ie., "in operable connection with", a promoter sequence means positioning said molecule such that expression is controlled by the promoter sequence. Promoters are generally positioned 5' (upstream) to the coding sequence that they control. To construct heterologous promoter/structural gene combinations, it is generally preferred to position the promoter at a distance from the gene transcription start site that is approximately the same as the distance between that promoter and the gene it controls in its natural setting, ie., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, ie., the gene from which it is derived. Again, as is known in the art, some variation in this distance can also occur.

Typical promoters suitable for expression in viruses of bacterial cells and bacterial cells such as for example a bacterial cell selected from the group comprising *E. coli, Staphylococcus* sp, *Corynebacterium* sp., *Salmonella* sp., *Bacillus* sp., and *Pseudomonas* sp., include, but are not limited to, the lacz promoter, the Ipp promoter, temperature-sensitive $\lambda_L$ or $\lambda_R$ promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, N.Y., Third Edition 2001).

Typical promoters suitable for expression in yeast cells such as for example a yeast cell selected from the group comprising *Pichia pastoris, S. cerevisiae* and *S. pombe,* include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Typical promoters suitable for expression in insect cells, or in insects, include, but are not limited to, the OPEI2 promoter, the insect actin promoter isolated from Bombyx muri, the *Drosophila* sp. dsh promoter (Marsh et al *Hum. Mol. Genet.* 9, 13-25, 2000) and the inducible metallothionein promoter. Preferred insect cells for expression of the recombinant polypeptides include an insect cell selected from the group comprising, BT1-TN-5B1-4 cells, and *Spodoptera frugiperda* cells (eg., sf19 cells, sf21 cells). Suitable insects for the expression of the nucleic acid fragments include but are not limited to *Drosophila* sp. The use of *S. frugiperda* is also contemplated.

Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

Typical promoters suitable for expression in a virus of a mammalian cell, or in a mammalian cell, mammalian tissue or intact mammal include, for example a promoter selected from the group consisting of, retroviral LTR elements, the SV40 early promoter, the SV40 late promoter, the cytomegalovirus (CMV) promoter, the CMV IE (cytomegalovirus immediate early) promoter, the $EF_{1\alpha}$ promoter (from human elongation factor 1α), the EM7 promoter, the UbC promoter (from human ubiquitin C).

Preferred mammalian cells for expression of the nucleic acid fragments include epithelial cells, fibroblasts, kidney cells, T cells, or erythroid cells, including a cell line selected from the group consisting of COS, CHO, murine 10T, MEF, NIH3T3, MDA-MB-231, MDCK, HeLa, K562, HEK 293 and 293T. The use of neoplastic cells, such as, for example, leukemic/leukemia cells, is also contemplated herein.

Preferred mammals for expression of the nucleic acid fragments include, but are not limited to mice (ie., *Mus* sp.) and rats (ie., *Rattus* sp.).

In one embodiment, nucleic acid comprising a promoter sequence is ligated to a nucleic acid fragment from the prokaryote or compact eukaryote, or a modified form thereof, using techniques well known in the art.

In another embodiment, nucleic acid comprising a promoter sequence is modified by the addition of one or more linkers, adaptors, Kozak containing oligonucleotides, Kozak containing fragments, or nucleic acids comprising a sequence that confers transcriptional or translational slippage and ligated to a nucleic acid fragment from the prokaryote or compact eukaryote using techniques well known in the art.

In yet another embodiment, nucleic acid comprising a promoter sequence is incorporated into an oligonucleotide with or without another nucleic acid comprising one or more spacers, Kozak sequences, or nucleic acids comprising a sequence that confers transcriptional or translational slippage.

Preferably, the oligonucleotide comprises a nucleotide sequence that is complementary or homologous to a region flanking the nucleic acid fragment from the prokaryote or compact eukaryote, such as, for example, an adaptor. Such a complementary or homologous sequence permits oligonucleotide primers to be used for amplifying nucleic acid comprising a promoter region and means for ribosome binding (such as for example a Kozak sequence or Shine-Dalgarno sequence) and the nucleic acid fragment as a single fragment. In this manner, a gene construct comprising a promoter sequence, means for ribosome binding and a nucleic acid fragment is readily constructed using the amplified nucleic acid.

In an alternative embodiment, a nucleic acid comprising a promoter sequence is incorporated into an oligonucleotide with or without another nucleic acid comprising one or more spacers, Kozak sequences, or nucleic acids comprising a sequence that confers transcriptional or translational slippage, and said oligonucleotide is operably linked to a nucleic acid fragment of the present invention by, for example, ligation.

As will be known to the skilled artisan, the promoter is also be positioned in the expression vector or gene construct into which the prokaryote or eukaryote nucleic acid fragment is inserted.

In one embodiment, the nucleic acid fragments are expressed in vitro. According to this embodiment, the gene construct preferably comprises a nucleic acid fragment of the prokaryote or compact eukaryote, and a promoter sequence and appropriate ribosome binding site which is both be present in the expression vector or added to said nucleic acid fragment before it is inserted into the vector. Typical promoters for the in vitro expression of the nucleic acid fragments of the present invention include, but are not limited to the T3 or T7 (Hanes and Plückthun *Proc. Natl. Acad. Sci. USA,* 94 4937-4942 1997) bacteriophage promoters.

In another embodiment, the gene construct optionally comprises a transcriptional termination site and/or a translational termination codon. Such sequences are well known in the art, and is incorporated into oligonucleotides used to amplify the nucleic acid fragment of the prokaryote or compact eukaryote, or alternatively, present in the expression vector or gene construct before the nucleic acid fragment is inserted.

In another embodiment, the gene construct is an expression vector. The term "expression vector" refers to a nucleic acid molecule that has the ability confer expression of a nucleic acid fragment to which it is operably connected, in a cell or in a cell free expression system. Within the context of the present invention, it is to be understood that an expression vector may comprise a promoter as defined herein, a plasmid, bacteriophage, phagemid, cosmid, virus sub-genomic or genomic fragment, or other nucleic acid capable of maintaining and or replicating heterologous DNA in an expressible format. Many expression vectors are commercially available for expression in a variety of cells. Selection of appropriate vectors is within the knowledge of those having skill in the art.

Typical expression vectors for in vitro expression or cell-free expression have been described and include, but are not limited to the TNT T7 and TNT T3 systems (Promega), the pEXP1-DEST and pEXP2-DEST vectors (Invitrogen).

Numerous expression vectors for expression of recombinant polypeptides in bacterial cells and efficient ribosome binding sites have been described, such as for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT,USA); the pQE series of expression vectors (QIAGEN, CA, USA), or the pL series of expression vectors (Invitrogen), amongst others.

Expression vectors for expression in yeast cells are preferred and include, but are not limited to, the pACT vector (Clontech), the pDBleu-X vector, the pPIC vector suite (Invitrogen), the pGAPZ vector suite (Invitrogen), the pHYB vector (Invitrogen), the pYD1 vector (Invitrogen), and the pNMT1, pNMT41, pNMT81 TOPO vectors (Invitrogen), the pPC86-Y vector (Invitrogen), the pRH series of vectors (Invitrogen), pYESTrp series of vectors (Invitrogen). Particularly preferred vectors are the pACT vector, pDBleu-X vector, the pHYB vector, the pPC86 vector, the pRH vector and the pYES vectors, which are all of use in various 'n'-hybrid assays described herein. Furthermore, the pYD1vector is particularly useful in yeast display experiments in *S. cerevesiae*. A number of other gene construct systems for expressing the nucleic acid fragment of the invention in yeast cells are well-known in the art and are described for example, in Giga-Hama and Kumagai (In: Foreign Gene Expression in Fission Yeast: *Schizosaccharomyces Pombe*, Springer Verlag, ISBN 3540632700, 1997) and Guthrie and Fink (In: Guide to Yeast Genetics and Molecular and Cell Biology Academic Press, ISBN 0121822540, 2002).

A variety of suitable expression vectors, containing suitable promoters and regulatory sequences for expression in insect cells are well known in the art, and include, but are not limited to, the pAC5 vector, the pDS47 vector, the pMT vector suite (Invitrogen) and the pIB vector suite (Invitrogen).

Furthermore, expression vectors comprising promoters and regulatory sequences for expression of polypeptides in plant cells are also well known in the art and include, for example, a promoter selected from the group, pSS, pB1121 (Clontech), pZ01502, and pPCV701 (Kuncz et al, *Proc. Natl. Acad. Sci. USA*, 84 131-135, 1987).

Expression vectors that contain suitable promoter sequences for expression in mammalian cells or mammals include, but are not limited to, the pcDNA vector suite supplied by Invitrogen, the pCI vector suite (Promega), the pCMV vector suite (Clontech), the pM vector (Clontech), the pSI vector (Promega), the VP16 vector (Clontech) and the pDISPLAY vectors (Invitrogen). The pDISPLAY vectors are of particular use in mammalian display studies with the expressed nucleic acid fragment targeted to the cell surface with the Igκ leader sequence, and bound to the membrane of the cell through fusion to the PDGFR transmembrane domain. The pM and VP16 vectors are of particular use in mammalian two-hybrid studies.

Methods of cloning DNA into nucleic acid vectors for expression of encoded polypeptides are well known in the art and are described for example in, Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

The nucleic acid fragments of the present invention is also be expressed in the cells of other organisms, or entire organisms including, for example, nematodes (eg *C. elegans*) and fish (eg *D. rerio*, and *T. rubripes*). Promoters for use in nematodes include, but are not limited to osm-10 (Faber et al *Proc. Natl. Acad. Sci. USA* 96, 179-184, 1999), unc-54 and myo-2 (Satyal et al *Proc. Natl. Acad. Sci. USA*, 97 5750-5755, 2000). Promoters for use in fish include, but are not limited to the zebrafish OMP promoter, the GAP43 promoter, and serotonin-N-acetyl transferase gene regulatory regions.

In a preferred embodiment, the expression library of the present invention is transcribed and translated in vitro. Methods of transcribing nucleic acid fragments and translating the resulting mRNA are well known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001), for example the use of *E. coli* S30 lysate (available in kit for from Promega).

In a preferred embodiment the gene construct contains a second nucleic acid in operable connection with a nucleic acid fragment of the present invention. This second nucleic acid encodes a fusion partner. As used herein the term "fusion partner" shall be understood to mean a polypeptide sequence that is associated with a peptide encoded by a nucleic acid fragment of the present invention. Such a fusion partner confers a common function or ability upon all polypeptides encoded by the expression library. Suitable fusion partners include, but are not limited to, presentation structures, polypeptides that facilitate the uptake of peptides into target cells, polypeptides that cause nuclear localisation, polypeptides that cause secretion, polypeptides that cause mitochondrial localisation, polypeptides that cause membrane localisation, or a combination of any of these sequences.

Without suggesting that such a process is essential to the invention, a peptide encoded by the expression library of the present invention can also be expressed such that it is conformationally constrained, or expressed in a "presentation structure". Such constraint, whilst not generally necessary for expressing protein domains or peptides having a conformation sufficient to bind to a target protein or target nucleic acid, is useful for displaying peptides that comprise more highly flexible sequences, or to enhance stability against proteolytic enzymes (Humphrey et al, *Chem Rev* 97, 2243-2266, 1997).

A presentation structure will generally comprise a first component, ie. polypeptide, that is fused to the amino terminus of the polypeptide and a second component fused to the carboxyl-terminus of the peptide. Examples of such presentation structures include, but are not limited to, cysteine-linked (disulfide) structures, zinc-finger domains, cyclic peptides, and transglutaminase linked structures.

In a preferred embodiment, the presentation structure is a sequence that contains at least two cysteine residues, such that a disulphide bond is formed between the cysteine residues, resulting in a conformationally constrained peptide.

In another embodiment, a peptide encoded by an expression library of the present invention is expressed within a second polypeptide as a fusion protein. Polypeptides used for such purposes are capable of reducing the flexibility of another protein's amino and/or carboxyl termini. Preferably, such proteins provide a rigid scaffold or platform for the protein. In addition, such proteins preferably are capable of providing protection from proteolytic degradation and the like, and/or are capable of enhancing solubility. Preferably, conformation-constraining proteins are small in size (generally, less than or equal to about 200 amino acids in length), rigid in structure, of known three-dimensional configuration, and are able to accommodate insertions of proteins without undue disruption of their structures. A key feature of such proteins is the availability, on their solvent exposed surfaces, of locations where peptide insertions can be made (eg., the Trx loop). It is also preferable that conformation-constraining protein producing genes be highly expressible in various prokaryotic and eukaryotic hosts, or in suitable cell-free systems, and that the proteins be soluble and resistant to protease degradation.

Examples of conformation-constraining proteins include the active site of thioredoxin or Trx loop and other thioredoxin-like proteins, nucleases (eg., RNase A), proteases (eg., trypsin), protease inhibitors (eg., bovine pancreatic trypsin inhibitor), antibodies or structurally rigid fragments thereof, conotoxins, and the pleckstrin homology domain. A conformation-constraining peptide can be of any appropriate length and can even be a single amino acid residue.

This technique has been successfully used for bacterial display of peptides in bacteria using a Trx scaffold (Blum et al *Proc. Natl. Acad. Sci. USA* 97, 2241-2246 2000) in addition to the use in yeast 2 hybrid screening using either a catalytically inactive form of staphylococcal nuclease, or Trx (Norman et al, *Science*,285, 591-595, 1999; and Colas et al, *Nature* 380, 548-550, 1996).

In another embodiment the expression vector or gene construct is optionally comprise a transcriptional terminator that is operative in the expression system. Furthermore, the gene construct is also comprise a nucleic acid comprising the sequence of a polyadenylation signal operative in the expression system.

It is preferred that when the gene constructs are to be introduced to and/or maintained and/or propagated and/or expressed in bacterial cells, either during generation of said gene constructs, or screening of said gene constructs, that the gene constructs contain an origin of replication that is operable at least in a bacterial cell. A particularly preferred origin of replication is the ColE1 origin of replication. A number of gene construct systems containing origins of replication are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001).

It is also preferred that when the gene constructs are to be introduced to and/or maintained and/or propagated and/or expressed in yeast cells, either during generation of said gene constructs, or screening of said gene constructs, that the gene constructs contain an origin of replication that is operable at least in a yeast cell. One preferred origin of replication is the CEN/ARS4 origin of replication. Another particularly preferred origin of replication is the 2-micron origin of replication. A number of gene construct systems containing origins of replication are well-known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

In another embodiment, the gene construct containing the nucleic acid fragments of the present invention comprise another nucleic acid cassette comprising a promoter sequence in operable connection with a polynucleotide sequence encoding a selectable marker.

As used herein the term "selectable marker" shall be taken to mean a protein or peptide that confers a phenotype on a cell expressing said selectable marker that is not shown by those cells that do not carry said selectable marker. Examples of selectable markers include, but are not limited to the dhfr resistance gene, which confers resistance to methotrexate (Wigler, et al., 1980, Natl. Acad. Sci. USA 77:3567; O'Hare, et al., 1981, Proc. Natl. Acad. Sci. USA 78:1527); the gpt resistance gene, which confers resistance to mycophenolic acid (Mulligan & Berg, 1981, Proc. Natl. Acad. Sci. USA 78:2072); the neomycin phosphotransferase gene, which confers resistance to the aminoglycoside G-418 (Colberre-Garapin, et al., 1981, J. Mol. Biol. 150:1); and the hygromycin resistance gene (Santerre, et al., 1984, Gene 30:147). Alternatively, marker genes is catalyse reactions resulting in a visible outcome (for example the production of a blue color when β galactosidase is expressed in the presence of the substrate molecule 5-bromo-4-chloro-3-indoyl-β-D-galactoside) or confer the ability to synthesise particular amino acids (for example the HIS3 gene confers the ability to synthesize histidine).

In one embodiment the peptide encoded by the nucleic acid fragment of the present invention is expressed as a fusion protein with a peptide sequence capable of enhancing, increasing or assisting penetration or uptake of the peptide by cells either in vitro or in vivo. For example, the peptide sequence capable of enhancing, increasing or assisting penetration or uptake is the *Drosophila* penetratin targeting sequence. This peptide sequence at least comprises the amino acid sequence:

CysArgGlnIleLysIleTrpPheGlnA-snArgArgMetLysTrpLysLys (SEQ ID NO. 29) further comprising (Xaa)n after the final Lys residue and followed by Cys wherein Xaa is any amino acid and n has a value greater than or equal to 1. Alternatively, a homologue, derivative or analogue of said sequence is used. The use of said sequence is particularly useful when peptides encoded by the nucleic acid fragment of the present invention are synthesised in vitro or secreted from a host cell, and must be taken up by a cell for screening said peptide encoded by the nucleic acid fragment of the present invention.

Those skilled in the art will also be aware of an analogous use of signals such as for example, the tat sequence of HIV to drive import of peptides into cells.

In an alternative embodiment, the peptide encoded by the nucleic acid fragment of the present invention is mixed with a peptide capable of enhancing, increasing or assisting penetration or uptake by cells in vitro or in vivo. A peptide sequence that is able to increase or assist penetration or uptake of cells is the synthetic peptide Pep 1, which at least comprises the amino acid sequence:

LysGluThrTrpTrpGluThrTrp-
TrpThrGluTrpSerGlnLysLysLysLysArgLysVal
(SEQ ID NO. 30).

The Pep1 peptide does not need to be conjugated to the peptide encoded by the nucleic acid fragments of the present invention. Furthermore, Pep1 dissociates from the peptide encoded by the expression library of the present invention. Thus Pep1 will not interfere with the peptide forming a conformation sufficient for binding to a target protein or nucleic acid. Pep1 is only useful when the peptides encoded by the expression library of the present invention are isolated prior to the addition to a cell or organism for screening. Thus Pep1 is particularly useful when in vitro libraries are screened.

In one embodiment, the expression library of the present invention are introduced to and preferably expressed within a cellular host or organism to generate the expression library, it is preferred that the gene constructs are introduced into said cellular host or said organism. Methods of introducing the gene constructs into a cell or organism for expression are well known to those skilled in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001). The method chosen to introduce the gene construct in depends upon the cell type in which the gene construct is to be expressed.

In one embodiment, the cellular host is a bacterial cell. Means for introducing recombinant DNA into bacterial cells include, but are not limited to electroporation or chemical transformation into cells previously treated to allow for said transformation.

In another embodiment, the cellular host is a yeast cell. Means for introducing recombinant DNA into yeast cells include a method chosen from the group consisting of electroporation, and PEG mediated transformation.

In another embodiment, the cellular host is a plant cell. Means for introducing recombinant DNA into plant cells include a method selected from the group consisting of *Agrobacterium* mediated transformation, electroporation of protoplasts, PEG mediated transformation of protoplasts, particle mediated bombardment of plant tissues, and microinjection of plant cells or protoplasts.

In yet another embodiment, the cellular host is an insect cell. Means for introducing recombinant DNA into plant cells include a method chosen from the group consisting of, infection with baculovirus and transfection mediated with liposomes such as by using cellfectin (Invitrogen).

In yet another embodiment, the cellular host is a mammalian cell. Means for introducing recombinant DNA into mammalian cells include a means selected from the group comprising microinjection, transfection mediated by DEAE-dextran, transfection mediated by calcium phosphate, transfection mediated by liposomes such as by using Lipofectamine (Invitrogen) and/or cellfectin (Invitrogen), PEG mediated DNA uptake, electroporation, transduction by Adenoviuses, Herpesviruses, Togaviruses or Retroviruses and microparticle bombardment such as by using DNA-coated tungsten or gold particles (Agacetus Inc., WI, USA).

In an alternative embodiment, the expression library is an in vitro display library (ie., the peptides encoded by the prokaryote or compact eukaryote nucleic acid fragments of the expression library are displayed using in vitro display wherein the expressed peptide is linked to the nucleic acid from which it was expressed such that said peptide is presented in the absence of a host cell). Accordingly, expression libraries produced by in vitro display technologies are not limited by transformation or transfection efficiencies. Accordingly any such library is of much higher complexity than an in vivo display library. Examples of methods of in vitro display include a method selected from the group comprising but not limited to, ribosome display, covalent display and mRNA display.

In one embodiment, the in vitro display library is a ribosome display library. The skilled artisan will be aware that a ribosome display library directly links mRNA encoded by the expression library to the peptide that it encodes. Means for producing a ribosome display library require that the nucleic acid fragment be placed in operable connection with an appropriate promoter sequence and ribosome binding sequence, ie. form a gene construct. Preferred promoter sequences are the bacteriophage T3 and T7 promoters.

Preferably, the nucleic acid fragment is placed in operable connection with a spacer sequence and a modified terminator sequence with the terminator sequence removed.

As used herein the term "spacer sequence" shall be understood to mean a series of nucleic acids that encode a peptide that is fused to the peptide. The spacer sequence is incorporated into the gene construct, as the peptide encoded by the spacer sequence remains within the ribosomal tunnel following translation, while allowing the peptide to freely fold and interact with another protein or a nucleic acid.

A preferred spacer sequence is, for example, a nucleic acid that encodes amino acids 211-299 of gene III of filamentous phage M13 mp19.

The display library is transcribed and translated in vitro using methods well known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Examples of systems for in vitro transcription and translation include, for example, the TNT in vitro transcription and translation systems from Promega. Cooling the expression reactions on ice generally terminates translation. The ribosome complexes are stabilized against dissociation from the peptide and/or its encoding mRNA by the addition of reagents such as, for example, magnesium acetate or chloroamphenicol. Such in vitro display libraries are screened by a variety of methods, as described herein.

In another embodiment, the expression library of the present invention is a ribosome inactivation display library. In accordance with this embodiment, a nucleic acid fragment is operably linked to a nucleic acid encoding a first spacer sequence. It is preferred that this spacer sequence is a glycine/serine rich sequence that allows a peptide encoded by the expression library of the present invention to freely fold and interact with a target protein or nucleic acid.

The first spacer sequence is linked to a nucleic acid that encodes a toxin that inactivates a ribosome. It is preferred that the toxin comprises the ricin A chain, which inactivates eukaryotic ribosomes and stalls the ribosome on the translation complex without release of the mRNA or the encoded peptide.

The nucleic acid encoding the toxin is linked to another nucleic acid that encodes a second spacer sequence. The second spacer is required as an anchor to occupy the tunnel of the ribosome, and allow both the peptide and the toxin to correctly fold and become active. Examples of such spacer sequences are sequences derived from gene III of M13 bacteriophage.

Ribosome inactivation display libraries are generally transcribed and translated in vitro, using a system such as the rabbit reticulocyte lysate system available from Promega. Upon translation of the mRNA encoding the toxin and correct folding of this protein, the ribosome is inactivated while still bound to both the encoded polypeptide and the mRNA from which it was translated.

In another embodiment, the expression library of the present invention is an mRNA display library. In accordance with this embodiment, a nucleic acid fragment is operably linked to a nucleic acid encoding a spacer sequence, such as a glycine/serine rich sequence that allows a peptide encoded by the expression library of the present invention to freely fold and interact with a target protein or nucleic acid.

The nucleic acid encoding the spacer sequence is operably linked to a transcription terminator.

mRNA display libraries are generally transcribed in vitro, using methods well known in the art, such as, for example, the HeLaScribe Nuclear Extract in vitro Transcription System available from Promega. Encoded mRNA is subsequently covalently linked to a DNA oligonucleotide that is covalently linked to a molecule that binds to a ribosome, such as, for example, puromycin, using techniques well known in the art and are described in, for example, Roberts and Szostak, *Proc. Natl. Acad. Sci. USA*, 94, 12297-12302 (1997). Preferably, the oligonucleotide is covalently linked to a psoralen moiety, whereby the oligonucleotide is photo-crosslinked to a mRNA encoded by the expression library of the present invention.

The mRNA transcribed from the expression library is then translated using methods well known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001). When the ribosome reaches the Junction of the mRNA and the oligonucleotide the ribosome stalls and the puromycin moiety enters the phosphotransferase site of the ribosome and thus covalently links the encoded polypeptide to the mRNA from which it was expressed.

In yet another embodiment, the expression library of the present invention is a covalent display library. In accordance with this embodiment, the nucleic acid fragment is operably linked to a second nucleic acid fragment that encodes a protein that interacts with the DNA from which it was encoded. Examples of a protein that interacts with the DNA from which it interacts include, but are not limited to, the *E. coli* bacteriophage P2 viral A protein (P2A) and equivalent proteins isolated from phage 186, HP1 and PSP3.

The P2A protein is particularly preferred. The P2A protein recognizes a defined initiator sequence TCGGA (SEQ ID NO 31) positioned within the nucleic acid encoding the P2A protein and nicks one of the strands while forming a covalent bond with one of the free end nucleotides. Accordingly, it is preferred that at least the sequence TCGGA (SEQ ID NO 31) is included in the gene construct containing the expression library of the present invention.

It is particularly preferred that the protein attachment site is positioned such that a nucleic acid fragment is covalently linked to the peptide that it encodes.

A covalent display gene construct is transcribed and translated in vitro, using a system such as the rabbit reticulocyte lysate system available from Promega. Upon translation of the fusion of the peptide and the P2A protein, the P2A protein nicks the nucleic acid of the sequence of SEQ ID NO: 31 and forms a covalent bond therewith. Accordingly, a nucleic acid fragment is covalently linked to the peptide that it encodes.

In yet another embodiment, the expression library is a phage display library wherein the expressed peptides or protein domains are displayed on the surface of a bacteriophage, as described, for example, in U.S. Pat. Nos. 5,821,047 and 6,190,908. The basic principle described relates to the fusion of a first nucleic acid comprising a sequence encoding a peptide or protein to a second nucleic acid comprising a sequence encoding a phage coat protein, such as, for example a phage coat proteins selected from the group, M13 protein-3, M13 protein-7, or M13, protein-8. These sequences are then inserted into an appropriate vector, ie. one that is able to replicate in bacterial cells. Suitable host cells, such as, for example *E. coli*, are then transformed with the recombinant vector. Said host cells are also infected with a helper phage particle encoding an unmodified form of the coat protein to which a nucleic acid fragment is operably linked. Transformed, infected host cells are cultured under conditions suitable for forming recombinant phagemid particles comprising more than one copy of the fusion protein on the surface of the particle. This system has been shown to be effective in the generation of virus particles such as, for example, a virus particle selected from the group comprising λ phage, T4 phage, M13 phage, T7 phage and baculovirus. Such phage display particles are then screened to identify a displayed protein having a conformation sufficient for binding to a target protein or nucleic acid.

In yet another embodiment, the expression library is a retroviral display library wherein the expressed peptides or protein domains are displayed on the surface of a retroviral particle. Retroviral display is of particular use as the proteins and peptides displayed in such a system are generated in eukaryotic cells that can carry out a number of post-translational modifications to the peptides or protein domains that are required for activity. Such a retroviral display system is described in U.S. Pat. No. 6,297,004 (Cambridge Drug Discovery Holding, Limited). In adapting such a system to the present invention, a nucleic acid fragment is placed in operable connection with an envelope protein of a retrovirus, more preferably a spike glycoprotein. An example of such a protein is the mature envelope protein of Moloney Murine leukemia virus. A gene construct comprising a nucleic acid fragment of the present invention in operable connection with a retroviral envelope protein is also placed in operable connection with long terminal repeat sequences, a tRNA binding site and a polypurine tract to ensure reverse transcription and integration of the encapsid RNA in an infected mammalian cell. Furthermore, such a gene construct should comprise an encapsidated signal sequence. An encapsidated signal sequence is a nucleic acid that is recognised by a component of the viral particle that mediates the inclusion of the nucleic acid into the viral particle. Such a gene construct is then expressed in an appropriate host cell, such as, for example, a COS cell or NIH3T3 cell, that has been previously infected with a retrovirus encoding an unmodified spike glycoprotein. In such a system chimeric retroviral particles are generated, carrying a mixture of modified and unmodified forms of the spike glycoprotein. These recombinant retrovirus particles are used to identify a displayed peptide that binds to a target protein or nucleic acid.

In yet another embodiment, the expression library is a bacterial display library wherein the expressed peptides or protein domains are displayed on the surface of a bacterial cell. The cells displaying the expressed peptides or protein domains are then used for biopanning as described, for example, in U.S. Pat. No. 5,516,637. Bacterial display is based on the finding that heterologous proteins is expressed as a fusion with bacterial surface proteins and assayed for the ability to bind to a target protein or nucleic acid.

Accordingly, in such systems a nucleic acid fragment is placed in operable connection with a second nucleic acid that encodes an anchoring motif, or amino acid sequence that directs the incorporation of the encoded peptide on the surface of the bacterial cell surface. Preferred amino acid sequences that direct incorporation of a peptide onto the surface of a bacterial cell include, but are not limited to, the flagella major subedit FliC for localizing a protein on the flagellum of *E. coli*, the cell sorting signal of the cell wall proteinase PrtP of *Lactobacillus casei*, the OmpS maltoprotein of *Vibrio cholerae*, Protein A of *Bacillus subtilis*, LysA of *B. subtilis*, and ActA of *B. subtilis*. Expression libraries comprising such gene constructs are then introduced into an appropriate host cell, such as for example *E. coli* or *B. subtilis* and the expressed peptides displayed on the surface of the bacterial cell. Such displayed libraries are of particular use in screening for peptides that have a conformation sufficient for binding a target protein or nucleic acid.

In an alternative embodiment, the peptides encoded by the nucleic acid fragments of the present invention is also be fused to a second nucleic acid comprising a sequences that encodes a peptide that directs the incorporation of the encoded peptide on the surface of a bacterial spore. Such methods are particularly useful in the display of peptides that are toxic to bacteria when expressed intra cellularly, or when screening conditions are particularly harsh, such as, for example in the presence of organic solvents, or high temperatures.

In yet another embodiment, the expression library is a phage display library wherein the expressed peptides or protein domains are displayed on the surface of a yeast cell. This method is particularly useful for the display of peptides encoded by nucleic acid derived from eukaryotes, as prokaryotic species are unable to form some structures encoded by eukaryotic sequences. Such a yeast display method is described in U.S. Pat. No. 6,423,538. In adapting this method to the present invention, a nucleic acid fragment is operably linked to a second nucleic acid fragment encoding the membrane-associated alpha-agglutinin yeast adhesion receptor, encoded by the aga2 gene. The expression library is introduced into an appropriate host cell, such as for example S. cerevisiae or S. pombe. Following introduction into an appropriate host cell the fusion protein is secreted from the cell. The fusion protein then binds to the Aga1 protein on the surface of the cell by forming disulfide bonds. Such a yeast cell is screened to determine whether or not it expresses a peptide having a conformation sufficient for binding to a target protein or nucleic acid.

In yet another embodiment, the expression library is a phage display library wherein the expressed peptides or protein domains are displayed on the surface of a mammalian cell. Such a system is described for example in Strenglin et al EMBO J, 7, 1053-1059, 1988. Mammalian display is particularly useful for the display of peptides derived from eukaryotes, as prokaryotic species and some lower eukaryotic species are unable to form some structures encoded by eukaryotic sequences. The mechanism behind mammalian display relates to the fusion of a nucleic acid fragment to a second nucleotide sequence encoding a peptide leader sequence, which directs the protein to be secreted, such as for example the Ig κ secretion signal. Furthermore, the nucleic acid fragment is placed in operable connection with another nucleic acid, which encodes a peptide that anchors the peptide to the membrane, such as, for example the sequence PDGFR (SEQ ID NO: 32) which corresponds to a transmembrane domain. An example of a vector containing such a sequence is the pDISPLAY vector available from Invitrogen. Proteins expressed by such a vector are displayed upon the surface of the mammalian cell, making these cells particularly useful for screening for peptides that adopt a conformation sufficient for binding to a target protein or nucleic acid.

A second aspect of the present invention provides an expression library comprising nucleic acid fragments from two or more microorganisms or eukaryotes containing compact genomes, each of said microorganisms or eukaryotes having a substantially sequenced genome, wherein said nucleic acid fragments are inserted into a suitable expression construct thereby producing recombinant constructs, wherein each fragment is in operable connection with a promoter sequence that is capable of conferring expression of that fragment.

In a preferred embodiment, the present invention provides an expression library comprising nucleic acid fragments derived from two or more microorganisms or eukaryotes containing compact genomes, each of said microorganisms or eukaryotes having a substantially sequenced genome, wherein the fragments are inserted into a suitable expression vector in an amount proportional to the size of the genome from which the fragments were derived thereby producing recombinant constructs and wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library comprise an open reading frame having an average length of at least about 36-45 nucleotide residues and/or encode a protein domain, and wherein the nucleic acid fragments are inserted into a suitable expression vector thereby producing recombinant constructs wherein each fragment is in operable connection with a promoter sequence that is capable of conferring expression of that fragment.

In an alternative embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library comprise an open reading frame having an average length of at least about 36-45 nucleotide residues and/or encode a protein domain, and wherein the nucleic acid fragments are inserted into a suitable expression vector in an amount proportional to the size of the genome from which the fragments were derived thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and are inserted into a suitable expression vector thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and are inserted into a suitable expression vector in an amount proportional to the size of the genome from which the fragments were derived thereby producing recombinant constructs wherein each fragment is in operable connection with a promoter sequence that is capable of conferring expression of that fragment.

In a further preferred embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and comprise an open reading frame having an average length of at least about 36-45 nucleotide residues and/or encode a protein domain, and wherein the nucleic acid fragments are inserted into a suitable expression vector thereby producing recombinant constructs wherein each fragment is in operable connection with a promoter sequence that is capable of conferring expression of that fragment.

In an alternative embodiment, the present invention provides an expression library comprising nucleic acid fragments derived from one or two or more microorganisms or eukaryotes containing compact genomes, each of said microorganisms or eukaryotes having a substantially sequenced genome, wherein the nucleic acid fragments of the library have sufficiently different nucleotide sequences and comprise an open reading frame having an average length of at least about 36-45 nucleotide residues and/or encode a protein domain, and wherein the nucleic acid fragments are inserted into a suitable expression vector in an amount proportional to the size of the genome from, which the fragments were derived thereby producing recombinant constructs wherein each fragment is in operable connection with a promoter sequence that is capable of conferring expression of that fragment.

Preferably, if the library is to be expressed in either a cellular system or in an organism, the expression library is further comprise a host comprising the recombinant vectors of the expression library. In accordance with this embodiment, the expression library of the present invention further comprises a host cell comprising the nucleic acid fragments inserted into the expression vector.

In a particularly preferred embodiment the present invention provides an expression library produced in accordance with a method described herein (ie., it is a direct product of the method if the present invention).

A further aspect of the present invention provides a method of determining a peptide that binds to a target nucleic acid or target protein comprising:
(a) screening an expression library of the present invention to identify a peptide expressed by the library that binds to the target protein or target nucleic acid; and
(b) selecting a peptide from (a) that does not bind to said target protein or nucleic acid in its native environment.

In an alternative embodiment, the present invention provides a method of determining a peptide that binds to a target nucleic acid or target protein comprising:
(a) obtaining an expression library of the present invention;
(b) screening the expression library to identify a peptide that binds to the target protein or nucleic acid; and
(c) selecting a peptide that does not bind to said target protein or nucleic acid in its native environment.

In a further alternative embodiment, the present invention provides a method of determining a peptide that binds to a target nucleic acid or target protein comprising:
(a) producing an expression library of the present invention according to the process described herein;
(b) screening the expression library to identify a peptide that binds to the target protein or nucleic acid; and
(c) selecting a peptide that does not bind to said target protein or nucleic acid in its native environment.

The selection step of the screening process is to identify mimotopes or mimetic peptides, rather than merely selecting peptides that perform a known or expected function. Suitable processes for selecting a peptide that does not bind to the target protein or target nucleic acid in its native environment include, for example, determining the amino acid sequence of the peptide or determining the nucleotide sequence of the corresponding nucleic acid encoding said peptide and deriving the amino acid sequence from said nucleotide sequence, determining a known function of the amino acid sequence and excluding a peptide that binds to a target protein or target nucleic acid associated with the known function. Alternatively, or in addition, the selection involves using an expression library that comprises nucleic acid fragments from organisms that do not possess a particular biochemical pathway or signal transduction pathway relevant to the binding reaction being assayed. Alternatively, or in addition, the selection comprises using an expression library that comprises nucleic acid fragments from organisms that do not express one or more of the binding partners of the binding reaction being assayed. The present invention clearly contemplates the combined use of bioinformatic analysis and selection of library components from organisms that are not known to carry out the binding reaction being assayed, to exclude those peptides from the screening process that merely perform their known function. Accordingly, such selection ensures that the selected peptide or protein domain does not bind to the target protein or target nucleic acid in its native environment.

In one embodiment, the expression library of the present invention is screened using affinity purification. Affinity purification techniques are well known in the art and are described in, for example, Scopes (In: Protein purification: principles and practice, Third Edition, Springer Verlag, 1994). Methods of affinity purification typically involve contacting the peptides encoded by the nucleic acid fragment library of the present invention with a specific target protein or nucleic acid, and, following washing, eluting those peptides that remain bound to the target protein or nucleic acid. Said target protein or nucleic acid is bound to another molecule to allow for ease of purification, such as, for example, a molecule selected from the group consisting of protein A, protein G, agarose, biotin, glutathione S-transferase (GST), and FLAG epitope. Accordingly, the target protein or nucleic acid is isolated simply through centrifugation, or through binding to another molecule, eg. streptavidin, or binding of a specific antibody, eg. anti-FLAG anitbodies, or anti-GST antibodies. Methods using target proteins or nucleic acids covalently bound to affinity matrices are particularly preferred.

In another embodiment, the expression library of the present invention is expressed so as to allow identification of a bound peptide using FACS analysis. The screening of libraries using FACS analysis is described in U.S. Pat. No 6,455,63 (Rigel Pharmaceuticals Incorporated). In adapting the protocol to the present invention, it is particularly preferred that the expression libraries of the present invention are expressed in such that they are displayed, such as for example, using in vitro display, bacterial surface display, yeast display, or mammalian display.

Preferably, an in vitro display library is screened by FACS sorting. In vitro displayed proteins are covalently linked to a particle or bead suitable for FACS sorting, such as, for example, glass, polymers such as for example polystyrene, latex or cross-linked dextrans such as Sepharose, cellulose, nylon, teflon, amongst others.

The displayed library bound to particles or beads is added to a target protein or nucleic acid that has been labelled with a labelling moiety, such as for example a fluorescent molecule, or a molecule which is detected by a second fluorescent molecule. Methods of labelling a target protein or nucleic acid are well known in the art, and include methods using direct linkage or methods using a linker. The beads are then washed and subjected to sorting by FACS, which allows the beads with bound fluorescent target proteins or nucleic acids, to be separated from the beads that have not bound to a fluorescent target protein or nucleic acid.

Alternatively the library is screened using a biosensor-based assay, such as, for example, Biacore sensor chip technology (Biacore AB, UK). The Biacore sensor chip is a glass surface coated with a thin layer of gold modified with carboxymethylated dextran, to which the target protein or nucleic acid is covalently attached. The peptides encoded by the expression libraries of the present invention are then exposed to the Biacore sensor chip comprising the target protein or nucleic acid. Preferably, the nucleic acid fragment of the present invention and its encoded polypeptide are linked, such as for example using display technology.

The Biacore sensor chip is further used in the analysis of the kinetics of the interaction of the peptide encoded by the expression library of the present invention and the target protein or nucleic acid, such as for example through analyzing binding affinity using surface plasmon resonance. Essentially surface plasmon resonance detects changes in the mass of the aqueous layer close to the chip surface, through measuring changes in the refractive index. Accordingly, when a peptide encoded by the expression library of the present invention binds to the target protein or nucleic acid the refractive index increases.

The present invention is also be applied to identifying peptides that bind to any protein or nucleic acid, such as for example, a receptor protein, oncogenic protein, growth factor, cytokine, transcription factor, kinase, a promoter region of a gene, a suppressor region of a gene, a splice donor site, or a splice acceptor site. Alternatively, the libraries are screened to determine a peptide that modulates (inhibits, blocks, disrupts, down regulates, antagonizes, enhances, up regulates, agonizes, etc) a cellular process, biochemical reaction, protein: protein interaction, or a protein: nucleic acid interaction.

In one particularly preferred embodiment, the nucleic acid fragment expression libraries are screened for encoded peptides that bind to a target immunoglobulin, and preferably to the antigen binding site of a target immunoglobulin. Using standard affinity purification methods or any of the methods described herein, and appropriate antibodies as the target protein, it is possible to isolate peptide mimetics of both linear and discontinuous protein epitopes, in addition to other non-protein antigens, for example an antigen selected from the group consisting of: a carbohydrate, lipid, phospholipid, and protein (eg., Hi-PAL (P6) protein of *H. influenzae*, D15 protein from *H. influenzae*, the murM protein from *S. aureus*, the FemA protein from *S. aureus*, or the FemAB protein from *S. aureus*). Using subsequent rounds of screening performed at lower concentrations of the target antibody, those peptides that bind with high affinity are selected.

In another particularly preferred embodiment, the nucleic acid fragment expression libraries are screened for encoded peptides that inhibit or antagonize or block an interaction between two oncoproteins, such as, for example, SCL and E47. Such peptide antagonists ("peptide blockers") are particularly useful for validating a cellular target in the therapeutic treatment of cancer or for the therapeutic treatment of an individual suffering from a cancer, tumor or neoplastic illness, or alternatively in the prophylactic treatment of a subject having a predisposition or history of cancer, tumor or neoplastic illness. As exemplified herein, reverse two hybrid screens that assay the interaction between SCL and E47, have successfully been used to identify several specific peptide blockers of the SCL/E47 interaction in yeast cells, in addition to a small number of peptide blockers that are not specific for this interaction.

In a further embodiment, the nucleic acid fragments of the present invention are expressed as fusion proteins to form single-chain Fv (scFv) or Fab antibody fragments as described in McCafferty et al, *Nature* 348 552-534 (1990) and Hoogenboom et al, *Nucleic Acids Res* 19, 4133-4137 (1991). In a preferred embodiment the expression library of the present invention is used in the generation of a scFv library. The generation of a scFv library essentially involves generation of a gene construct comprising two or more nucleic acid fragments of the present invention separated by a nucleotide sequence encoding a scFv peptide linker, such as for example $(Gly_4Ser)_3$. The resulting gene construct is then expressed in an appropriate system to produce a single chain fragment of an antibody. It is particularly preferred that the expression library is displayed using a system described herein. Displayed library is screened for antibody fragments having a conformation sufficient for binding a specific antigen using techniques well known in the art, such as, for example, affinity purification.

Using techniques known in the art, scFv fragments are isolated that bind to specific antigens or molecules. Such techniques include, for example, affinity chromatography and 'n'-hybrid screening. Furthermore, through selection of increased nucleotide sequence diversity through, for example random mutagenesis, it is possible to select for antibodies with increased affinity for the specific antigen.

In a further embodiment, the present invention provides a method of identifying a peptide or protein domain that binds to a target protein or nucleic acid wherein said binding modulates a biological activity of the target protein or nucleic acid. As used herein, the term "biological activity" is to be taken in its broadest context and shall be taken to mean any activity of a substance that relates to a cellular process, or alternatively is required for a cellular event to occur. Examples of biological activity include, but are not limited to, an activity selected from the group comprising, protein binding to a target protein or nucleic acid, for example antibody and antigen binding, disruption of protein binding, modulation of cell signalling, modulation of gene expression, cell viability, cell proliferation, degradation of a protein or nucleotide, and/or preservation of a protein or nucleotide.

In another embodiment, the present invention provides a method of identifying a peptide or protein domain that binds to a target protein or nucleic acid wherein said binding inhibits the growth or viability of a microorganism. For example, comparative computer analysis of the genomes of microorganisms is used to identify those gene products that are specific to the microorganisms. Such information and comparative computer analysis software is available from, for example NCBI. The genome data of several microorganisms that are pathogens of the respiratory tract are compared to identify those sequences that are common to all of these species. These data are subtracted from genomic data of similar microorganisms that are not pathogens of the respiratory tract. Those sequences are specific to respiratory tract pathogens. This form of data analysis has been performed by, for example Read et al, *Drug Disc. Today* 6, 887-892 (2001). Any of these sequences that encode proteins is then be expressed and the encoded protein isolated, by methods that are well known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001). Such proteins are then used as a target for screening the nucleic acid fragment library of the present invention. Any peptides that are identified as having a conformation sufficient for binding to the target protein or nucleic acid, are tested for microbial toxicity, either through directly exposing the microbes to the peptide, or expressing the peptide in the target microorganisms by methods that are well known in the art and are described for example, in Ausubel et al (In: Current Protocols in Molecular Biology. Wiley Interscience, ISBN 047 150338, 1987), U.S. Pat. No. 5,763,239 (Diversa Corporation) and (Sambrook et al (In: Molecular Cloning: Molecular Cloning: A Laboratory Manual, Cold Spring Harbor Laboratories, New York, Third Edition 2001).

In a related embodiment, the present invention provides a method of identifying a peptide or protein domain that binds to a target protein or nucleic acid wherein said binding inhibits the growth or viability of an microorganism. In one form, the present embodiment relates to the insertion of the nucleic acid fragments that encode a polypeptide into a vector containing a conditional protein cleavage site, such as, for example, the temperature sensitive splicing element intein modified from the element found in the S. cerevesiae VMA1 gene. Such vectors include the IMPACT T7 system from New England Biolabs, for expression of peptides on the surface of T7 phage. Libraries generated using such vectors must be arrayed, such that each nucleic acid fragment is analyzed in isolation from other nucleic acid fragments, such methods are well known in the art, for example arraying individual phage or bacteria clones in a 96 well plate format. Accordingly, the vectors are transformed, transfected or transduced into an appropriate host, and the host cells placed under conditions for cleavage to occur, such as, for example, low temperatures in the case of the intein mutant cleavage. The cleaved peptides are then brought into physical contact with the microorganism. Those peptides that are capable of inhibiting the growth of the microorganism, or killing the microorganism is identified using standard techniques, and directly related to the arrayed nucleic acid fragment library.

The methods described herein above are readily modified to suit other gene expression systems, such as for example those systems that secrete the peptide encoded by the expression library of the present invention, and those systems that lyse the host cell that express the peptide encoded by the expression library of the present invention, such as for example, the expression of the peptides from different open reading frames of the same nucleic acid fragment in the T7 lytic phage.

In a related embodiment, libraries that encode peptides in a secretable form, or libraries wherein a host cell is lyzed in preparation for screening, are screened using an assay employing a filter diffusion assay. Such an assay utilises a double faced Petri dish, with the two faces of the dish are separated by a supported semi-permeable membrane which will allow the diffusion of the peptides encoded by the expression library of the present invention, such as for example a membrane selected from the group comprising, nitrocellulose and nylon. A lawn of the microorganism is grown on one side of said double-faced Petri dish. Host cells expressing the expression library are grown on the opposite side of a double-faced Petri dish. The presence of plaques in the lawn of the microorganism is suggestive of the expression and diffusion of a peptide that can inhibit the growth of or kill said microorganism. The nucleic acid is then be isolated from the equivalent region of the phage overlay, using techniques well known in the art.

In a related embodiment, a library of T7 phage expressing free peptides is transferred to a nylon membrane before being placed on a newly seeded lawn of pathogenic bacteria. Plaques appearing in this lawn are correlated by orientating the filter to plaques on the E. coli/T7 lawn expressing bacteriostatic or antibacterial peptides.

In another embodiment, the expression library of the present invention is introduced into a plurality of suitable host cells using the methods of introducing recombinant expression vectors described herein. Cells are then monitored for a change in the phenotype such as for example, as described in Xu et al, (In: Nature Genetics 27, 23-29, 2001). Examples of phenotypic changes include, but a not limited to a phenotypic change selected from the group comprising, modulation of cellular proliferation, morphological changes, resistance to toxins, susceptibility to toxins, and gene expression changes. In adapting the described technique to the present invention, appropriate host cells are transformed or transfected with the expression libraries of the present invention, using methods well known in the art, and described above. Alternatively recombinant peptides isolated from the expression libraries of the present invention is incubated with the host cells, in the presence of a polypeptide that facilitates the uptake of peptides into host cells. Said host cells are then monitored for specific phenotype changes, such as for example gene expression changes monitored using DNA microarrays. The nucleic acid encoding the peptide that induces the phenotypic change is then isolated. Further testing of the peptide that induces the desired change in phenotype is clearly envisaged, such as, for example, two-hybrid analysis to determine which proteins the peptides interacts with, and which cellular pathways it is affect.

Preferably, those peptides that are identified in any of the above-mentioned screens to bind to a target protein or nucleic acid are recovered and analyzed.

In one embodiment, the nucleotide sequence of the nucleic acid encoding the identified peptide or protein domain is determined. Preferably, the sequences of several distinct peptides identified in a specific screen of a library are aligned and compared, and highly conserved primary and/or secondary structures within the peptides or protein domains are determined. Alternatively, or in addition, less conserved structures are also determined. More preferably, the highly conserved structural features are used to design and/or to produce additional peptides having the same or enhanced binding properties as the peptides identified in the initial screening.

In an alternative embodiment, the recovered peptide or protein domain and/or nucleic acid encoding same is recovered and used to validate a therapeutic target (ie. it is used as a target validation reagent). By virtue of its ability to bind to a specific target protein or target nucleic acid, it is well within the ken of a skill artisan to determine the in vivo effect of modulating the activity of the target protein or target nucleic acid by expressing the identified peptide or protein domain in an organism (eg., a bacterium, plant or animal such as, for example, an experimental animal or a human). In accordance with this aspect of the present invention, a phenotype of an organism that expresses the identified peptide or protein domain is compared to a phenotype of an otherwise isogenic organism (ie. an organism of the same species or strain and comprising a substantially identical genotype however does not express the peptide or protein domain). This is performed under conditions sufficient to induce the phenotype that involves the target protein or target nucleic acid. The ability of the peptide or protein domain to specifically prevent expression of the phenotype, preferably without undesirable or pleiotropic side-effects indicates that the target protein or target nucleic acid is a suitable target for development of therapeutic/prophylactic reagents.

Accordingly, a further aspect of the present invention provides a method for determining a therapeutic or prophylactic target comprising
(a) screening an expression library of the present invention to identify a peptide expressed by the library that binds to a target protein or target nucleic acid;
(b) selecting a peptide from (a) that does not bind to said target protein or nucleic acid in its native environment; and
(c) expressing the selected peptide in an organism and determining a phenotype of the organism that is modulated by the target protein or target nucleic acid.

Preferably, determining a phenotype of the organism that is modulated by the target protein or target nucleic acid comprises comparing the organism to an otherwise isogenic organism that does not express the selected peptide. For example, the phenotype of an organism that expresses a tumor is assayed in the presence and absence of a peptide or protein domain that blocks an interaction between SCL and E47 in a screen of the expression library of the invention. Amelioration of the oncogenic phenotype by the expressed peptide indicates that the SCL/E47 is a suitable target for intervention, wherein the peptide is then suitably formulated for therapeutic intervention directly, or alternatively, small molecules are identified that are mimetics of the identified peptide or protein domain.

It is to be understood that any use of an expression library of the present invention extends to the obtaining of said expression library, or the production of the expression library.

It will also be apparent from the preceding description that the library can be screened using an selected from the group consisting of yeast-2-hybrid, n-hybrid, reverse-2-hybrid, reverse n-hybrid, split two hybrid, bacterial display, phage display, retroviral display, covalent display and in vitro display, or using an affinity purification, such as, for example, an immunoassay that measures the formation of an antigen-antibody complex.

It will also be apparent from the description herein that the peptide selection may comprise (i) determining the amino acid sequence of the peptide or determining the nucleotide sequence of the corresponding nucleic acid encoding said peptide and deriving the amino acid sequence from said nucleotide sequence or determining a known function of the amino acid sequence; and (ii) excluding a peptide that binds to a target protein or target nucleic acid associated with the known sequence or known function.

In accordance with this embodiment, a selection is applied (eg., using flow cytometry to sort cells with particular surface expression characteristics) to isolate library transformants which have acquired a desired phenotype. The amino acid sequence of the peptide expressed from such positively selected clones is then be determined by PCR cloning and sequencing. Two hybrid screening, as described herein, using the isolated peptide as a bait protein is used to identify the target proteins which the peptide bound to exert its phenotypic effect.

By way of an example, the expression library of the present invention is introduced into a cell line and expression induced. After a time sufficient for expression of the peptides encoded by the expression library to occur, the cells are exposed to a toxin to which the wild type cells are susceptible, such as, for example staurosporine. Following such exposure, those cells that are not resistant to the toxin die by apoptosis. Those cells that survive the selection pressure are analyzed further to determine if their survival is a consequence of their expressing a peptide that enables them to survive exposure to the toxin. Preferably, the nucleic acid encoding this peptide is isolated and sub-cloned for further analysis.

In another embodiment, the expression library of the present invention is arrayed and individual nucleic acid fragments or pools of nucleic acid fragments are introduced into a whole organism, using methods well known in the art, and described herein.

Particular model organisms include, but are not limited to, *Arabidopsis thaliana, Anopheles gambiae, Caenorhabditis elegans, Danio rerio, Drosophila melanogaster, Mus* sp., *Takifugu rubripes, Rattus* sp., *Saccharomyces cerevesiae,* and *Schizosaccharomyces pombe*. Array methods described in Hogan et al (In: Manipulating the Mouse Embryo. A Laboratory Manual, $2^{nd}$ Edition. Cold Spring Harbour Laboratory. ISBN: 0879693843, 1994) are preferred. After a time sufficient for the organisms to develop to a suitable stage in the life cycle for a target phenotype to be expressed, transformed organisms are monitored for a change in the phenotype, using methods well known in the art, such as for example the SHIRPA protocol described in Rogers et al, *Mamm. Genome* 8 (10), 711-713, 1997. Organisms expressing a desired change in phenotype are retained for further analysis. Further testing of the peptide that induces the desired change is clearly encompassed by the present invention.

A similar method is applied to the identification of those nucleic acids that encode a polypeptide that confers resistance to, for example, toxins, pathogens, or specific forms of cancer. By way of example, fertilized mouse ova are microinjected with individual, or pools of gene constructs comprising nucleic acid fragments of the present invention. After implanting the microinjected ova and allowing transgenic mice to be born and to develop beyond weaning (ie. approximately 21 days), mice are exposed to a challenge by a microorganism, such as for example *P. falciparum*. Following an exposure to *P. falcipartim* at high dose, mice that are susceptible to *P. falciparum* die. Mice that do not die are retained and nucleic acid used to produce those mice are recovered (eg., by PCR) and the sequences determined.

It will also be appreciated by those skilled in the art that the above described method is adapted to monitor any phenotypic changes, for example through methods selected from the group comprising $^3$H incorporation, measures of apoptosis (eg TUNEL staining), secretion of particular hormones/proteins, and morphological changes, amongst others In a related embodiment those peptides that are able to modulate the phenotype are further analyzed to determine those cellular components with which the peptide interacts. Methods used in the analysis of protein interactions are well known in the art and are described in Weber (In: Protein interactions. Chapman and Hall, New York, 1992). Through determining the proteins with which the peptides interact, the gene expression libraries of the present invention is used for the validation of potential drug targets or in determining the proteins involved in specific cellular pathways and processes.

A particularly preferred embodiment of the present invention relates to the identification of a peptide or protein domain that is able to modulate the biological activity of a target protein or nucleic acid, wherein the modulated biological activity is the ability of the target protein or nucleic acid to bind to another protein or nucleic acid and wherein the modulated binding is determined using a reporter molecule. As used herein, the term "reporter molecule" shall be taken to mean a molecule that displays a physically measurable property that alters in a way that can be measured and correlated with changes in the biological activity or a target protein or nucleic acid. Reporter molecules are well known in the art, and include, but are not limited to, proteins that fluoresce, for example green fluorescence protein, proteins that induce a colour change in the presence of a substrate, for example E coli β-galactosidase, molecules that confer growth characteristics on the host cells, such as for example HIS1, and molecules that induce the death or reduced growth ability of the host cells, such as for example URA3 and CYH1.

One embodiment of the present invention relates to the identification of nucleic acids that encode peptides having a conformation capable of binding to a DNA sequence. The one-hybrid assay, as described in Chong and Mandel (In: Bartel and Fields, The Yeast Two-Hybrid System, New York, N.Y. pp 289-297, 1997) is used to determine those peptides able to bind to a target DNA sequence. In adapting the standard one-hybrid technique to the present purpose, the target nucleotide sequence is incorporated into the promoter region of a reporter gene(s), the expression of which can be determined as described above. The peptide encoded by the expression library of the present invention is expressed in such a manner that it forms a fusion protein with a transcriptional activation domain (for example from the GAL4 protein, the LexA protein, or the mouse NF κB protein). The transcriptional activation domain is recruited to the promoter through a functional interaction between the expressed peptide and the target nucleotide sequence. The transcriptional activation domain subsequently interacts with the basal transcriptional machinery of the cell, activating expression of the reporter genes.

In another embodiment a polypeptide is identified that is able to bind a target protein or peptide using the two-hybrid assay described in U.S. Pat. No. 6,316,223 to Payan et al and Bartel and Fields, The Yeast Two-Hybrid System, New York, N.Y., 1997. The basic mechanism described requires that the binding partners are expressed as two distinct fusion proteins in an appropriate host cell, such as for example bacterial cells, yeast cells, and mammalian cells. In adapting the standard two-hybrid screen to the present purpose, a first fusion protein consists of a DNA binding domain fused to the target protein, and a second fusion protein consists of a transcriptional activation domain fused to the peptide encoded by the expression library of the present invention. The DNA binding domain binds to an operator sequence which controls expression of one or more reporter genes. The transcriptional activation domain is recruited to the promoter through the functional interaction between the peptide expressed by the expression library of the present invention and the target protein. Subsequently, the transcriptional activation domain interacts with the basal transcription machinery of the cell, thereby activating expression of the reporter gene(s), the expression of which can be determined.

The three hybrid assay as described in Zhang et al (In: Bartel and Fields, The Yeast Two-Hybrid System, New York, N.Y. pp 289-297, 1997) is used to determine those peptides that bind target RNA sequences. In adapting the described 3-hybrid technique to the present invention, a first fusion protein consists of a DNA binding domain which is fused to a known RNA binding protein, eg. the coat protein of bacteriophage MS2. An RNA hybrid molecule is also formed, consisting of a fusion between a RNA molecule known to bind the RNA binding protein, eg. MS2 binding sequences, and a target RNA binding sequence. A second fusion protein consists of a transcriptional activation domain fused to the peptide encoded by the expression library of the present invention. The DNA binding domain of the first fusion protein binds to an operator sequence that controls expression of one or more reporter genes. The RNA fusion molecule is recruited to the first fusion protein through the functional interaction between the RNA binding protein and the RNA molecule known to interact with said RNA binding protein. The transcriptional activation domain is recruited to the promoter of one or more reporter molecules through functional interaction between the target RNA sequence of the peptide encoded by the nucleic acid of the present invention.

Other modifications of the two-hybrid screens are well known in the art, such as for example the PolIII two hybrid system, the Tribrid system, the ubiquitin based split protein sensor system and the Sos recruitment system as described in Vidal and Legrain *Nucl. Acid Res.* 27 (4), 919-929 (1999). All of these systems are particularly contemplated.

A particularly preferred embodiment of the present invention relates to the identification of peptides that antagonize or inhibit the interaction between the target protein or nucleic acid and another protein or nucleic acid. Accordingly, reverse 'n'-hybrid screens are employed to identify agonist molecules. Reverse hybrid screens differ from the forward hybrid screens supra in that they use a counter selectable reporter marker(s), such as for example the URA3 gene, the CYH2 gene or the LYS2 gene, to select against interactions between the target protein or nucleic acid and another protein or nucleic acid. Cell survival or cell growth is reduced or prevented in the presence of a non-toxic substrate of the counter selectable reporter gene product, which is converted by the counter selectable marker to a toxic compound, such as for example the CYH1 gene product which confers lethality in the presence of cycloheximide. Accordingly, cells in which the interaction between the target protein and another protein or nucleic acid is blocked or inhibited survive in the presence of the substrate. This is because the counter selectable reporter molecule will not be expressed, and accordingly, the substrate will not be converted to a toxic product. Such a result suggests that the peptide encoded by the expression library of the present invention is an inhibitor of the interaction between the target protein or nucleic acid and another protein or nucleic acid.

In a particularly preferred embodiment, the screening method of the present invention identifies an antagonist of a protein: protein interaction or protein: nucleic acid interaction. In accordance with this embodiment, the present invention provides a reverse two hybrid screening process, such as, for example, essentially as described by Watt et at. (U.S. Ser. No. 09/227,652), for identifying an inhibitory amino acid sequence that partially or completely inhibits a target protein-protein interaction or DNA-protein interaction involving one or more protein binding partners said method comprising:

(i) providing cells that each comprise: (a) a nucleic acid comprising a counter-selectable reporter gene encoding a polypeptide that is capable of reducing cell growth or viability by providing a target for a cytotoxic or cytostatic compound (eg., CYH2 gene that confers susceptibility to cycloheximide) or by converting a substrate to a cytotoxic or cytostatic product (eg., URA3 gene that converts 5-FOA to a toxic product), said gene being positioned downstream of a promoter comprising a cis-acting element such that expression of said gene is operably under the control of said promoter and wherein a protein binding partner of the protein-protein interaction or the DNA-protein interaction being assayed binds to said cis-acting element; and (b) nucleic acid selected from the group consisting of: (i) nucleic acid encoding a protein of the DNA-protein interaction that binds to said cis-acting element to activate expression of the counter-selectable reporter gene; and (ii) nucleic acids encoding two protein binding partners of the protein-protein interaction wherein a protein binding partner binds to the cis-acting element and the protein binding partners interact, said binding to the cis-acting element and said interaction being required to activate expression of the counter-selectable reporter gene;

(ii) transforming or transfecting the cells or a portion of the cells with an expression library of the invention such that a single gene construct of the expression library is present in each transformed or transfected cell;

(iii) culturing the transformed or transfected cells for a time and under conditions sufficient for the protein binding partner(s) to activate expression of the counter-selectable reporter gene in the absence of inhibition of the protein-protein interaction or the DNA-protein interaction by an amino acid sequence encoded by the expression library;

(iv) culturing the transformed or transfected cells under conditions sufficient for an amino acid sequence of the expression library to be expressed in each of said transformed or transfected cells or a proportion of said transformed or transfected cells;

(v) culturing the transformed or transfected cells in the presence of the substrate or the cytotoxic or cytostatic compound such that the expressed counter-selectable reporter gene reduces the growth or viability of the cells unless said expression is reduced by virtue of an amino acid sequence of the expression library inhibiting the target protein-protein interaction or DNA-protein interaction;

(vi) selecting a cell having enhanced growth or viability compared to a cell that does not express the amino acid sequence of the expression library wherein the enhanced growth or viability is indicative of a partial or complete inhibition of the protein-protein interaction or a DNA-protein interaction by the amino acid sequence and (vii) selecting a peptide expressed by the cell at (vi) that does not bind to a protein or nucleic acid of the protein-protein interaction or a DNA-protein interaction in its native environment.

Preferably, wherein a protein-protein interaction is being assayed, the binding of the two protein binding partners reconstitutes a functional transcriptional regulatory protein, such as, for example, by virtue of the binding partners being expressed as fusion proteins wherein each fusion protein comprises a portion of a transcriptional regulatory protein that does not modulate transcription without the other portion (eg., a fusion protein comprising a transcriptional activator domain and a fusion protein comprising a DNA-binding domain). In a particularly preferred embodiment, one fusion protein comprises a Gal4 DNA-binding domain fused to SCL, and another fusion protein comprises the transcriptional activation domain of the LMO2 protein and a domain that interacts with SCL and the URA3 counter selectable reporter gene is operably under the control of a promoter comprising a Gal4 upstream activator sequence (Gal4 UAS), such that docking of the Gal4/SCL fusion to the Gal4 UAS and binding between SCL and LMO2 is required to activate transcription of the URA3 gene, thereby conferring lethality on cells grown in the presence of 5-fluoro orotic acid (5-FOA). In screening the expression library, only those cells that survive in the presence of 5-FOA are selected.

For example, a specific receptor is expressed as a DNA binding domain fusion protein, such as with the DNA binding domain of GAL4, and the ligand of said receptor is expressed as an activation domain fusion protein, such as with the GAL4 activation domain. These fusion proteins are expressed in yeast cells in operable connection with the CYH1 counter selectable marker, wherein expression of the CYH1 gene requires a physical interaction between the GAL4 DNA binding domain and the GAL4 activation domain. This physical relation is achieved is achieved, for example, by placing the expression of the marker gene under the control of a promoter comprising nucleotide sequences to which the GAL4 DNA binding domain binds. Cells in which the reporter gene is expressed do not grow in the presence of cycloheximide, because the 5-FOA is converted to a toxic compound. The expression libraries of the present invention are expressed in these yeast cells and those cells that then grow in the presence of cycloheximide are further analyzed, such as, for example, analysis of the nucleic acid encoding the candidate peptide inhibitor(s).

As will be known to the skilled artisan, the reverse 'n'-hybrid technique briefly described above is readily modified for use in 1-hybrid, 2-hybrid or 3-hybrid assays.

In an alternative embodiment, the antagonist is identified using a reverse split two hybrid screening process, such as, for example, essentially as described by Erickson et al. (WO95/26400), wherein a relay gene that is a negative regulator of transcription is employed to repress transcription of a positive readout reporter gene when the interacting proteins (ie., bait and prey) interact, such that reporter gene expression is only induced in the absence of the protein encoded by the relay gene product. In accordance with this embodiment, there is provided a method for identifying an inhibitory amino acid sequence that partially or completely inhibits a target protein-protein interaction or DNA-protein interaction involving one or more protein binding partners said method comprising:

(i) providing cells that each comprise: (a) a nucleic acid encoding a negative regulator of transcription (eg., Gal80 or mdm2 oncoprotein-encoding gene), said nucleic acid being positioned downstream of a promoter comprising a cis-acting element and wherein a protein binding partner of the protein-protein interaction or the DNA-protein interaction being assayed binds to said cis-acting element; (b) nucleic acid selected from the group consisting of: (i) nucleic acid encoding a protein of the DNA-protein interaction that binds to said cis-acting element to activate expression of the negative regulator of transcription; and (ii) nucleic acids encoding two protein binding partners of the protein-protein interaction wherein a protein binding partner binds to the cis-acting element and the protein binding partners interact, said binding to the cis-acting element and said interaction being required to activate expression of the negative regulator of transcription; and (c) nucleic acid comprising a positive reporter gene (eg., an antibiotic resistance gene, herbicide resistance gene, or other resistance gene) operably connected to a cis-acting element (eg., a GAL4 binding site capable of binding to Gal80, or Gal80, or the transactivation domain of p53 that binds to mdm2 oncoprotein) to which the negative regulator of transcription binds to thereby inhibit or repress expression of the positive reporter gene;

(ii) transforming or transfecting the cells or a portion of the cells with an expression library of the invention such that a single gene construct of the expression library is present in each transformed or transfected cell;

(iii) culturing the transformed or transfected cells for a time and under conditions sufficient for the protein binding partner(s) to activate expression of negative regulator of transcription in the absence of inhibition of the protein-protein interaction or the DNA-protein interaction by an amino acid sequence encoded by the expression library;

(iv) culturing the transformed or transfected cells under conditions sufficient for an amino acid sequence of the expression library to be expressed in each of said transformed or transfected cells or a proportion of said transformed or transfected cells;

(v) culturing the transformed or transfected cells in the presence of a compound to which the positive reporter gene confers resistance on the cells such that the expressed negative regulator of transcription represses expression of the positive reporter gene thereby reducing the growth or viability of the cells unless said expression is reduced by virtue of an amino acid sequence of the expression library inhibiting the target protein-protein interaction or DNA-protein interaction;

(vi) selecting a cell having enhanced growth or viability compared to a cell that does not express the amino acid sequence of the expression library wherein the enhanced growth or viability is indicative of a partial or complete inhibition of the protein-protein interaction or a DNA-protein interaction by the amino acid sequence and (vii) selecting a peptide expressed by the cell at (vi) that does not bind to a protein or nucleic acid of the protein-protein interaction or a DNA-protein interaction in its native environment.

Preferably, wherein a protein-protein interaction is being assayed, the binding of the two protein binding partners reconstitutes a functional transcriptional regulatory protein. In a particularly preferred embodiment, one protein comprises a LexA fusion protein, and another protein comprises a VP16 fusion protein, and the positive reporter gene confers resistance against cycloheximide and is placed operably under the control of a promoter comprising a Gal4 upstream activator sequence (Gal4 UAS), such that docking of a Gal80 negative regulator of transcription to the Gal4 UAS and binding between SCL and LMO2 is required to repress transcription of the positive reporter gene, thereby preventing cells from proliferating. Conversely, repression of the interaction between the LexA-fusion and VP16 fusion prevents Gal80 expression allowing expression of the positive reporter gene to confer resistance on cells in the presence of cycloheximide, particularly in cells that express endogenous Gal4 protein.

In a preferred embodiment of the present invention, those nucleic acid fragments that encode a polypeptide that binds to a target protein or nucleic acid are exposed to further rounds of selection using, for example, mutagenic PCR or expression of said fragments in "mutator" strains of bacteria. This increases the diversity of the selected nucleic acid. Said selected nucleic acid is again screened for those that encode a peptide having a conformation sufficient for binding a target protein or nucleic acid. Through multiple rounds of screening and selection with lower concentrations of the target protein or nucleic acid, those peptides with the highest affinity for the target protein or nucleic acid are selected.

In a related embodiment, the sequences of those nucleic acid fragments encoding peptides that bind to the target protein or nucleic acid are optimally aligned and the sequences compared to identify those nucleic acids that encode amino acids that are particularly desired for binding the target protein or nucleic acid. Furthermore, this information is used to generate synthetic nucleotide sequences encoding peptides, or synthetic peptides, containing those amino acids that are particularly desirable for binding to a target protein or nucleic acid.

Preferably, those peptides that bind to the target protein or nucleic acid, are recovered and used in further analysis, such as for example, determining the nucleotide sequence of the nucleic acid encoding the identified peptide or protein domain. Initially, the nucleic acid fragment encoding the peptide is isolated using methods well known in the art, such as for example, PCR, RT-PCR, and nucleic acid isolation, amongst others. An isolated nucleic acid fragment is then characterized by methods such as nucleic acid sequencing. Such methods are well known in the art.

In one embodiment, an insolated nucleic acid fragment is placed into an expression vector using methods well known in the art, and described herein. Such a nucleic acid fragment is only expressed in a single reading frame and only in one direction. This method is repeated until all possible open reading frames of the nucleic acid fragment are tested, and that/those that encode a polypeptide having a conformation sufficient for binding a target protein or nucleic acid are identified. As used herein the term "all possible open reading frames" shall include those open reading frames that include the entire nucleic acid fragment, in addition to those open reading frames that is formed within a nucleic acid fragment, such as for example by the inclusion of a second ATG start codon, a Kozak sequence, a Shine-Dalgarno sequence, or an internal ribosome entry sequence, amongst others. All of the expressed peptides are then screened in an appropriate screening system to determine those that have a conformation sufficient for binding to a target protein or nucleic acid. Accordingly, analysis of the nucleic acid encoding such a peptide is used to determine the amino acid sequence of the peptide. Using such software as the Translate tool available at ExPasy. As used herein, the term "ExPasy" shall be understood to mean, the ExPasy proteomics server provided by the Swiss Institute of Bioinformatics at CMU-Rue Michel—Servet 1 1211 Genève 4 Switzerland.

Following isolation of the nucleic acid that encodes a peptide with a conformation sufficient for binding to a target protein or nucleic acid, it is preferred that all homologues of this sequence are isolated from the genomes of the organisms used to generate the expression library of the present invention. Methods of isolating homologous nucleic acid regions are well known in the art and are described, for example, in Dieffenbach (ed) and Dveksler (ed) (In: PCR Primer: A Laboratory Manual, Cold Spring Harbour Laboratories, NY, 1995). Such methods include PCR and degenerate PCR. Such homologues are then screened in all possible reading frames using a suitable screening system, as are known in the art and described herein.

It is a further preferred embodiment that an identified nucleotide sequence or amino acid sequence shall be used as a "reference sequence" for a homology search using a database of all known sequences. Such a reference sequence is a nucleotide or amino acid sequence to which all nucleotides or amino acid sequences in a database are compared. A number of source databases are available that contain either a nucleotide sequence and/or a deduced amino acid sequence that are particularly useful to identify all known sequences that are substantially homologous the sequence of nucleic acid or peptide, polypeptide or protein domain identified as positive in the present invention. Such databases are well known in the art and include, for example, Genbank (at NCBI) and SWISS-PROT and TrEMBL (available at ExPasy). A number of different methods of performing such sequence searches are known in the art. The sequence data of the clone is then aligned to the sequences in the database or databases using algorithms designed to measure homology between two or more sequences.

In one embodiment, a nucleic acid identified in a homology search of the known nucleic acids is isolated using one of a variety of methods well known in the art, such as for example PCR amplification of the specific region of genomic DNA or cDNA of the organism in which the nucleic acid is naturally found. The sequence of the isolated nucleic acid is determined, used to generate a gene construct as described herein, and screened to determine if it encodes a peptide that has a conformation sufficient for binding the target protein or nucleic acid.

In another embodiment a nucleic acid encoding an amino acid sequence identified in a homology search of known amino acid sequences using techniques well known in the art, such as for example degenerate PCR. An isolated nucleic acid is then used to generate a gene construct as described herein, and screened to determine if it encodes a peptide that has a conformation sufficient for binding the target protein or nucleic acid.

It is a particularly preferred embodiment of the present invention that those nucleic acids that encode a polypeptide having a conformation that binds to a target protein or nucleic acid are analyzed to select those nucleic acid fragments that encode polypeptides that do not bind to said target protein or nucleic acid in its native environment. As used herein, the term "native environment" of a polypeptide shall be understood to mean the protein encoded by the gene from which the nucleic acid fragment was isolated. Accordingly, it is the aim of the present invention to identify those polypeptides that display a novel function, for example by binding to a target protein or nucleic acid to which it cannot bind in the context of the protein in which it naturally occurs.

The known function/s of the polypeptides isolated in the screening of the libraries of the present invention are determined using sequence analysis software as is available from, for example NCBI, or Prosite. As used herein the term "Prosite" shall be understood to mean the Prosite protein database which is a part of the ExPasy proteomics server provided by the Swiss Institute of Bioinformatics at CMU-Rue Michel—Servet 1 1211 Genève 4 Switzerland. Accordingly, those polypeptides that are known to bind to the target protein or nucleic acid in their native environment are excluded from any further analysis. Furthermore, analysis of the bioinformatic information available, for example, at NCBI aids in determining the native function of a protein. Such analysis will determine if, for example, the pathway being modified exists in an organism from which a peptide is identified or if a target protein or nucleic acid is found in any of the organisms used to generate an expression library.

It is particularly preferred that an expression library of the present invention is generated using nucleic acid fragments isolated from organisms that are distinct from the organism in which the target protein or nucleic acid naturally occurs. For example, to identify a nucleic acid that encodes a peptide that has a conformation sufficient for binding the Hi-PAL (P6) outer membrane protein of *Haemophilus influenzae* an expression library is generated from the organisms *Aeropyrum pernix, Aquifex aeolicus, Archaeoglobus fulgidis, Bacillus subtilis, Bordetella pertussis, Borrelia burgdoiferi, Chlamydia trachomatis, Escherichia coli, Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Thermoplasma volcanium* and *Thermotoga maritima*. This will reduce the likelihood of identifying a peptide that interacts with the Hi-PAL (P6) protein in its native environment. Even more preferably, an expression library is generated using the organisms *Aeropyrum pernix, Aquifex aeolicus, Arabidopsis thaliana, Archaeoglobus fulgidis, Caenorhabditis elegans, Danio rerio, Drosophila melanogaster, Methanobacterium thermoautotrophicum, Methanococcus jannaschii, Pyrococcus horikoshii, Saccharomyces cerevesiae, Takifugu rubripes, Thermoplasma volcanium*, and *Thermotoga maritima* as these organisms are unlikely to occur in the same environment as *Haemophilus influenzae*, and as such, any peptide isolated from such an expression library would be especially unlikely to interact with Hi-PAL (P6) in its native environment.

Another aspect of the present invention is a database of nucleic acids that are found in an expression library of the present invention. As the nucleic acid fragments are derived from organisms with substantially sequenced genomes, it is possible to use this information to generate a database of the nucleotide sequences of nucleic acid fragments that is generated in the construction of an expression library of the present invention.

The utility of the database lies in the ability for a skilled person to search the database for a nucleotide sequence or amino acid sequence determined by screening an expression library of the present invention. In this way, it is possible to identify nucleic acid fragments that encode a peptide that is adopt a conformation sufficient for binding to a specific target protein or nucleic acid. Furthermore, the database allows the user to identify a sequence that is homologous to a nucleic acid, in addition to determining from which species it is derived. Once a sequence is identified, the specific nucleic acid is isolated from the expression library using techniques well known in the art, eg. PCR and the expressed peptide analyzed.

Nucleotide sequences of the nucleic acid fragments of the expression library are derived from any one of many publicly known databases, such as for example NCBI or TIGR, as the organisms used in the generation of an expression library of the present invention has a substantially sequenced genome.

Amino acid sequences that are found in the database are derived by conceptual translation of nucleotide sequences that are found in an expression library of the present invention. The conceptual translation of a nucleotide sequence comprises applying the known codon usage rules to obtain hypothetical peptide sequences by translating a nucleotide sequence in both orientations and in all three reading frames for each possible orientation. Software for translation of nucleotide sequence to amino acid sequence is well known in the art, and includes, for example, the Translate tool at ExPasy. Care is taken to translate a nucleotide sequence using the known codon usage of the organism in which a nucleic acid fragment is to be expressed. Such codon usage information is well known in the art. Amino acid sequences are also derived by sequencing the expressed peptides. Methods of sequencing peptides and proteins are well known in the art.

Alternatively or in addition, various comparisons can be made between the Library database sequences and any other sequence database as would be familiar to those practiced in the art.

Additionally, the sequence information is used to generate a highly specific probe for isolating both genomic clones from existing databases, as well as cDNA. Additionally, the probe is used to isolate the homologous nucleic acid fragment from sufficiently related species, including humans. Once isolated, the nucleic acid fragment is inserted into a gene construct and screened as herein described.

In a related embodiment, a database of amino acid sequences of peptides is analyzed to generate a database of potential domain structures, or three-dimensional structures that is formed by a peptide expressed by the expression library of the present invention. Methods for predicting the 3 dimensional structure of a peptide are well known in the art, and are described, for example, in US Patent Application No. 20020150906 (California Institute of Technology), or using a computer program or algorithm, such as, for example, MODELLER, (Sali and Blundell, *J. Mol. Biol.* 234, 779-815, 1993). These techniques rely upon aligning the sequence of a peptide with the sequences of peptides or proteins that have a characterized structure. Such alignment algorithms are well known in the art and are accessed through software packages such as, for example BLAST at NCBI. Structural information, ie. three-dimensional structure, of a query peptide is then be predicted based upon structural information corresponding to the sequence or subsequences aligned in the proteins or peptides that have previously been characterized. In this way it is possible to generate a library of three-dimensional structures of peptides expressed from the expression library of the present invention. This information is used to determine those sequences that is adopt a conformation sufficient for binding to a target protein or nucleic acid. Accordingly, the nucleic acid fragment encoding such a peptide is isolated using methods well known in the art, and inserted into a gene construct. The encoded peptide is then screened using the methods described herein.

The present invention is further described with reference to the following non-limiting examples.

EXAMPLE 1

The Construction of a Biodiverse Nucleic Acid Fragment Expression Library in the Bector pDEATH-Trp Nucleic acid was isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *S nechosistis* PCC 6803 |
| 18 | *Thermoplasma volcanium* |
| 19 | *Thermotoga maritima* |

Nucleic acid fragments were generated from the genomic DNA of each genome using 2 consecutive rounds of PCR using tagged random oligonucleotides with the sequence:
5'-GACTACAAGGACGACGACGACAAGGCT-TATCAATCAATCAN$_6$-3' (SEQ ID NO: 33). The PCR amplification was completed using the Klenow fragment of *E. coli* DNA polymerase I in the following PCR reaction:

| Reagent | Volume |
|---|---|
| DNA (100–200 ng) | |
| Oligonucleotide comprising SEQ ID NO: 33 (25 µM) | 4 µl |
| H$_2$O | to 17.4 µl. |

Samples were then boiled for 3-5 minutes to denature the nucleic acid isolated from the bacteria, before being snap cooled, to allow the tagged random oligonucleotides to anneal to said nucleic acid. These samples were then added to the following reagents:

| | |
|---|---|
| Klenow buffer | 3 µl |
| dNTP (2 mM) | 3 µl |
| Klenow | 0.6 µl |
| Polyethylene Glycol (8,500) | 6 µl |

PCR reactions were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 µl of the Klenow fragment of *E. coli* DNA polymerase I was added to each reaction and the samples incubated at 15° C. for 30 minutes, then at room temperature for 2 hours, before being heated to 37° C. for 15 minutes.

Following boiling the samples, following snap cooling another 2 rounds of PCR were completed using the tagged random oligonucleotide:
5'-GACTACAAGGACGACGACGACAAGGCT-TATCAATCAATCAN$_9$-3' (SEQ ID NO: 34)

To complete this the following reagents were added to the samples of the previous step:

| | |
|---|---|
| Oligonucleotide comprising SEQ ID NO 34 (25 µM) | 4 µl |
| Klenow Buffer | 1 µl |
| dNTP (2 mM) | 3 µl |
| Klenow | 0.5 µl |
| H$_2$O | to 40 µl |

Samples were then incubated at 15° C. for 30 minutes, then at room temperature for 2 hours, before being heated to 37° C. for 15 minutes.

Samples were boiled for 5 minutes to again denature the nucleic acid, before being snap cooled to allow renaturation of said nucleic acid. Another 0.5 µl of the Klenow fragment of *E. coli* DNA polymerase I was added to each reaction and the samples incubated at 15° C. for 30 minutes, then at room temperature for 2 hours, before being heated to 37° C. for 15 minutes.

Following completion of the PCR amplification all sample volumes were increased to 500 µl with TE buffer and added to an Amicon spin column. These columns were then centrifuged for 15 minutes at 3,800 rpm in a microcentrifuge. Columns were then inverted and 30 µl of TE buffer was added before the columns were centrifuged for 2 minutes at 3,800 rpm, with this fraction collected for later use. The Klenow amplified DNA was then used in subsequent DNA manipulations.

The now purified PCR products were then used in a PCR reaction with an oligonucleotide comprising the following sequence:

5'-GAGAGAATTCAGGTCAGACTACAAGGACGACGACGACAAG-3' (SEQ ID NO: 35), wherein an EcoRI restriction endonuclease site is shown in bold text, and three stop codons are underlined. Note that each of the stop codons is in a different reading frame.

Thus, the following PCR reaction was used:

| Oligonucleotide comprising SEQ ID NO: 35 (10 µM) | 12 µl |
|Ced buffer | 5 µl |
| dNTP (2 mM) | 5 µl |
| Taq polymerase (Boehringer) 5.5 U/µl | 0.4 µl |
| H₂O | 26.6 µl |
| Klenow amplified DNA | 2 µl |

Reactions were then cycled in a thermocycler using the following program:

95° C. for 2 min; 60° C. for 30 sec; 72° C. for 1 min;
95° C. for 20 sec; 60° C. for 30 sec; 72° C. for 1 min (repeated 29 times); and
72° C. for 5 min.

PCR products were then purified using Amicon spins columns.

Figure 2:
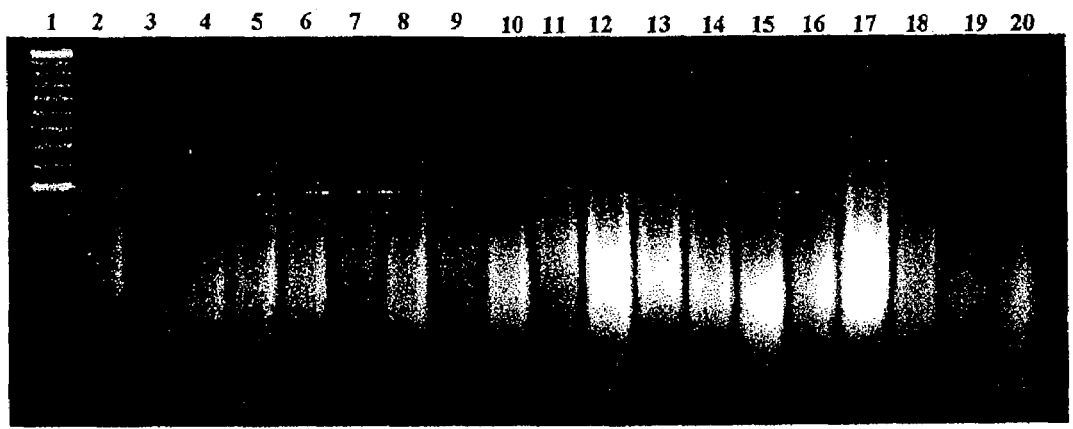
FIG. 2 is a photographic representation showing amplification products of random PCR amplification of genomic DNA isolated from *Archaeoglobus fulgidis, Aquifex aeliticus, Aeropyrum pernix, Bacillus subtilis, Bordetella pertussis* TOX6, *Borrelia burgdorferi, Chlamydia trachomati, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii,* Synechocystis PCC 6803, *Thermoplasma volcanium,* and *Thermotoga maritima.* The molecular weight marker is shown on the far left.

The PCR products were then analyzed by electrophoresis on standard TAE-agarose gels to determine the approximate size of the nucleic acid fragments generated as shown in FIG. 2. The nucleic acid concentration of the samples was also determined.

PCR products from each of the 19 bacterial species were then pooled to generate a biodiverse nucleic acid library. To do so, DNA from each organism was added in an equimolar amount when compared to the amount of nucleic acid added to the pool from the organism with the smallest genome. Between 1 µg and 10 µg of DNA from each organism was used, depending on the genome size of the organism from which the DNA was obtained.

Figure 3:
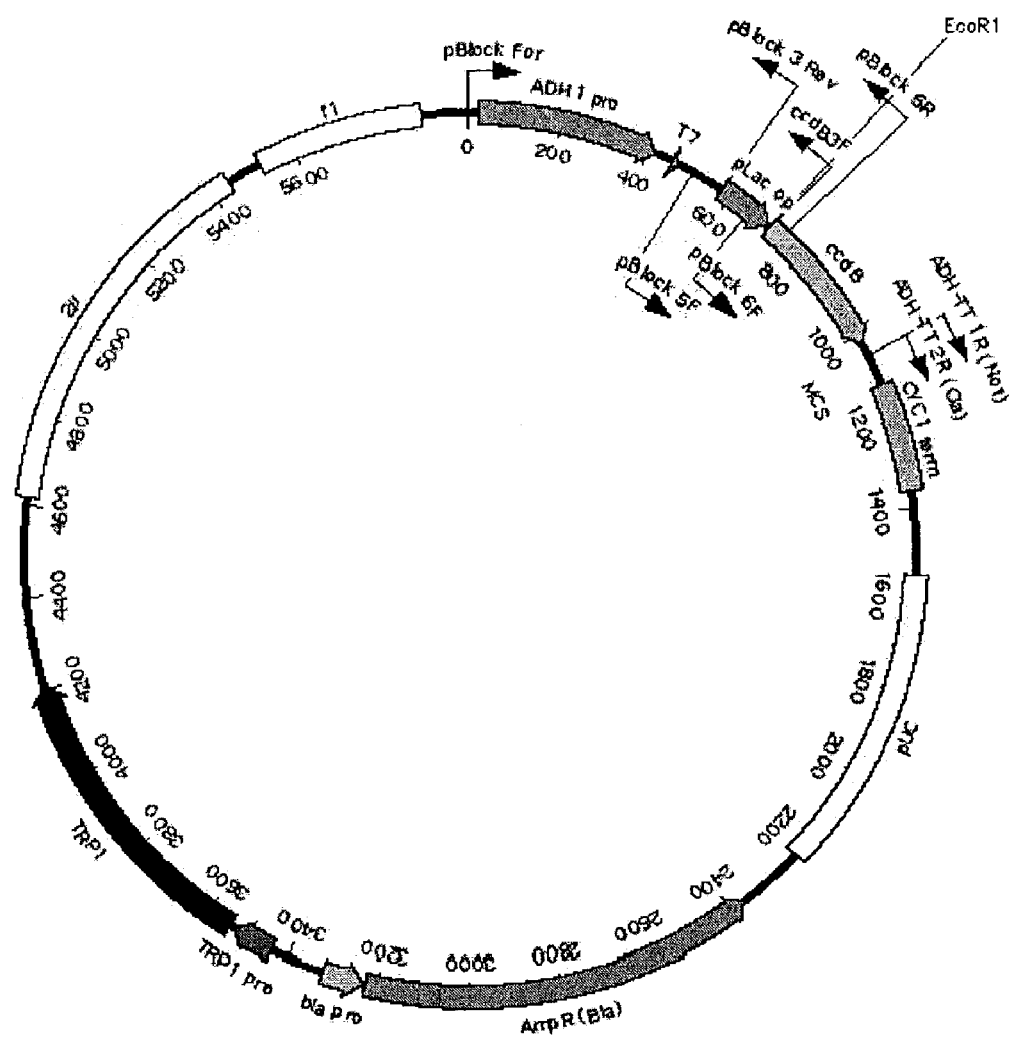
FIG. 3 is a schematic representation of the pDEATH-Trp vector (SEQ ID NO: 36). The pDEATH-Trp vector comprises a minimal ADH promoter for constitutive expression of a nucleic acid inserted into the vector in yeast cells; a T7 promoter for expression of a nucleic acid fragment in bacterial cells; a nucleic acid encoding a SV-40 nuclear localization signal to force any expressed polypeptide into the nucleus of a yeast cell; a CYC1 terminator, for termination of transcription in yeast cells; a nucleic acid encoding a peptide conferring ampicillin resistance, for selection in bacterial cells; a nucleic acid encoding TRP1 which allows auxotrophic yeast to grow in media lacking tryptophan; a pUC origin of replication, to allow the plasmid to replicate in bacterial cells; and a 2µ origin of replication, to allow the plasmid to replicate in yeast cells.

In order to allow efficient cloning of the nucleic acid fragments into the pDEATH-Trp vector (SEQ ID NO: 36; FIG. 3), both the fragments and the vector were digested with the EcoRI restriction endonuclease. Restriction digests were completed in the following reactions:

Digestion of PCR products used the following reaction conditions:

| PCR products (1 µg) | |
| --- | --- |
| EcoR I Buffer (Promega) | 17 µl |
| BSA (10x) | 17 µl |
| EcoR I enzyme (20 U/µL) (Promega) | 0.9 µl |
| H₂O | to 170 µl |

Restriction digests were allowed to proceed for 40 minutes at 37° C. Samples were then purified using QIAquick PCR purification columns as per manufacturer's instructions. Nucleic acid was eluted into 50 µl of H₂O.

Digestion of pDEATH-Trp vector used the following reaction conditions:

| pDEATH-Trp (25 µg) | |
| --- | --- |
| EcoR I Buffer (Promega) | 100 µl |
| BSA (10X) | 100 µl |
| EcoR I enzyme (20 U/µL) | 4 µl |
| H₂O | to 1000 µl |

Restriction digests were allowed to proceed for 5 minutes at 37° C. Samples were then purified using 3 QIAquick PCR purification columns as per manufacturer's instructions. Nucleic acid was eluted into 150 µl of H₂O.

The fragments generated from the PCR products were then ligated into the pDEATH-Trp vector (SEQ ID NO 36) using the following reaction:

pDEATH-Trp (2 µg)

BGF-PCR Fragments (1 µg)

| Ligation Buffer (10x) (NEB) | 20 µl |
| --- | --- |
| T4 DNA Ligase (NEB) | 10 µl |
| H₂O | to 200 µl |

Ligation reactions were allowed to proceed overnight at 16° C. The ligase was then heat inactivated by incubating the samples at 65° C. for 30 minutes. Following completion of the ligation reaction sample volumes were increased to 500 µl with TE buffer and added to an Amicon spin column. These columns were then centrifuged for 15 minutes at 3,800 rpm in a microcentrifuge. Columns were then inverted and 30 µl of TE buffer was added before the columns were centrifuged for 2 minutes at 3,800 rpm, with this fraction collected for later use.

Figure 4:
FIG. 4 is a photographic representation showing nucleic acid fragments isolated from bacterial clones carrying the pDEATH-Trp vector. The isolated vector was digested with the restriction endonuclease EcoRI and the resulting fragments electrophoresed. The molecular weight marker is shown on the far left and far right, and the text indicates the size range of the nucleic acid fragments in base pairs.

The pDEATH-Trp vector containing the biodiverse nucleic acid fragment was then transformed into *E. coli* TOP10 cells. Expression vectors were then isolated from bacteria using standard procedures. Restriction enzyme digestion of the isolated vectors using EcoRI was then used to characterise the size of the inserts contained in the library, as shown in FIG. 4.

Vectors were then pooled and transformed into the yeast strain PRT 51. Yeast strain PRT-51 is characterized by the following genotype: MATα, his3, trp1, ura3, 6 LexA-LEU2, lys2:3 clop-LYS2, CYH2$^R$, ade2:G418-pZero-ade2, met15:Zeo-pBLUE-met15, his5::hygro.

The result of this transformation was a library of 61 million clones. The recombinant clones each express a peptide that is fused to another polynucleotide sequence encoding the FLAG epitope or other marker.

EXAMPLE 2

Characterization of a Biodiverse Nucleic Acid Fragment Expression Library in the pDEATH-Trp Vector Sequence analysis of nucleic acids cloned into pDEATH-Trp vector show that the fragments are derived from a variety of organisms, and encode a variety of proteins, as shown in Table 2.

TABLE 2

Characterization of nucleic acid fragment cloned into pDEATH-Trp

| No. | Insert size (bp) | Organism | Genbank ID | Function |
|---|---|---|---|---|
| 1 | 114 | P. aeruginosa | AAG05339.1 | Hypothetical Protein |
| 2 | 143 | Synechocystis PCC6803 | BAA10184.1 | Fructose |
| 3 | 166 | E. coli | AAC73742.1 | Lipoprotein |
| 4 | 180 | B. subtilis | CAB12555.1 | methyl-accepting chemotaxis protein |
| 5 | 150 | N. meningitis | AAF41991.1 | N utilization substance protein A |
| 6 | 240 | E. coli | AAC75637.1 | Hypothetical protein |
| 7 | 357 | H. pylori | AAD08555.1 | transcription termination factor NusA |
| 8 | 83 | Z. maritima | AAD36283.1 | Hypothetical protein |

EXAMPLE 3

Screening of a Biodiverse Nucleic Acid Fragment Library for Inhibitors of the Interaction Between the Polymyositis-Scleroderma Autoantigen (SCL) and Basic Helix-Loop-Helix Transcription Factor E47.

Figure 5:
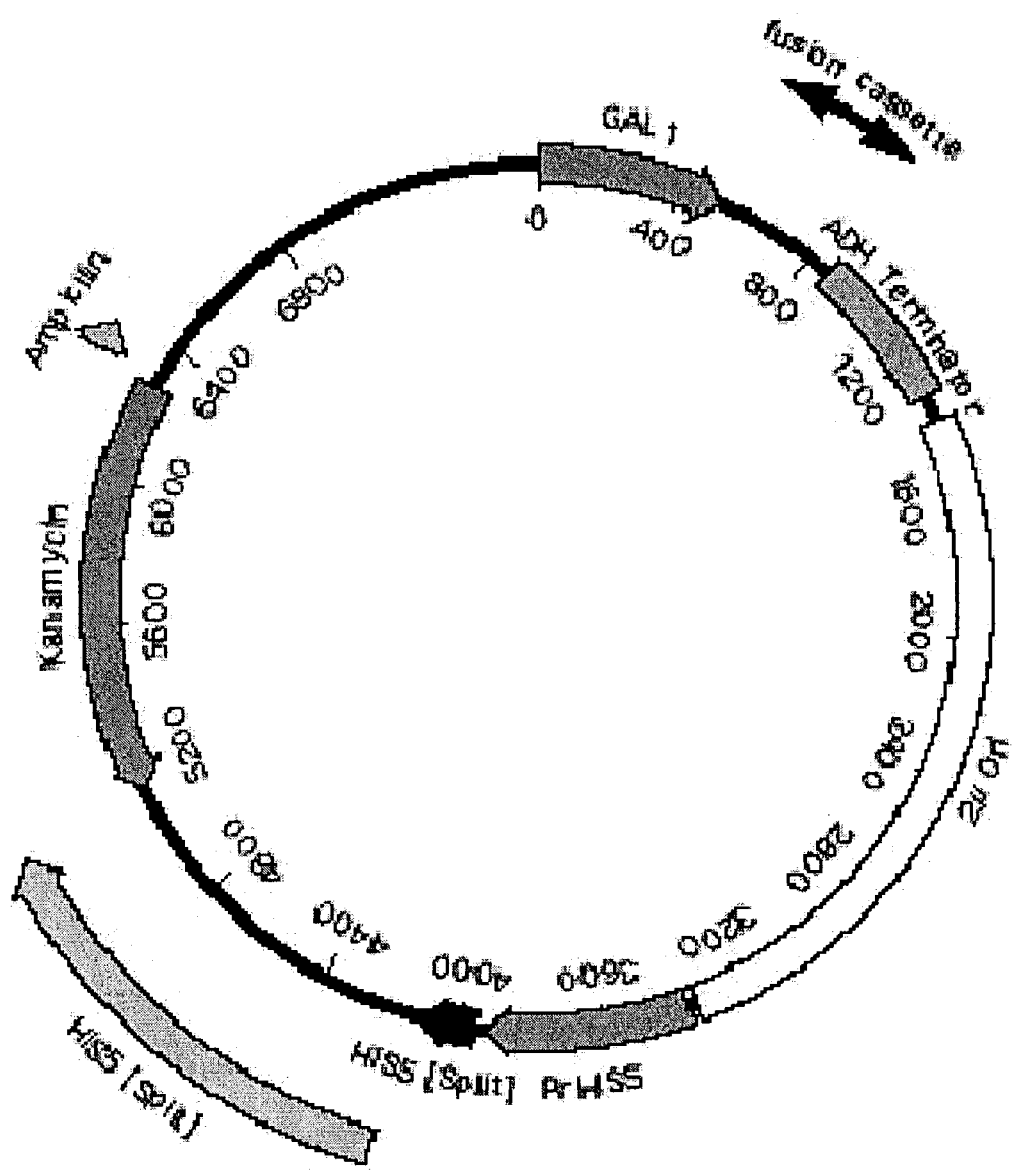
FIG. 5 is a schematic representation of the pJFK vector (SEQ ID NO: 60). The pJFK vector comprises a GAL1 promoter for inducible expression of a nucleic acid fragment in yeast cells; a nuclear localization signal to force any expressed polypeptide into the nucleus of a yeast cell; a nucleic acid encoding an activation domain derived from the B42 protein, to be expressed as a fusion with a polypeptide of interest in a "n"-hybrid screen; an ADH terminator or termination of transcription in yeast cells; a 2µ origin of replication, to allow the plasmid to replicate in yeast cells; an HIS5 gene to allow auxotrophic yeast to grow in media lacking histidine; a nucleic acid encoding a peptide conferring ampicillin resistance, for selection in bacterial cells; and a nucleic acid encoding a peptide conferring kanamycin resistance.
Figure 6:
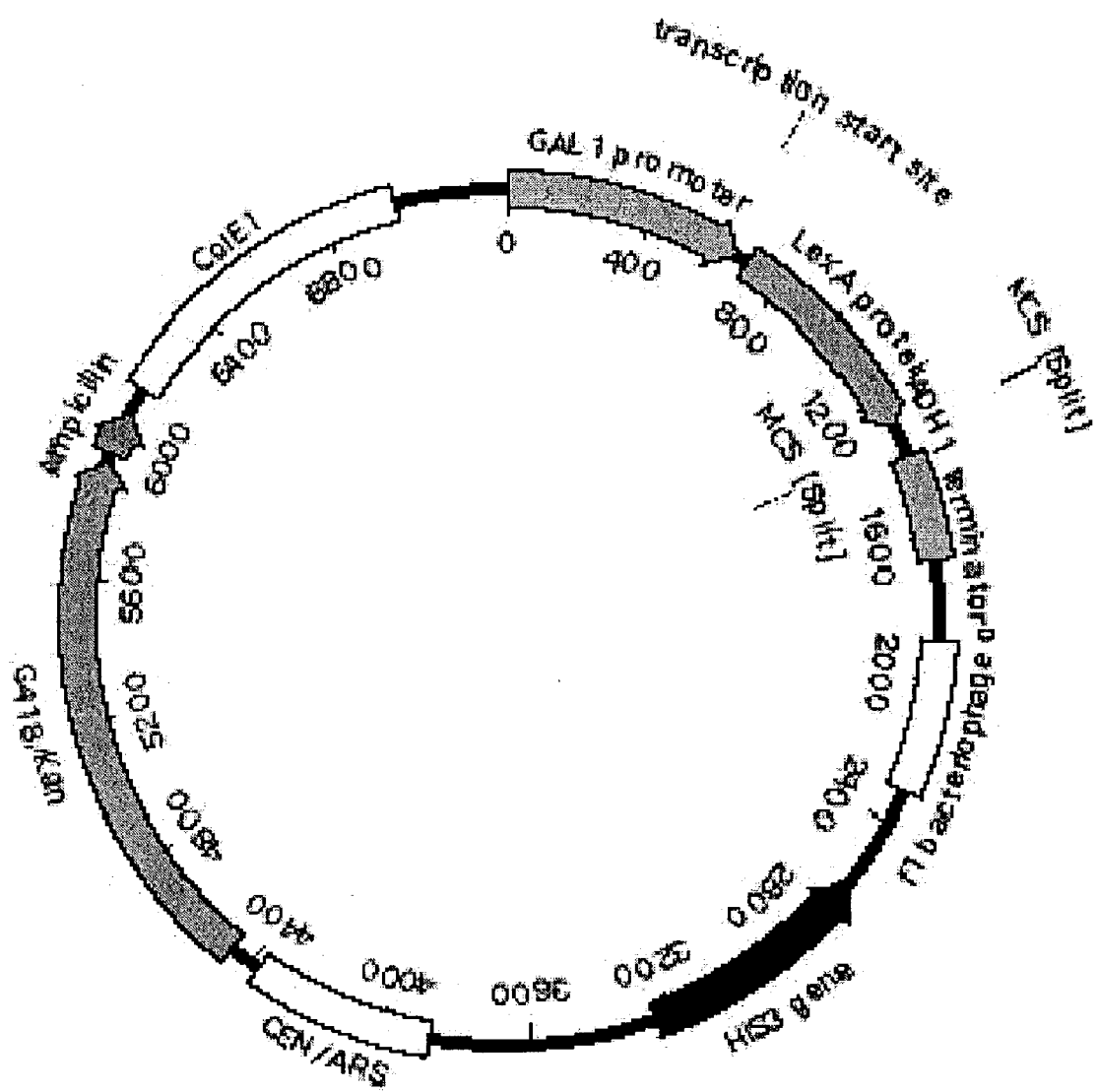
FIG. 6 is a schematic representation of the pDD vector (SEQ ID NO: 61). The pDD vector comprises a GAL1 promoter for inducible expression of a nucleic acid fragment in yeast cells; a nucleic acid encoding a LEXA1 protein, to be expressed as a fusion with a polypeptide of interest in a "n"-hybrid screen; an ADH terminator or termination of transcription in yeast cells; a 2µ origin of replication, to allow the plasmid to replicate in yeast cells; an HIS5 gene to allow auxotrophic yeast to grow in media lacking histidine; a nucleic acid encoding a peptide conferring ampicillin resistance, for selection in bacterial cells; and a nucleic acid encoding a peptide conferring kanamycin resistance.

Nucleic acid encoding the SCL protein was cloned into the prey vector pJFK (SEQ ID NO: 60; FIG. 5) in operable connection with a nuclear localisation signal, and a B42 activation domain. The nucleic acid encoding the E47 protein was cloned into the bait vector pDD (SEQ HD NO: 61; FIG. 6) in operable connection with the LexA DNA binding domain. The pDD vector also contains a nucleic acid encoding the HIS3 gene (FIG. 6).

These vectors were transformed into the PRT 480 yeast strain (which contains two LexA-CYH2 chimeric reporter genes and two LexA-URA3 counter selectable reporter genes).

Figure 7:
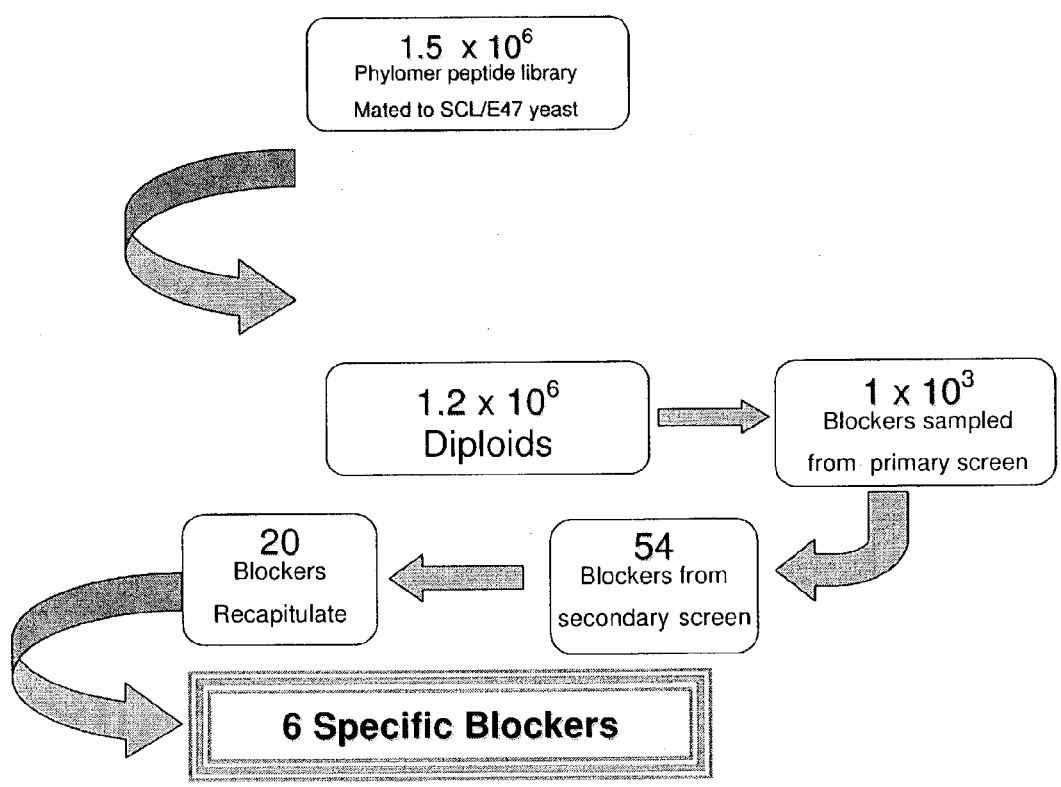
FIG. 7 is a schematic representation of a reverse two-hybrid screen to identify antagonists of the interaction of SCL/E47. Initially, yeast expressing a library of the present invention is mated to a yeast strain expressing E47 and SCL. From this screen 1000 clones were chosen that were able to grow on FOA plates. These were then screened to identify those clones that were not able to grow on LEU-plates. The plasmids that expressed putative antagonists of the SCL/E47 interaction were then isolated and re-transformed into yeast to confirm their ability to block such an interaction.

The process of screening the library is represented schematically in FIG. 7. Briefly, the PRT 480-SCL/E47 bait prey haploid strain was grown to high density in complete synthetic media lacking histidine and uracil (ie., HU media) and supplemented with 0.03% (w/v) galactose/2% (w/v) raffinose and then mass-mated with the PRT 51-library strain produced as described in Example 1. Approximately 300,000 diploids were plated onto 30 cm plates containing complete synthetic media lacking histidine and tryptophan (ie., HW media), and supplemented with 0.06% (w/v) galactose/0.04% 5-FOA and glucose.

After growth of these plates at 30° C. for 2-3 days, 1000 FOA-resistant colonies were isolated and plated onto a master-plate of complete synthetic media lacking histidine and tryptophan (ie., HW media). These cells potentially expressed peptide antagonists (ie., blockers) that prevent the SCL/E47 interaction, however may also include cells that had shut down expression of the URA3 reporter genes, such as, for example, by epistasis.

Figure 8:
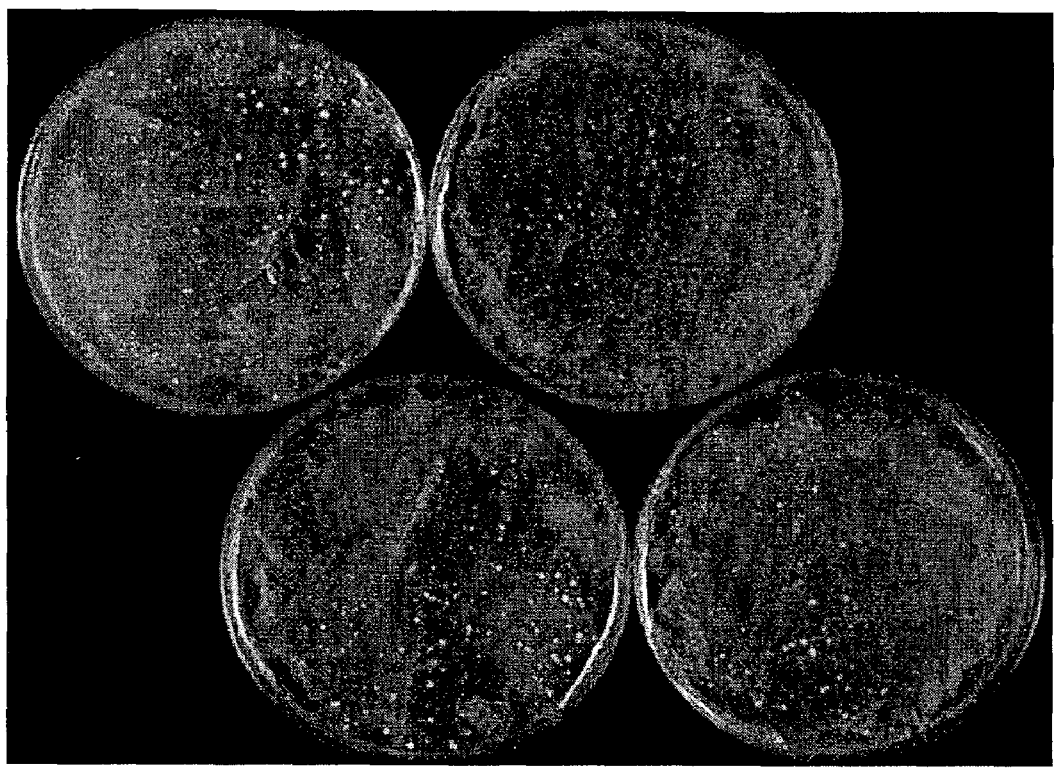
FIG. 8 is a photographic representation showing library clones that have not expressed the URA3 counter selectable marker gene on yeast 0.04% FOA plates, and are able to grow on 5-FOA.

Results of this primary reverse two-hybrid screen are shown in FIG. 8.

The FOA-resistant colonies were replica-plated from the master-plate onto plates containing HWU media, or media lacking histidine, tryptophan and leucine (ie. HWL media). The replica-plate media also contained various concentrations of galactose. By modulating the level of galactose in the media, we were able to discriminate between yeast cells expressing genuine peptide blockers as opposed to those cells that had shut down expression of the URA3 reporter genes, such as, for example, by epistasis.

Figure 9:
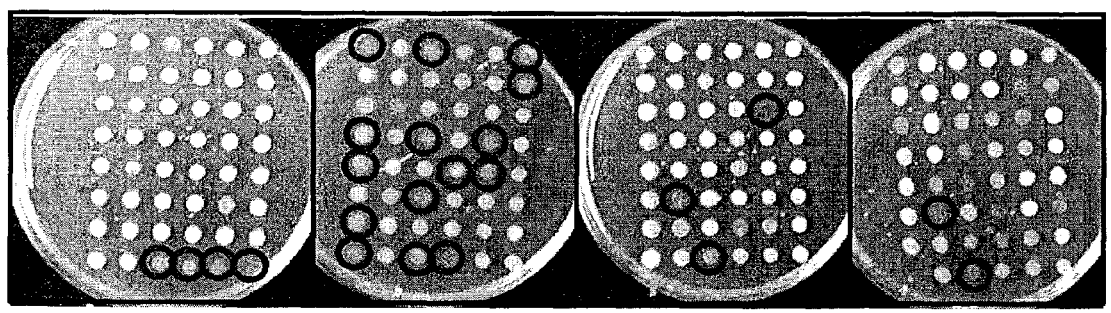
FIG. 9 is a photographic representation showing yeast colonies isolated from an initial reverse two-hybrid screen grown on media lacking leucine. The circled colonies are those that are not expressing the LEU2 selectable marker. Accordingly, it appears that these colonies express a peptide that inhibits the interaction of SCL and E47.

Results of this secondary screen are shown in FIG. 9. In summary, 54 colonies (6% of FOA-resistant colonies) were isolated from this screen.

Yeast colonies that exhibited reduced growth on leucine-containing media were selected and a library plasmid was rescued from each colony. Those plasmids that were from cells wherein the SCL/E47 interaction was antagonized or inhibited were sequenced.

Library plasmids were re-transformed into strain PRT51, and the resultant yeast cells were again mated with strain PRT 480 SCL/E47 haploids. Diploids were re-screened for their ability to block the SCL/E47 interaction, by plating in the forward direction on plates containing HWU or HWL media supplemented with various concentrations of galactose. The ability of a particular plasmid to recapitulate the blocked phenotype was determined.

Figure 10:
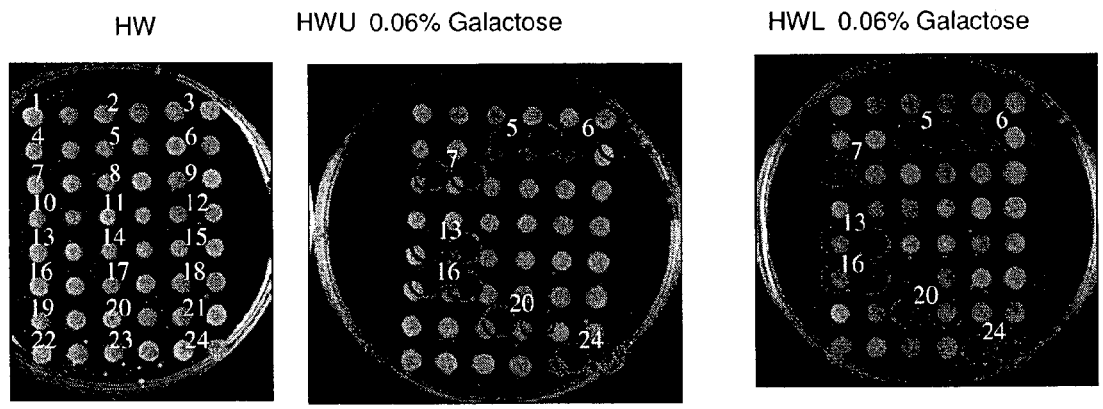
FIG. 10 is a photographic representation of yeast colonies expressing the E47 bait and SCL prey proteins in addition to putative peptide inhibitors identified in a reverse two-hybrid screen. These were tested for blocking of the interaction through growing the colonies on media lacking uracil and media lacking leucine. In this way any putative peptide inhibitors were re-tested for the ability to block the interaction between SCL and E47.

Data shown in FIG. 10 indicate that, for 54 colonies tested, the interaction between SCL and E47 was again inhibited in 26 clones (ie. 2% of FOA-resistant colonies).

Seven clones were found to recapitulate the blocking of an interaction between SCL and E47 twice.

Subsequently, the specificity of blocking was assayed, by mating those strains that did recapitulate the blocked phenotype into a strain PRT480 expressing two interacting proteins selected from the group consisting of: (i) E2,2 2F and SCL; and (ii) ID and E47. The E2-22F protein is a helix-loop-helix protein that is capable of forming heterodimers with other helix-loop-helix proteins, such as, for example, SCL. The ID protein is another helix-loop-helix protein, which has been shown to bind E47 and inhibit the ability of E47 to bind DNA.

Of the 26 colonies tested, the interaction between SCL and E47 was specifically blocked in 6 colonies (Table 3).

TABLE 3

Specificity of antagonism of the SCL/E47 interaction

| Clone Number | Predicted fusion peptide size | Target interaction[1] SCL/E47 | SCL/E2.22F | Id1/E47 |
|---|---|---|---|---|
| BGF 05 | 55 | + | + | + |
| BGF 06 | 24 | + | − | − |
| BGF 13 | 10 | + | − | − |
| BGF 30 |  | + | − | − |
| BGF 24 | 26 | + | − | − |
| BGF 35 | 63 | + | − | − |
| BGF 51 |  | + | − | − |

[1]+, the interaction was blocked; −, the interaction was not blocked.

The plasmids were isolated from these clones and either the nucleic acid sequence or the predicted peptide sequence of 4 of these clones was analyzed using the BLAST program available from NCBI.

The results of this analysis are represented in Table 4. Data indicate that we have isolated 6 specific peptide blockers of the interaction of SCL and E47 from a sample screen of a library containing 1×10$^6$ independent clones, there being considerable sequence divergence observed between those peptides blockers. None of the peptide blockers identified was merely performing its native function. Based upon the frequency of peptide blockers identified per library clone, it is estimated that the method described herein is about 100-fold more efficient than a screen of a peptide aptamer library.

TABLE 4

Characterization of the antagonists of the SCL/E47 interaction

| Clone | Nucleotide sequence of first forward ORF in clone | Amino acid sequence of fusion peptide encoded by first forward ORF in clone | Nucleotide sequence of inserted nucleic acid fragment in clone | Amino acid sequence encoded by fragment | Genome from which fragment was isolated | Protein deduced to be encoded by fragment in native content (1) |
|---|---|---|---|---|---|---|
| BGF 05 | SEQ ID NO: 62 | SEQ ID NO: 63 | SEQ ID NO: 64 | SEQ ID NO: 65 | H. influenzae | β-ketoacyl-ACP synthase III |
| BGF 06 | SEQ ID NO: 66 | SEQ ID NO: 67 | SEQ ID NO: 68 | SEQ ID NO: 69 | A. aeolicus | glutamyl-tRNA synthetase |
| BGF 13 | SEQ ID NO: 70 | SEQ ID NO: 71 | SEQ ID NO: 72 | SEQ ID NO: 73 | H. influenzae | DNA repair protein (radA) |
| BGF 24 | SEQ ID NO: 74 | SEQ ID NO: 75 | SEQ ID NO: 76 | SEQ ID NO: 77 | T. maritima | response regulator TM0143 |
| BET 35 | SEQ ID NO: 78 | SEQ ID NO: 79 | SEQ ID NO: 80 | SEQ ID NO: 81 | H. influenzae | beta-ketoacyl-ACP synthase III (fabH) |

(1) Native function was obtained by BLAST analysis of the nucleotide sequence of the nucleic acid fragment in each clone.

EXAMPLE 4

The Construction of a Biodiverse Nucleic Acid Fragment Expression Library in the Vector T7Select415-1

Nucleic acid was isolated from the following bacterial species:

| 1 | Archaeoglobus fulgidis |
| 2 | Aquifex aeliticus |
| 3 | Aeropyrum pernix |
| 4 | Bacillus subtilis |
| 5 | Bordetella pertussis TOX6 |
| 6 | Borrelia burgdorferi |
| 7 | Chlamydia trachomatis |
| 8 | Escherichia coli K12 |
| 9 | Haemophilus influenzae (rd) |
| 10 | Helicobacter pylori |
| 11 | Methanobacterium thermoautotrophicum |
| 12 | Methanococcus jannaschii |
| 13 | Mycoplasma pneumoniae |
| 14 | Neisseria meningitidis |
| 15 | Pseudomonas aeruginosa |
| 16 | Pyrococcus horikoshii |
| 17 | S nechosistis PCC 6803 |
| 18 | Thermoplasma volcanium |
| 19 | Thermotoga maritima |

Nucleic acid fragments were generated from each of these genomes using multiple consecutive rounds of PCR using tagged random oligonucleotides.

In the final round of PCR, the sequence of the oligonucleotide primer comprised the sequence:
5'-AGAGGAATTCAGGTCAGACTACAAGGAC-GACGACGACAAG-3' (SEQ ID NO: 37).

The PCR products generated were then used as a template for PCR reactions using the following oligonucleotides:

(SEQ ID NO: 38)
5'-CAGAAGCTTAAGGACGACGACGACAAG-3';

(SEQ ID NO: 39)
5'-CAGGAATTCAAGGACGACGACGACAAG-3';

(SEQ ID NO: 40)
5'-CAGGAATTCCAAGGACGACGACGACAAG-3';
and (SEQ ID NO: 41)
5'-CAGGAATTCACAAGGACGACGACGACAAG-3', wherein the underlined sequence in SEQ ID Nos: 37-41 permits amplification of the PCR products. Furthermore, the sequence shown in bold highlights a HindIII restriction endonuclease recognition site or EcoRI recognition site. Furthermore, note the addition of one or two nucleotides after the EcoRI restriction site in SEQ ID Nos: 40 and 41, respectively (shown in italics). These nucleotides allow expression of amplified nucleic acid in multiple forward reading frames.

Each DNA template was amplified by "one armed" (ie. using only 1 oligonucleotide primer) PCR, with each of the oligonucleotides (ie., SEQ ID Nos: 38-41) in separate reactions (ie. 76 reactions).

Each PCR reaction contained:

| Template DNA | 1 μl |
| Taq buffer (10x) (Promega) | 5 μl |
| MgCl$_2$ (25 mM) | 4 μl |
| dNTP (2 mM) | 5 μl | a primer selected from the group consisting of

| SEQ ID Nos: 38–41 (10 pmol/μl) | 10 μl |
| Taq DNA polymerase (Promega 5 U/μl) | 0.4 μl |
| H$_2$O | to 50 μl |

Reactions were then cycled in a Perkin Elmer thermocycler PE 9700 or PE 2400 using the following program:
5 min at 94° C., followed by 30 cycles wherein each cycle consists of 30 sec at 94° C., followed by 30 sec at 55° C., and followed by 1 min at 72° C.], followed by 5 min at 72° C.

A sample of the resulting PCR products was analyzed by electrophoresis using a 2% agarose/TAE gel. The amount of nucleic acid in each of the PCR products was also determined using the picogreen method following instructions provided by the manufacturer.

PCR products generated with each of the oligonucleotides SEQ ID Nos: 38-41 were pooled. DNA from each organism was added in an equimolar amount when compared to the amount of nucleic acid added to the pool from the organism with the smallest genome.

Subsequently, the pools generated from PCR products amplified using the oligonucleotides SEQ ID NO: 39, SEQ ID NO: 40 or SEQ ID NO: 41 were combined in equal ratios (ie. equal amounts of nucleic acid) to form one pool.

The pooled PCR products were then purified using QIAquick PCR purification columns (QIAGEN) as per manufacturer's instructions. This step removes any unincorporated oligonucleotides, dNTPs and contaminating proteins.

Each of the pools of PCR products (6 µg) was then divided into 3 equal parts and digested with one of the restriction enzymes AluI, HaeII or RsaI (NEB) in the following reaction:

| PCR product (2 µg) | |
| --- | --- |
| Restriction endonuclease buffer (10x) (NEB) | 4 µl |
| Restriction endonuclease | 1 µl |
| H₂O | to 40 µl |

Reactions were allowed to proceed for 2 hours at 37° C., before being heat inactivated by incubating at 65° C. for 20 minutes. Restriction digests were then re-pooled and purified using QIAquick PCR purification columns (QIAGEN) as per manufacturer's instructions.

Each of the enzymes AluI, HaeII and RsaI produce blunt ends. Accordingly, it is possible to ligate blunt end adaptors to the restriction digested PCR products to allow directional cloning into the T7Select415-1 vector. Oligonucleotides encoding the blunt-end adaptors were generated comprising the following sequences:

| | |
| --- | --- |
| 5'-AATTCGAACCCCTTCG-3' | (SEQ ID NO: 42) |
| 5'-CGAAGGGGTTCG-3' | (SEQ ID NO: 43) |
| 5'-AATTCGAACCCCTTCGC-3' | (SEQ ID NO: 44) |
| 5'-GCGAAGGGGTTCG-3' | (SEQ ID NO: 45) |
| 5'-AATTCGAACCCCTTCGCG-3' | (SEQ ID NO: 46) |
| 5'-CGCGAAGGGGTTCG-3' | (SEQ ID NO: 47) |
| 5'-AGCTCGAAGGGGTTCG-3' | (SEQ ID NO: 48) |
| 5'-CGAACCCCTTCG-3'. | (SEQ ID NO: 49) |

The adaptor pairs SEQ ID Nos: 42 and 43; SEQ ID Nos: 44 and 45; SEQ ID NOs: 46 and 47; SEQ ID NOs: 48 and 49 were then annealed to one another. This process was completed in H₂O with each of the oligonucleotides at a concentration of 50 µM. Pairs of adaptors were incubated at 94° C. for 10 minutes and then allowed to cool to room temperature slowly.

The annealed adaptors were then ligated to the pool of amplified PCR products in separate ligation reactions. The adaptor formed through annealing of SEQ ID NOs: 48 and 49 was ligated to the pool of PCR products amplified using the oligonucleotides set forth in SEQ ID NO: 39, SEQ ID NO: 40 and SEQ ID NO: 41.

Ligations were carried out in the following reactions:

| | |
| --- | --- |
| Pooled PCR product (average length of 200 bp) | 2 pmol |
| Annealed adaptor | 150 pmol |
| Ligation buffer (10x) (Promega) | 1 µl |
| T4 DNA ligase (3U/µl) (Promega) | 1 µl |
| H₂O | to 10 µl |

Samples were then incubated at 4° C. overnight before being heat inactivated through incubation at 65° C. for 20 minutes.

Samples were then phosphorylated using T4 polynucleotide kinase (Promega) in the following reaction:

| | |
| --- | --- |
| Ligation buffer (10x) (Promega) | 1 µl |
| rATP (10 mM) | 2 µl |
| T4 polynucleotide kinase (5 U/µl) | 1 µl |
| H₂O | 20 µl |

Samples were incubated at 37° C. for 30 minutes followed by incubation at 65° C. for 20 minutes to heat inactivate the T4 polynucleotide kinase.

Following ligation and phosphorylation each of the three reactions comprising nucleic acid amplified using the oligonucleotide SEQ ID NO: 38 were combined in equal ratios, ie. equal amounts of nucleic acid to form one pool.

The nucleic acids originally amplified with SEQ ID NO: 38 were then digested with the restriction endonuclease HindIII in the following reaction:

| PCR product (2 µg) | |
| --- | --- |
| HindIII buffer (10x) (Promega) | 8 µl |
| HindIII (10 U/µl) (Promega) | 1 µl |
| H₂O | to 80 µl |

The nucleic acids in the pool originally amplified by one of SEQ ID Nos: 39-41 were digested with the restriction endonuclease EcoRI in the following reaction:

| PCR product (2 µg) | |
| --- | --- |
| EcoRI buffer (10x) (Promega) | 8 µl |
| EcoRI (10 U/µl) (Promega) | 1 µl |
| H₂O | to 80 µl |

Samples were then purified using a QIAquick PCR purification column (QIAGEN) as per manufacturer's instructions. Nucleic acid concentration was then determined by spectrophotometry measuring UV absorption at 260 nm.

Both pools of nucleic acid fragments (ie. those digested with EcoRI and those digested with HindIII) were then combined in equal ratios, ie. equal amounts of nucleic acid, to form one pool. This pool of nucleic acid fragments was then suitable for cloning into the peptide display vector T7Select415-1 (Novagen). The T7415-1 vector is provided in a form for nucleic acids to be ligated into EcoRI and HindIII restriction endonuclease sites.

The nucleic acid fragments were then ligated into the T7Select415-1 vector using the following reaction:

| | |
|---|---|
| Ligation buffer (10x) (Novagen) | 0.5 µl |
| rATP (10 mM) | 0.5 µl |
| DTT (10 mM) | 0.5 µl |
| T7Select415-1 EcoRI/HindIII vector arms (0.02 pmol) | 1 µl |
| Nucleic acid fragments (0; 0.02; and 0.06 pmol in independent reactions) | |
| H$_2$O | to 5 µl |

Reactions were incubated at 16° C. overnight.

EXAMPLE 5

Packaging and Amplification of a Biodiverse Nucleic Acid Fragment Expression Library The ligation reactions of Example 3 were packaged using commercial packaging extract available from Novagen. These reactions were then titered according to manufacturer's instructions by infection of *E. coli* BL21 cells. By using 1 µl from each of three independent ligations, titers between $1.3 \times 10^7$ and $7 \times 10^7$ plaque forming units (pfu)/ml were obtained.

Pooling of three ligation reactions containing a total of 1 µg of T7Select415-1 vector, and packaging, resulted in a library with $2.75 \times 10^7$ pfu, ie $2.75 \times 10^7$ initial recombination events. The library was immediately amplified by "plate lysate amplification" (as per manufacturer's instructions) on 180 LB Petri dishes (14 cm diameter). Titers of the amplified lysates varied between 1 and $5 \times 10^{10}$ pfu/ml. Two liters of lysate were harvested, pooled and the titer determined at $1.5 \times 10^{10}$ pfu/ml, ie $3 \times 10^{13}$ pfu in total. The lysate was stored at 4° C. over CHCl$_3$ (as per manufacturer's instructions) and glycerol stocks containing 10% glycerol were stored at −80° C.

EXAMPLE 6

Characterization of a T7-Displayed Biodiverse Nucleic Acid Fragment Library

During the amplification of the library described in Example 4, individual plaques from low-density plates were collected and analyzed by PCR with primers specific to T7Select415-1 of the nucleotide sequence.

Thirty nine plaques with insert sizes larger than 70 bp were analyzed by DNA sequence analysis. The resulting sequences are summarised in the Table 5.

DNA from 13 of the 19 bacterial genomes could be identified in the recombinant phage analyzed,. In most cases, the homology was between 96 and 100% in the regions that were derived from the genomic starting material. In addition, primers and adapters were identified, however, there were also many cases of strings of adapters and multiple PCR primers in the insert regions. The inserted DNA of the analyzed phage clones was up to 250 bp long.

TABLE 5

Characterization of nucleic acid fragments in T7Select-415-1

| BGF clone | T7for/ rev PCR fragment (bp) | Insert homology to organism (% homology in the matching region) | Size of homologous region (bp) | Extra amino Acids after Asn (T7) | Natural reading frame |
|---|---|---|---|---|---|
| 8 | 255 | *B. pertussis (98%)* | 112 | 16 | |
| 14 | 212 | *M. thermoautotrophicum (98%)* | 73 | 12 | |
| 15 | 350 | *B. pertussis (98%)* | 171 | 0 | |
| 16 | 263 | *A. fulgidus (100%)* | 125 | 20 | |
| 18 | 260 | *A. fulgidus (100%)* | 112 | 0 | |
| 31 | 260 | *A. fulgidus (96%)* | 118 | 65 | yes |
| 52 | 240 | *T. volcanicum (100%)* | 39 | 0 | |
| 61 | 272 | *M. jannashii (100%)* | 90 | 12 | |
| 65 | 230 | *N. meningiditis (100%)* | 107 | 0 | |
| 73 | 230 | *C. trachomatis (98%)* | 62 | 10 | |
| 83 | 200 | *B. burgdorferi (100%)* | 46 | 8 | |
| 89 | 411 | *B. subtilis (98%)* | 170 | 15 | |
| 100 | 268 | *P. aeruginosa* | 159 | 11 | |
| 104 | 174 | no match | — | 12 | |
| 125 | 250 | *E. coli K12 (98%)* | 109 | 4 | |
| 126 | 220 | *E. coli K12* | 91 | 6 | |
| 139 | 240 | Synechocystis PCC 6803 (100%) | 109 | 26 | yes |
| 141 | 250 | *E.coli K12* | 126 | 6 | |
| 144 | 170 | no match | — | 15 | |
| 152 | 160 | *E. coli K12 (100%)* | 39 | 13 | |
| 153 | 290 | *C. trachomatis (100%)* | 131 | 7 | |
| 163 | 260 | *C. trachomatis (100%)* | 90 | 5 | |
| 166 | 270 | *E. coli K12 (100%)* | 112 | 20 | |
| 169 | 240 | *M. thermoautotrophicum (100%)* | 112 | 6 | |
| 10 | 180 | no match | — | 7 | |
| 17 | 190 | *M. jannashii* | 68 | 13 | |
| 20 | 190 | *E. coli K12* | 58 | 22 | |
| 25 | 170 | *P. horikoshii* | 40 | 10 | |
| 30 | 200 | *P. aeruginosa* | 54 | 13 | |
| 40 | 190 | no match | — | 24 | |
| 42 | 190 | *B. sublilis* | 44 | 0 | |
| 44 | 250 | *B. burgdorferi* | 130 | 6 | |
| 47 | 210 | *C. trachomatis* | 95 | 13 | |

TABLE 5-continued

Characterization of nucleic acid fragments in T7Select-415-1

| BGF clone | T7for/ rev PCR fragment (bp) | Insert homology to organism (% homology in the matching region) | Size of homologous region (bp) | Extra amino Acids after Asn (T7) | Natural reading frame |
|---|---|---|---|---|---|
| 48 | 200 | Synechocystis PCC 6803 | 82 | 20 | |
| 55 | 180 | nomatch | — | 11 | |
| 64 | 190 | Synechocystis PCC 6803 | 46 | 16 | |
| 82 | 180 | M. thermoautotrophicum | 39 | 8 | |
| 87 | 250 | No match | — | 51 | |
| 134 | 280 | M. thermoautotrophicum | | | |

EXAMPLE 7

Screening a T7 Phage Displayed Biodiverse Nucleic Acid Fragment Library for a Mimotope of FLAG The library of Example 4 was screened to isolate phage displaying peptides that bound to monoclonal antibodies in a similar way as natural peptides would. The monoclonal antibody was adsorbed to a Petri dish and a lysate of the amplified phage library was allowed to bind to the antibody immobilised on the Petri dish. After rigorous washing to remove non-specifically bound phage, the remaining phage was eluted and amplified for additional rounds of selection.

Each Petri dish (Nunc, 3.5 cm diameter) was rinsed twice with distilled water. The target antibody in this case was a mouse monoclonal antibody to the FLAG epitope (α-FLAG M2, Sigma Aldrich). The antibody was diluted in TBS buffer to 20 µg/ml and 500 µl was added per dish. The antibody was allowed to adsorb for 3 to 4 hours at room temperature or at 4° C. overnight. The dish was rinsed three times with TBS buffer and filled with 5% skim milk in distilled water. For blocking the skim milk solution was allowed to bind with gentle rocking for 1 hour at room temperature or at 4° C. overnight. The dish was rinsed five times with double distilled water (ddH$_2$O) and filled with ddH$_2$O until use.

About 3×10$^{10}$ pfu to about 4×10$^{10}$ pfu of amplified T7 phage library (as described in Example 4) was added to the precoated and blocked Petri dish. The volume was increased to 0.5 ml with ddH$_2$O and 10×TBS buffer to obtain 1×TBS as final concentration. For dilute phage suspensions the total volume can be raised to 1.5 ml without loss of binding, however the volume should be kept as small as possible to avoid spillage of phage. The phage suspension was allowed to bind with gentle rocking for 5 hours at room temperature or at 4° C. overnight. The phage suspension was discarded and the dish was washed twice with TBS buffer containing Tween-20. TBS-Tween (1 ml) was added to the dish, and the dish incubated for 10 minutes with gentle shaking. This wash step was repeated twice more, without shaking. Bound phage were eluted with 0.5 ml of 1% SDS. The 1% SDS was added to the plates and the plates incubated for 30 minutes with gentle shaking. The eluate was transferred into a reaction tube and the phage titer determined.

For further rounds of biopanning the eluate was amplified in a 10-40 ml culture. A fresh culture of E. coli BL21 in LB medium was grown at 37° C. to an optical density of 0.5 and infected 1:200 with eluate. The culture was shaken at 37° C. for 1 to 2 hours until lysis was observed. The culture was centrifuged at 8000 g for 10 minutes at 4° C. to pellet remaining E. coli cells and cell debris. The supernatant was transferred into a fresh tube, titered and stored over CHCl$_3$ at 4° C. until use.

Three consecutive rounds of biopanning were completed and a binding rate for each round was determined. These binding rates are described in Table 6 below:

TABLE 6

| Panning antibody | Round | Input (pfu) | Output (pfu) | Binding rate |
|---|---|---|---|---|
| αFLAG ab | 1 | 4 × 10$^9$ | 5.5 × 10$^5$ | 0.014 |
| αFLAG ab | 2 | 4 × 10$^9$ | 2.3 × 10$^8$ | 5.7 |
| αFLAG ab | 3 | 4 × 10$^9$ | 1.6 × 10$^9$ | 40 |

Figure 11:
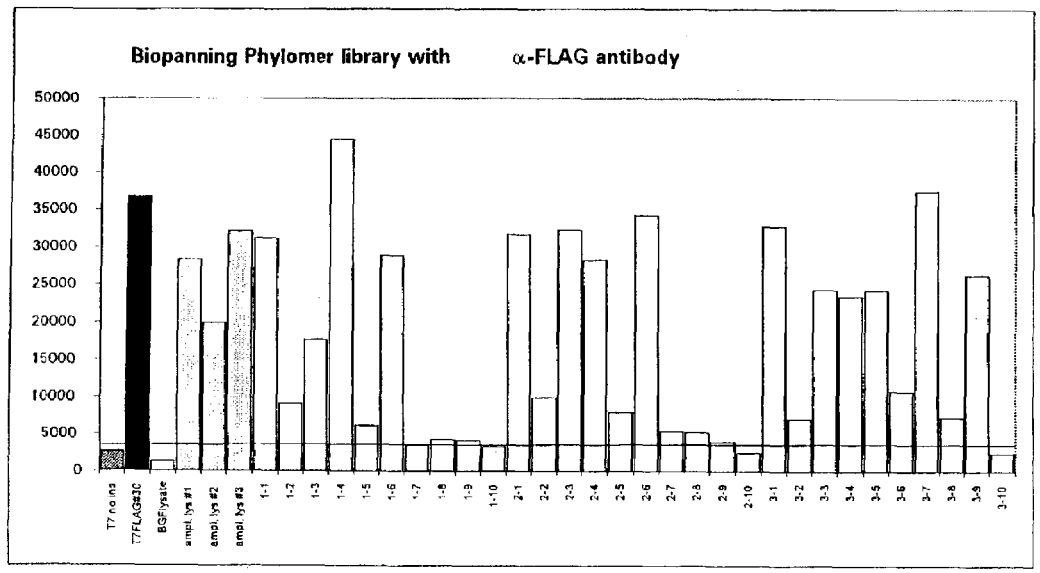
FIG. 11 is a graphical representation of the binding of phage-displayed peptides to the α-FLAG antibody using time resolved fluorescence analysis using a europium detection system. The column marked "T7-no insert" refers to a phage carrying a phage display vector with no insert. "T7 FLAG" refers to a phage displaying the FLAG epitope, ie. a positive control. The column marked "BGF lysate" refers to a pool of random phage from the entire phage displayed library, and the columns marked "Amp1. Lys #1-3 refer to pools of phage isolated following consecutive rounds of biopanning with the α-FLAG antibody. The remaining columns show the ability of individual phage displayed peptides to bind to the α-FLAG antibody, with the first number referring to the round of biopanning from which the phage was isolated, and the second number the clone number.

The binding rate increased from 0.014% in the first round of biopanning to 40% in the third round indicating enrichment of T7 phage clones with a specificity for the panning antibody. Ten individual plaques from each round of biopanning were grown up and analyzed by TRF ELISA with ax FLAG antibody coated wells (100 ng/well). Sixty percent of the clones from the first two rounds and 90% of the clones from the third round of biopanning showed a strong positive signal (FIG. 11). The same clones were tested in an ELISA coated with a monoclonal antibody to papain (3D5) and showed no significant signal. This indicates that the isolated phage clones were specific to the α-FLAG antibody.

As a positive control, oligonucleotides were designed to generate a DNA fragment with EcoRI and HindIII overhangs for cloning into T7Select415-1 EcoRI/HindIII vector arms, in addition to encoding the FLAG epitope (Asp-TyrLysAspAspAspLys; SEQ ID NO: 50). These oligonucleotides comprised the sequences:

(SEQ ID NO: 51)
5'-AATTCCGACTACAAGGACGACGATGACAAGA-3'

(SEQ ID NO: 52)
5'-AGCTTCTTGTCATCGTCGTCCTTGTAGTCGG-3'

The oligonucleotides comprising SEQ ID NO: 51 and SEQ ID NO: 52 were allowed to anneal as previously described before being ligated into the T7Select415-1 EcoRI/HindIII vector arms as described in Example 3.

FIG. 11 shows the binding of phage-displayed peptides to the α-FLAG antibody using time resolved fluorescence analysis using a europium detection system.

EXAMPLE 8

Screening a T7 Phage Displayed Biodiverse Nucleic Acid Fragment Library for a Mimotope of the Pollen Antigen DerpI The library of Example 4 is screened to isolate phage-displaying peptides, which bind to a monoclonal antibody to the major dustmite allergen DerpI, in a similar way as the natural peptide would. The monoclonal antibody is adsorbed to a Petri dish and a lysate of the amplified phage library allowed to bind to the antibody immobilised on the Petri dish. After rigorous washing to remove non-specifically bound phage, the remaining phage is eluted and amplified for additional rounds of selection.

Each Petri dish (Nunc, 3.5 cm diameter) is rinsed twice with distilled water. The target antibody in this case is a mouse monoclonal antibody that binds to the dust mite allergen Der P I (Chapman et al, *Journal of Immunology*, 133(5), 2488-2495, 1984). The antibody is diluted in TBS buffer and allowed to adsorb for 3 to 4 hours at room temperature. The dish is then rinsed three times with TBS buffer. Dishes are blocked overnight at 4° C. with 5% skim milk in distilled water, before being rinsed five times with double distilled water (ddH$_2$O) and filled with ddH$_2$O until use.

About $3 \times 10^{10}$ pfu to about $4 \times 10^{10}$ pfu of amplified T7 phage library (as described in Example 4) is added pre-prepared Petri dish and the volume increased to 0.5 ml with TBS to obtain 1×TBS as final concentration. The phage suspension is allowed to bind with gentle rocking at 4° C. overnight. The dish is washed twice with TBS buffer containing 0.1% Tween-20. 1 ml of TBS-Tween is added to the dish, and the dish incubated for 10 minutes with gentle shaking. This is repeated twice more. 1% SDS is added to elute any bound phage.

For further rounds of biopanning the eluate is amplified in a 10-40 ml culture. A fresh culture of *E. coli* BL21 in LB medium is grown at 37° C. to an optical density of 0.5 at and infected 1:200 with eluate. The culture is shaken at 37° C. for 1 to 2 hours until lysis was observed. The culture is then centrifuged at 8000 g for 10 minutes at 4° C. to pellet remaining *E. coli* cells and cell debris. The supernatant is then transferred into a fresh tube, titered and stored over CHCl$_3$ at 4° C. until use.

EXAMPLE 9

Development and Screening of a Biodiverse Nucleic Acid Fragment Library for Anti-Parasitic Peptides in Drug Resistant *C. elegans*

The modified biodiverse nucleic acid fragment library developed in Example 4 is digested with the restriction enzymes EcoRI and HindIII in the following reaction:

| Biodiverse nucleic acid fragment library (3 µg) | |
|---|---|
| EcoRI buffer (10x) (Promega) | 8 µl |
| BSA (10x) | 8 µl |
| EcoRI (20 U/µl) (Promega) | 3 µl |
| HindIII (10 U/µl) (Promega) | 3 µl |
| H$_2$O | to 80 µl |

Reactions proceed at 37° C. for 2 hours, before enzymes are heat inactivated by incubating the reactions at 65° C. for 20 minutes. Reactions are then electrophoresed in a 2% TAE/agarose gel and the bands relating to the nucleic acid fragments isolated using a QIAquick gel extraction kit (QIAGEN).

At the same time the pGEMEX-1 bacterial expression vector (Promega) is also digested with EcoRI and HindIII in the following reaction:

| pGEMEX-1 (2 µg) | |
|---|---|
| EcoRI buffer (10x) (Promega) | 3 µl |
| BSA (10x) | 3 µl |
| EcoRI (20 U/gl) (Promega) | 1 µl |
| HindIII (10 U/µl) (Promega) | 1 µl |
| H$_2$O | to 30 µl |

Reactions are allowed to proceed at 37° C. for 2 hours, before enzymes are heat inactivated by incubating the reactions at 65° C. for 20 minutes. Reactions are then electrophoresed in a 2% TAE/agarose gel and the bands relating to the nucleic acid fragments isolated using a QIAquick gel extraction kit (QIAGEN).

Nucleic acid concentration is then determined by spectrophotometry measuring UV absorption at 260 nm.

The biodiverse nucleic acid fragments are then ligated into the pGEMEX-1 vector in the following reaction:

| pGEMEX-1 (1 µg) BGF-PCR Fragments (1 µg) | |
|---|---|
| Ligation Buffer (10x) (NEB) | 20 µl |
| T4 polynucleotide kinase (5 U/µl) | 10 µl |
| H$_2$O | to 200 µl |

Ligation reactions are allowed to proceed overnight at 16° C. The ligase is then heat inactivated by incubating the samples at 65° C. for 30 minutes. Following completion of the ligation reaction sample volumes are increased to 500 µl with TE buffer and added to an Amicon spin column. These columns are then centrifuged for 15 minutes at 3,800 rpm in a microcentrifuge. Columns are inverted and 30 µl of TE buffer is added before the columns are centrifuged for 2 minutes at 3,800 rpm, with this fraction collected for later use.

The pGEMEX-1 vector containing the biodiverse nucleic acid fragment is then transformed into *E. coli* TOP10 cells.

Individual colonies of bacteria are then individually picked and plated onto a master plate of LB-agar+ampicillin (50 µg/ml). 100 colonies from each plate are grown in a flask containing 10 ml LB broth until confluent. Approximately 5 drops of the broth is then added to a 9 cm plate containing NG agar (as described in Sulston and Hodgkin (In: The Nematode *Caenorhibditis elegans*, Cold Spring Harbour Laboratories, New York, 1988)), and gently spread to cover approximately two thirds of the surface area of the agar. These plates are then incubated at 37° C. overnight or until a bacterial lawn is observed. These plates are then useful for the growth of *C. elegans*, which feed on the bacterial cells and take up any expressed peptides into their cells. *C. elegans* provides a model system for testing an effect of a peptide expressed by an isolated clone of the expression library in vivo, eg., in target validation.

The model system described in Dent et al, *Proc. Natl. Acad. Sci USA* 97, 2674-267, 1999, showed that *C. elegans* is able to develop resistance to the anti-parasitic antibiotic ivomectin, through mutation of the genes avr-14, avr-15 and glc-1. Such a peptide proves invaluable for the screening of anti-parasitic peptides that act through a pathway that is not affected by these genes.

Approximately 400-500 L4 stage or adult stage *C. elegans* worms that are resistant to ivomectin are seeded onto the plates containing 2 µg/ml Ivomectin (which is not toxic to the mutant strain) and the bacteria expressing an expression library of the present invention. Plates are incubated at 25° C. and scored for live worms every 4-6 hours. A worm is considered dead when it no longer responds to touch.

Plates are scored to determine those that contain a significant portion of dead *C. elegans*, excluding those that have stuck to the side wall. Those plates that have the majority of worms dead are further analyzed.

In further analyzing the peptides that kill the ivomectin resistant worms, single bacterial colonies are used to generate the feeder layer for the worms. An individual colony is picked and grown in a flask containing 10 ml LB broth at 37° C. shaking at 225 rpm, until confluent. Approximately 5 drops of the broth is then added to a 9 cm plate containing NG agar (with 2 µg/ml ivomectin) and gently spread to cover approximately two thirds of the surface area of the agar. Plates are again incubated at 37° C. overnight or until a bacterial lawn is observed.

Again resistant *C. elegans* are seeded onto the plates which are incubated at 25° C. and scored for live worms every 4-6 hours. Bacteria are isolated from those plates containing a significant proportion of dead worms, and cultured for 16 hours in 10 ml LB broth (+50 µg/ml ampicillin). The expression plasmids are then isolated using a QIAprep spin miniprep kit (QIAGEN) using the method described by the manufacturer. Isolated plasmids are then further analyzed to determine the nucleotide sequence that encodes the peptide that is toxic to ivomectin resistant *C. elegans*.

EXAMPLE 10

Development and Screening of a Biodiverse Nucleic Acid Fragment Library from *Takifigu rubripes*

Nucleic acid fragments are generated from genomic DNA from the Japanese puffer fish *T. rubripes* using a restriction enzyme digestion with the enzymes AluI and HaeIII, in the following reaction:

| Genomic DNA (20 µg) | |
| --- | --- |
| Restriction enzyme buffer (10x) | 5 µl |
| AluI(XXU/µg) | 4 µl |
| HaeIII(XXU/µg) | 4 µl |
| H₂O | to 50 µl |

The DNA fragments are then separated by electrophoresis using a 2% agarose/TAE gel. Fragments in the 90-120 bp range are isolated using the QIAquick Gel Extraction Kit (QIAGEN) following manufacturer's instructions.

The concentration of DNA is determined using spectrophotometry at 260 nm.

The adaptor pairs SEQ ID Nos: 42 and 43; SEQ ID Nos: 44 and 45; SEQ ID NOs: 46 and 47; SEQ ID NOs: 48 and 49 are then annealed to one another. This process is completed in H₂O with each of the oligonucleotides at a concentration of 50 µM. Pairs of adaptors are incubated at 94° C. for 10 minutes and then allowed to cool to room temperature slowly.

The annealed adaptors are then ligated to the isolated nucleic acid fragments in separate ligation reactions.

Ligations are carried out in the following reactions:

| Pooled PCR product (average fragment length of 100 bp) | 2 pmol |
| --- | --- |
| Annealed adaptor | 150 pmol |
| Ligation buffer (10x) (Promega) | 1 µl |
| T4 DNA ligase (3 U/µl) (Promega) | 1 µl |
| H₂O | to 10 µl |

Samples are then incubated at 4° C. overnight before being heat-inactivated through incubation at 65° C. for 20 minutes.

Samples are phosphorylated using T4 polynucleotide kinase (Promega) in the following reaction:

| Ligation buffer (10x) (Promega) | 1 µl |
| --- | --- |
| rATP (10 mM) | 2 µl |
| T4 polynucleotide kinase (5 U/µl) | 1 µl |
| H₂O | 20 µl |

Samples are incubated at 37° C. for 30 minutes followed by incubation at 65° C. for 20 minutes to heat inactivate the enzyme.

Nucleic acid fragments from each of the ligation reactions are then combined in equal ratios, ie. equal amounts of nucleic acid, to form one pool. This pool of nucleic acid fragments is then suitable for cloning into the peptide display vector T7Select415-1 (Novagen). However, it is first necessary to digest the T7Select415-1 vector with EcoRI in the following reaction:

| T7Select415-1 vector (1 µg) | |
| --- | --- |
| EcoRI buffer (10x) (Promega) | 3 µl |
| BSA (10x) | 3 µl |
| EcoRI (20 U/µl) (Promega) | 2 µl |
| H₂O | to 30 µl |

Reactions proceed at 37° C. for 2 hours, before enzymes are heat inactivated by incubating the reactions at 65° C. for 20 minutes. Samples are then purified using a QIAquick PCR purification column using manufacturer's instructions. Nucleic acid concentration are then determined by spectrophotometry measuring UV absorption at 260 nm, before diluting the DNA to a final concentration of 0.02 µM.

The nucleic acid fragments are then ligated into the T7Select415-1 vector using the following reaction:

| Ligation buffer (10x) (Novagen) | 0.5 µl |
| --- | --- |
| rATP (10 mM) | 0.5 µl |
| DTT (10 mM) | 0.5 µl |
| T7Select415-1 (0.02 pmol) | 1 µl |
| Nucleic acid fragments | |
| (0; 0.02; and 0.06 pmol in independent reactions) | |
| H₂O | to 5 µl |

Reactions are incubated at 16° C. overnight. Samples are then purified using a QIAquick PCR purification column (QIAGEN), before being diluted in 1 ml of phosphate buffered saline.

The library generated from *T. rubripes* is then screened for mimotopes of epitopes of the D15 protein. The D15 protein is a 80 kDa outer membrane protein of *Haemophilus influenzae*, which are shown to elicit an immune response in rabbits. The antibodies isolated from these rabbits, in turn, are shown to confer resistance to *H. influenzae* to infant rats. Affinity-purified antibodies isolated from rabbits have also been shown to be protective in screens using infant rats (Thomas et al, *Infect Immunol*, 58(6), 1909-1915, 1990).

In an attempt to identify mimotopes of epitopes of the D15 protein, the phage displayed library generated from *T. rubripes*, is screened for those peptides that have a conformation sufficient for binding the affinity purified antibody described in Thomas et al (1990).

The phage display library is added to the affinity purified antibody, which is linked to an antibody coated goat anti-rabbit coupled magnetic beads. These beads are generated by incubating 10 μg of the antibody with 5 mg Dynal beads and incubating at 25° C. for 1 hour, followed by 6 washes with HEG buffer (35 mM HEPES-KOH, pH 7.5/0.1 mM EDTA/100 mM sodium glutamate).

Phage are incubated with these beads at 0° C. for 1 hour, before being washing three times with 5 ml cold HEG buffer/0.1% BSA. Beads are then washed a further three times with HEG buffer using a magnet, such as a tesla magnet (Miltenyi Biotec, Bergish Gladbach, Germany) to immobilise the beads. Bound phage are then eluted with 0.5 ml of 1% SDS. Phage isolated by this method are re-screened, or, alternatively, the nucleic acid fragments encoding the binding peptide are isolated from the phage and analyzed. For example, the amino acid sequences of the peptides are determined.

EXAMPLE 11

Construction of a Biodiverse Nucleic Acid Fragment for Ribosome Display

Nucleic acid is isolated from the following bacterial species:

| | |
|---|---|
| 1 | *Archaeoglobus fulgidis* |
| 2 | *Aquifex aeliticus* |
| 3 | *Aeropyrum pernix* |
| 4 | *Bacillus subtilis* |
| 5 | *Bordetella pertussis* TOX6 |
| 6 | *Borrelia burgdorferi* |
| 7 | *Chlamydia trachomatis* |
| 8 | *Escherichia coli* K12 |
| 9 | *Haemophilus influenzae* (rd) |
| 10 | *Helicobacter pylori* |
| 11 | *Methanobacterium thermoautotrophicum* |
| 12 | *Methanococcus jannaschii* |
| 13 | *Mycoplasma pneumoniae* |
| 14 | *Neisseria meningitidis* |
| 15 | *Pseudomonas aeruginosa* |
| 16 | *Pyrococcus horikoshii* |
| 17 | *S nechosistis* PCC 6803 |
| 18 | *Thermoplasma volcanium* |
| 19 | *Thermotoga maritima* |

Nucleic acid fragments are generated from each of these genomes using 4 consecutive rounds of PCR using tagged random oligonucleotides with the sequence:

(SEQ ID NO: 53)
5'TTTCCCGAATTGTGAGCGGATAACAATAGAAATAATTTTGTTTAACTT

TAAGAAGGAGATATATCCATGGACTACAAAGAN$_9$-3'.

This oligonucleotide introduces a ribosome binding site.

In order to complete this the following reagents are added to the samples:

| | |
|---|---|
| Genomic DNA (100–200 ng) | |
| Oligonucleotide comprising SEQ ID NO: 53 (25 μM) | 4 μl |
| Klenow Buffer | 1 μl |
| dNTP(2 mM) | 3 μl |
| Klenow | 0.5 μl |
| H$_2$O | to 40 μl |

Samples are incubated at 15° C. for 30 minutes, then at room temperature for 2 hours, before being heated to 37° C. for 15 minutes.

Samples are boiled for 5 minutes to again denature the nucleic acid in said sample, before being snap cooled to allow renaturation of said nucleic acid. Another 0.5 μl of the Klenow fragment of *E. coli* DNA polymerase I is added to each reaction, and the samples incubated at 15° C. for 30 minutes, then at room temperature for 2 hours, before being heated to 37° C. for 15 minutes.

The PCR products generated are then used as a template for PCR reactions using the following oligonucleotide:

(SEQ ID NO: 54)
5'GGGGCCAAGCAGTAATAATACGAGTCACTATAGGGAGACCACAAC

GGTTTCCCGAATTGTG-3'.

This oligonucleotide comprises a T7 promoter and a region that is homologous a region of to SEQ ID NO: 53).

Each DNA template is amplified by "one armed" PCR, with the oligonucleotide SEQ ID NO: 54 in separate reactions (ie. 19 reactions). Each PCR reaction contains the following:

| | |
|---|---|
| Template DNA | 1 μl |
| Taq buffer (10x) (Promega) | 5 μl |
| MgCl$_2$ (25 mM) | 4 μl |
| dNTP (2 mM) | 5 μl |
| Oligonucleotide comprising SEQ ID NO: 54 (10 pmol/μl) | 10 μl |
| Taq DNA polymerase (Promega 5 U/μl) | 0.4 μl |
| H$_2$O | to 50 μl |

Reactions are then cycled in a Perkin Elmer thermocycler PE 9700 or PE 2400 using the following program:

5 min 94° C.+30×[30 sec 94° C., 30 sec. 55° C., 1 min 72° C.]+5 min 72° C.

The resulting PCR products are electrophoresed using a 2% agarose/TAE gel, and the nucleic acid fragments between 50 bp to 250 bp extracted using a QIAquick gel extraction kit (QIAGEN) using manufacturer's instructions. Nucleic acid concentration is determined by spectrophotometry measuring UV absorption at 260 nm.

Pools of PCR products derived from each of the 19 bacterial species are produced. To do so, DNA from each organism is added in an equimolar amount when compared to the amount of nucleic acid added to the pool from the organism with the smallest genome.

Nucleic acid fragments are then blunt ended using Munga Bean Nuclease (NEB) in the following reaction:

| Nucleic acid fragments (2 µg) | |
|---|---|
| Mung bean nuclease buffer (10x) | 3 µl |
| Mung bean nuclease (10 U/µl)(NEB) | 2 µl |
| H₂O | to 30 µl |

The reaction proceeds at 30° C. for 1 hour. The sample is then purified using a QIAquick PCR purification column (QIAGEN) as per manufacturer's instructions.

Oligonucleotides encoding a blunt-end adaptor are generated comprising the following sequences:

5'-TTTAAGCAGCTCGATAGCAGCAGC-3'; (SEQ ID NO: 55)
and

5'-GTGCTGCTATCGAGCTGCTTAAA-3'. (SEQ ID NO: 56)

The adaptors are annealed to one another. This process is completed in H₂O with each of the oligonucleotides at a concentration of 50 µM. Pairs of adaptors are incubated at 94° C. for 10 minutes and then allowed to cool to room temperature slowly. Annealed adaptors are ligated to the nucleic acid fragments in the following reactions:

| | |
|---|---|
| Pooled PCR product (average length of 150 bp) | 2 pmol |
| Annealed adaptor | 150 pmol |
| Ligation buffer (10x) (Promega) | 1 µl |
| T4 DNA ligase (3 U/µl) (Promega) | 1 µl |
| H₂O | to 10 µl |

Samples are then incubated at 4° C. overnight before being heat inactivated through incubation at 65° C. for 20 minutes. The ligation reaction is then purified using a QIAquick PCR purification kit (QIAGEN)

The modified nucleic acid fragments are then amplified in a PCR reaction with oligonucleotides of the sequence SEQ ID NO: 54 and the following sequence: 5' AGACCCGTT-TAGAGGCCCCAAGGGGTTATGGAAT-TCACCTTTAAGCAGCT C-3' (SEQ ID NO: 57). The oligonucleotide of SEQ ID NO: 57 introduces a modified lipoprotein terminator with the stop codon removed.

The PCR reactions are completed in the following reaction:

| | |
|---|---|
| Template DNA | 1 µl |
| pfu buffer (10x) (Promega) | 5 µl |
| MgCl₂ (25 mM) | 4 µl |
| dNTP (2 mM) | 5 µl |
| oligonucleotide SEQ ID NO: 54 (10 pmol/µl) | 10 µl |
| oligonucleotide SEQ ID NO: 57 (10 pmol/µl) | 10 µl |
| pfu DNA polymerase (Promega 5 U/µl) | 0.4 µl |
| H₂O | to 50 µl |

The PCR reactions are completed with the following cycling conditions:

5 min 94° C.+30×[30 sec 94° C., 30 sec. 55° C., 1 min 72° C.]+5 min 72° C.

PCR products are then purified using a QIAquick PCR purification column (QIAGEN).

In a separate reaction the amino acids 211-299 of gene III of filamentous phage M13 are amplified using the following oligonucleotides:

(SEQ ID NO: 58)
5'-CGTGAAAAAATTATTATTCGCAATTC-3'

(SEQ ID NO: 59)
5'-TTAAGACTCCTTATTACGCAGTATGTTAGC-3'

The oligonucleotide SEQ ID NO: 58 is phosphorylated using T4 polynucleotide kinase (Promega), to allow for later directional cloning of the PCR product. The phosphorylation proceeds in the following reaction:

| Oligonucleotide (SEQ ID NO: 58) | |
|---|---|
| Ligation buffer (10x) (Promega) | 1 µl |
| rATP (10 mM) | 2 µl |
| T4 polynucleotide kinase (5 U/µl) | 1 µl |
| H₂O | 20 µl |

Samples are incubated at 37° C. for 30 minutes followed by incubation at 65° C. for 20 minutes to heat inactivate the T4 polynucleotide kinase.

The oligonucleotides are then used in the following PCR reaction:

| | |
|---|---|
| Template DNA | 1 µl |
| pfu buffer (10x) (Promega) | 5 µl |
| MgCl₂ (25 mM) | 4 µl |
| dNTP (2 mM) | 5 µl |
| oligonucleotide SEQ ID NO: 58 (10 pmol/µl) | 10 µl |
| oligonucleotide SEQ ID NO: 59 (10 pmol/µl) | 10 µl |
| pfu DNA polymerase (Promega 5 U/µl) | 0.4 µl |
| H₂O | to 50 µl |

Reactions are then cycled in a Perkin Elmer thermocycler PE 9700 or PE 2400 using the following program:

5 min 94° C.+30×[30 sec 94° C., 30 sec. 59° C., 1 min 72° C.]+5 min 72° C.

Reactions are electrophoresed in a 2% TAE/agarose gel and the 1276 bp fragment isolated using a QIAquick gel purification kit (QIAGEN).

The modified nucleic acid fragments and the spacer sequence isolated from M13 phage are then ligated in the following reaction:

| Modified nucleic acid fragment (2 µg) Spacer (2 µg) | |
|---|---|
| Ligation buffer (10x) (Promega) | 2 µl |
| T4 DNA ligase (3 U/µl) (Promega) | 1 µl |
| H₂O | to 20 µl |

Samples are then incubated at 4° C. overnight before being heat inactivated through incubation at 65° C. for 20 minutes. The ligation reaction is then purified using a QIAquick PCR purification kit (Qiagen)

The resulting gene constructs are transcribed and translated in vitro using the Promega *E. coli* S 30 Extract system for linear templates as per manufacturer's instructions, which are a modification of the protocol of Leslie et al, *J. Biol. Chem.* 266, 2632-1991.

The translation reaction is stopped by adding magnesium acetate [Mg(OAc)$_2$] to a final concentration of 50 mM, chloroamphenicol to a final concentration of 50 μM and cooling the samples on ice. The samples are then diluted 8 fold with ice-cold wash buffer (50 mM Tris-HOAc, pH 7.5/150 mM NaCl/50 mM Mg(Oac)$_2$/0.1% Tween 20) and centrifuged for 5 minutes at 4° C. at 100,000 g to remove any insoluble components.

The in vitro displayed library is then screened to isolate peptides that bind to α-FLAG monoclonal antibody. The monoclonal antibody is first adsorbed to a microtiter plate. Each well of a microtiter plate is rinsed twice with distilled water. The α-FLAG monoclonal antibody (α-FLAG M2, Sigma Aldrich) is diluted in TBS buffer to 20 μg/ml and 100 μl added per well. The antibody is allowed to adsorb at 4° C. overnight. The microtiter plate is then rinsed three times with TBS buffer and filled with 5% skim milk in distilled water. For blocking the skim milk solution is allowed to bind with gentle rocking for 1 hour at room temperature. The dish is then rinsed five times with double distilled water (ddH$_2$O) and filled with ddH$_2$O until use.

Prior to use, each well of the microtiter plate is washed with ice-cold wash buffer, and the supernatant from the centrifuged translation mixture applied (200 μl per well). The plate is then gently rocked for 1 hour at room temperature. Each well of the microtiter plate is then washed with ice-cold wash buffer five times, and the bound ribosome displayed peptides eluted using ice cold elution buffer (50 mM Tris-HOAc, pH 7.5/150 mM NaCl/10 mM EDTA/50 μg/ml *E. coli* tRNA). Elution buffer (100 μl) is added per well, and the plates gently rocked for 10 minutes at 4° C. The released mRNA is recovered using the RNeasy kit (QIAGEN) using manufacturer's instructions.

Recovered mRNAs are then reverse transcribed using Superscript reverse transcriptase (Invitrogen) according to manufacturer's instructions. The positive nucleic acid fragments are then amplified using PCR with the oligonucleotides (very first ones without random bases). PCR products are electrophoresed in a 2% TAE/agarose gel and the PCR products recovered using QIAquick gel extraction kit. Recovered nucleic acids are then sequenced using a Big Dye Terminator system (Perkin Elmer).

EXAMPLE 12

Compatibility of *S. aureus* and *E. coli* Infected with T7 Growing on Solid Media in Close Proximity Initial tests are carried out to establish whether the growth of an *E. coli* lawn containing T7 bacteriophage plaques is generally inhibitory to the growth of a lawn of *S. aureus* on top of a semipermeable membrane laid down on top of the phage overlay. The results of this assay suggested that both the *E. coli* /T7 culture, and the *S. aureus* culture are able to grow without any apparent interference. Accordingly, this assay format is utilised in determining those peptides that demonstrate antibacterial properties.

We claim:

1. A method of constructing an expression library for expressing a peptide having a conformation sufficient for binding to a target protein or nucleic acid, said method comprising:

(a) producing nucleic acid fragments from nucleic acids derived from two or more microorganisms or eukaryotes containing compact genomes, each of said microorganisms or eukaryotes having a substantially sequenced genome; and (b) selecting nucleic acid fragments of sufficient length to encode a peptide comprising a protein domain having an average length of at least 12 to 15 amino acids; and (c) inserting the nucleic acid fragments at (b) into a suitable expression construct in an amount proportional to the size of the genome from which the fragments were derived thereby producing recombinant constructs, wherein each fragment is in operable connection with a promoter sequence that is capable of conferring expression of that fragment.

2. The method of claim 1 further comprising selecting nucleic acid fragments from the fragments at (a) that have substantially different nucleotide sequences thereby enhancing nucleotide sequence diversity among the selected fragments compared to the diversity of sequences in the genome.

3. The method of claim 1, further comprising introducing the recombinant construct into a host cell.

4. The method according to claim 1 wherein producing nucleic acid fragments comprising amplifying nucleic acid from two or more microorganisms or eukaryotes comprising compact genomes.

5. The method according to claim 1 wherein producing nucleic acid fragments comprises amplifying genomic DNA from two or more microorganisms or eukaryotes comprising compact genomes.

6. The method according to claim 1 wherein step 1(c) comprises inserting the nucleic acid fragments at (b) into a suitable expression construct in equimolar amounts thereby producing recombinant constructs, wherein each fragments is in operable connection with a promoter sequence that is capable of conferring expression on that fragment.

7. The method according to claim 1 wherein the two or more microorganisms or compact eukaryotes are selected from the group consisting of *Aeropyrum pernix, Anopheles gambiae, Arabidopsis thaliana, Aquifex aeolicus, Archaeoglobus fulgidis, Bacillus subtilis, Bordetella pertussis, Borrelia burgdorferi, Caenorhabditis elegans, Chlamydia trachomatis, Danio rerio, Drosophila melanogaster, Escherichia coli, Haemophilus influenzae, Helicobacter pylori, Methemobacterium thermoautotrophicum, Methanococcus jannaschii, Mycoplasma pneumoniae, Neisseria meningitidis, Pseudomonas aeruginosa, Pyococcus horikoshii, Saccharomyces cerevesiae, Schizosaccharomyces pombe, Synechocystis* PCC 6803, *Takifugu rubripes, Thermoplasma volcanium,* and *Thermotoga maritima.*

8. The method according to claim 1 wherein the two or more microorganisms are selected from the group consisting of *Archaeoglobus fulgidis, Aquifex aeolicus, Aeropyrum pernix, Bacillus subtilis, Bordetella pertussis* TOX6, *Borrelia burgdorferi, Chlamydia trachomatis, Escherichia coli* K12, *Haemophilus influenzae* (rd), *Helicobacter pylori, Methanobacterium thermoautotrophicum, Methanococcus jannaschii, Mycoplasma pneumoniae, Neisseria meningitidis, Pseudomonas aeruginosa, Pyrococcus horikoshii, Synechocystis* PCC 6803, *Theroplasma volcanium* and *Thermotoga maritima.*

9. The method according to claim 1 wherein the promoter sequence is operable in a yeast cell.

10. The method according to claim 1 wherein the promoter sequence is operable in a bacterial cell.

11. The method according to claim 1 wherein the expression construct is a yeast expression vector.

12. The method according to claim 1 wherein the expression construct is a phage display vector.

13. The method according to claim 3 wherein the host cell is a yeast cell.

14. The method according to claim 3 wherein the host cell is a bacterial cell.

* * * * *

SEQUENCE LISTING

<160> NUMBER OF SEQ ID NOS: 81

<210> SEQ ID NO 1
<211> LENGTH: 6
<212> TYPE: DNA
<213> ORGANISM: Artificial Sequence
<220> FEATURE:
<221> NAME/KEY: misc_feature
<222> LOCATION: 2, 3
<223> OTHER INFORMATION: n = A,T,C or G
<220> FEATURE:
<223> OTHER INFORMATION: synthetic Kozak consensus sequence

<400> SEQUENCE: 1 rnnatg                                                                 6

<210> SEQ ID NO 2
<211> LENGTH: 8
<212> TYPE: DNA
<213> ORGANISM: Artificial Sequence
<220> FEATURE:
<223> OTHER INFORMATION: synthetic Kozak consensus sequence

<400> SEQUENCE: 2 ccrccatg                                                               8

<210> SEQ ID NO 3
<211> LENGTH: 11
<212> TYPE: DNA
<213> ORGANISM: Artificial Sequence
<220> FEATURE:
<223> OTHER INFORMATION: synthetic Kozak consensus sequence

<400> SEQUENCE: 3
gccagccatg g                                                          11

```
<210> SEQ ID NO 4
<211> LENGTH: 8
<212> TYPE: DNA
<213> ORGANISM: Artificial Sequence
<220> FEATURE:
<223> OTHER INFORMATION: synthetic Kozak consensus sequence

<400> SEQUENCE: 4 ctaccatg                                                                 8

<210> SEQ ID NO 5
<211> LENGTH: 10
<212> TYPE: DNA
<213> ORGANISM: Artificial Sequence
<220> FEATURE:
<223> OTHER INFORMATION: synthetic Shine Dalgarno sequence

<400> SEQUENCE: 5
gaagaagata                                                              10

<210> SEQ ID NO 6
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 6 aaaaaac                                                                  7

<210> SEQ ID NO 7
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 7 aaattta                                                                  7

<210> SEQ ID NO 8
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 8 aaatttt                                                                  7

<210> SEQ ID NO 9
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 9 gggaaac                                                                  7

<210> SEQ ID NO 10
<211> LENGTH: 7
<212> TYPE: DNA
<213> ORGANISM: Artificial Sequence
<220> FEATURE:
```

<223> OTHER INFORMATION: synthetic translational slippage sequence

<400> SEQUENCE: 10 gggcccc                                                                 7

<210> SEQ ID NO 11
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 11 gggttta                                                                 7

<210> SEQ ID NO 12
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 12 gggtttt                                                                 7

<210> SEQ ID NO 13
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 13 tttaaac                                                                 7

<210> SEQ ID NO 14
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 14 tttaaat                                                                 7

<210> SEQ ID NO 15
<211> LENGTH: 6
<212> TYPE: DNA
<213> ORGANISM: Artificial Sequence
<220> FEATURE:
<223> OTHER INFORMATION: synthetic translational slippage sequence

<400> SEQUENCE: 15 tttta                                                                   6

<210> SEQ ID NO 16
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 16 ggattta                                                                 7

```
<210> SEQ ID NO 17
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 17 cttaggc                                                             7

<210> SEQ ID NO 18
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 18 gcgagtt                                                             7

<210> SEQ ID NO 19
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 19 tcctgat                                                             7

<210> SEQ ID NO 20
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 20 aaaaaag                                                             7

<210> SEQ ID NO 21
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 21 aaaaaaa                                                             7

<210> SEQ ID NO 22
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 22 aaaaaac                                                             7

<210> SEQ ID NO 23
<211> LENGTH: 7
<212> TYPE: DNA
<213> ORGANISM: Artificial Sequence
<220> FEATURE:
<223> OTHER INFORMATION: synthetic translational slippage sequence
```

```
<400> SEQUENCE: 23 gggaaag                                                              7

<210> SEQ ID NO 24
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 24 aaaaggg                                                              7

<210> SEQ ID NO 25
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 25 gggaaaa                                                              7

<210> SEQ ID NO 26
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 26 tttaaag                                                              7

<210> SEQ ID NO 27
<211> LENGTH: 7
<212> TYPE: DNA
<213> ORGANISM: Artificial Sequence
<220> FEATURE:
<223> OTHER INFORMATION: synthetic translational slippage sequence

<400> SEQUENCE: 27 aaagggg                                                              7

<210> SEQ ID NO 28
<211> LENGTH: 3
<212> TYPE: DNA
<213> ORGANISM: Artificial Sequence
<220> FEATURE:
<223> OTHER INFORMATION: synthetic translational slippage sequence

<400> SEQUENCE: 28 ctt                                                                  3

<210> SEQ ID NO 29
<211> LENGTH: 17
<212> TYPE: PRT
<213> ORGANISM: Drosophila

<400> SEQUENCE: 29

Cys Arg Gln Ile Lys Ile Trp Phe Gln Asn Arg Arg Met Lys Trp Lys
1               5                   10                  15

Lys

<210> SEQ ID NO 30
```

<210> SEQ ID NO 30
<211> LENGTH: 21
<212> TYPE: PRT
<213> ORGANISM: Artificial Sequence
<220> FEATURE:
<223> OTHER INFORMATION: synthetic Pep1 peptide

<400> SEQUENCE: 30

Lys Glu Thr Trp Trp Glu Thr Trp Trp Thr Glu Trp Ser Gln Lys Lys
1               5                   10                  15

Lys Lys Arg Lys Val
            20

<210> SEQ ID NO 31
<211> LENGTH: 5
<212> TYPE: DNA
<213> ORGANISM: Artificial Sequence
<220> FEATURE:
<223> OTHER INFORMATION: synthetic initiator sequence recognized by P2A
      protein

<400> SEQUENCE: 31 tcgga                                                                   5

<210> SEQ ID NO 32
<211> LENGTH: 5
<212> TYPE: PRT
<213> ORGANISM: Artificial Sequence
<220> FEATURE:
<223> OTHER INFORMATION: synthetic membrane anchor sequence

<400> SEQUENCE: 32

Pro Asp Gly Phe Arg
1               5

<210> SEQ ID NO 33
<211> LENGTH: 46
<212> TYPE: DNA
<213> ORGANISM: Artificial Sequence
<220> FEATURE:
<221> NAME/KEY: misc_feature
<222> LOCATION: 41, 42, 43, 44, 45, 46
<223> OTHER INFORMATION: n = A,T,C or G
<220> FEATURE:
<223> OTHER INFORMATION: synthetic oligonucleotide primer

<400> SEQUENCE: 33
gactacaagg acgacgacga caaggcttat caatcaatca nnnnnn                     46

<210> SEQ ID NO 34
<211> LENGTH: 49
<212> TYPE: DNA
<213> ORGANISM: Artificial Sequence
<220> FEATURE:
<221> NAME/KEY: misc_feature
<222> LOCATION: 41, 42, 43, 44, 45, 46, 47, 48, 49
<223> OTHER INFORMATION: n = A,T,C or G
<220> FEATURE:
<223> OTHER INFORMATION: synthetic oligonucleotide primer

<400> SEQUENCE: 34
gactacaagg acgacgacga caaggcttat caatcaatca nnnnnnnnn                  49

<210> SEQ ID NO 35
<211> LENGTH: 40
<212> TYPE: DNA
<213> ORGANISM: Artificial Sequence
<220> FEATURE:
<223> OTHER INFORMATION: synthetic oligonucleotide primer

<400> SEQUENCE: 35
gagagaattc aggtcagact acaaggacga cgacgacaag                    40

<210> SEQ ID NO 36
<211> LENGTH: 5562
<212> TYPE: DNA
<213> ORGANISM: Artificial Sequence
<220> FEATURE:
<223> OTHER INFORMATION: synthetic pDEATH-TRYP vector

<400> SEQUENCE: 36

| | |
|---|---:|
| ctagcgattt tggtcatgag atcagatcaa cttcttttct ttttttttct tttctctctc | 60 |
| ccccgttgtt gtctcaccat atccgcaatg acaaaaaaat gatggaagac actaaaggaa | 120 |
| aaaattaacg acaaagacag caccaacaga tgtcgttgtt ccagagctga tgagggtat | 180 |
| ctcgaagcac acgaaacttt ttccttcctt cattcacgca cactactctc taatgagcaa | 240 |
| cggtatacgg ccttccttcc agttacttga atttgaaata aaaaaaagtt tgctgtcttg | 300 |
| ctatcaagta taaatagacc tgcaattatt aatcttttgt ttcctcgtca ttgttctcgt | 360 |
| tccctttctt ccttgtttct ttttctgcac aatatttcaa gctataccaa gcatacaatc | 420 |
| aactccaagc ttccccggat cggactacta gcagctgtaa tacgactcac tatagggaat | 480 |
| attaagctca ccatgggtaa gcctatccct aaccctctcc tcggtctcga ttctacacaa | 540 |
| gctatgggtg ctcctccaaa aaagaagaga aaggtagctg aattcgagct cagatctcag | 600 |
| ctgggcccgg taccaattga tgcatcgata ccggtactag tcggaccgca tatgcccggg | 660 |
| cgtaccgcgg ccgctcgagg catgcatcta gagggccgca tcatgtaatt agttatgtca | 720 |
| cgcttacatt cacgccctcc ccccacatcc gctctaaccg aaaaggaagg agttagacaa | 780 |
| cctgaagtct aggtccctat ttatttttt atagttatgt tagtattaag aacgttattt | 840 |
| atatttcaaa tttttctttt ttttctgtac agacgcgtgt acgcatgtaa cattatactg | 900 |
| aaaaccttgc ttgagaaggt tttgggacgc tcgaaggctt taatttgcgg ccctgcatta | 960 |
| atgaatcggc caacgcgcgg ggagaggcgg tttgcgtatt gggcgctctt ccgcttcctc | 1020 |
| gctcactgac tcgctgcgct cggtcgttcg gctgcggcga gcggtatcag ctcactcaaa | 1080 |
| ggcggtaata cggttatcca cagaatcagg ggataacgca ggaaagaaca tgtgagcaaa | 1140 |
| aggccagcaa aagcccagga accgtaaaaa ggccgcgttg ctggcgtttt tccataggct | 1200 |
| ccgcccccct gacgagcatc acaaaaatcg acgctcaagt cagaggtggc gaaacccgac | 1260 |
| aggactataa agataccagg cgtttccccc tggaagctcc ctcgtgcgct ctcctgttcc | 1320 |
| gaccctgccg cttaccggat acctgtccgc ctttctccct tcgggaagcg tggcgctttc | 1380 |
| tcatagctca cgctgtaggt atctcagttc ggtgtaggtc gttcgctcca agctgggctg | 1440 |
| tgtgcacgaa ccccccgttc agcccgaccg ctgcgcctta tccggtaact atcgtcttga | 1500 |
| gtccaacccg gtaagacacg acttatcgcc actggcagca gccactggta acaggattag | 1560 |
| cagagcgagg tatgtaggcg gtgctacaga gttcttgaag tggtggccta actacggcta | 1620 |
| cactagaagg acagtatttg gtatctgcgc tctgctgaag ccagttacct tcggaaaaag | 1680 |
| agttggtagc tcttgatccg gcaaacaaac caccgctggt agcggtggtt ttttgtttg | 1740 |
| caagcagcag attacgcgca gaaaaaaagg atctcaagaa gatcctttga tcttttctac | 1800 |
| ggggtctgac gctcagtgga acgaaaactc acgttaaggg attttggtca tgagattatc | 1860 |
| aaaaaggatc ttcacctaga tccttttaaa ttaaaaatga agttttaaat caatctaaag | 1920 |

```
tatatatgag taaacttggt ctgacagtta ccaatgctta atcagtgagg cacctatctc      1980
agcgatctgt ctatttcgtt catccatagt tgcctgactc cccgtcgtgt agataactac      2040
gatacgggag cgcttaccat ctggccccag tgctgcaatg ataccgcgag acccacgctc      2100
accggctcca gatttatcag caataaacca gccagccgga agggccgagc gcagaagtgg      2160
tcctgcaact ttatccgcct ccatccagtc tattaattgt tgccgggaag ctagagtaag      2220
tagttcgcca gttaatagtt tgcgcaacgt tgttgccatt gctacaggca tcgtggtgtc      2280
acgctcgtcg tttggtatgg cttcattcag ctccggttcc caacgatcaa ggcgagttac      2340
atgatccccc atgttgtgca aaaaagcggt tagctccttc ggtcctccga tcgttgtcag      2400
aagtaagttg gccgcagtgt tatcactcat ggttatggca gcactgcata attctcttac      2460
tgtcatgcca tccgtaagat gcttttctgt gactggtgag tactcaacca gtcattctg       2520 agaatagtgt atgcggcgac cgagttgctc ttgcccggcg tcaacacggg ataataccgc      2580
gccacatagc agaactttaa aagtgctcat cattggaaaa cgttcttcgg ggcgaaaact      2640
ctcaaggatc ttaccgctgt tgagatccag ttcgatgtaa cccactcgtg cacccaactg      2700
atcttcagca tcttttactt tcaccagcgt ttctgggtga gcaaaaacag gaaggcaaaa      2760
tgccgcaaaa aagggaataa gggcgacacg gaaatgttga atactcatac tcttcctttt      2820
tcaatattat tgaagcattt atcagggtta ttgtctcatg agcggataca tatttgaatg      2880
tatttagaaa aataaacaaa tagggggttcc gcgcacattt ccccgaaaag tgccacctga      2940
cgtctaagaa accattatta tcatgacatt aacctataaa aataggcgta tcacgaggcc      3000
ctttcgtctt caagaaattc ggtcgaaaaa agaaaaggag agggccaaga gggagggcat      3060
tggtgactat tgagcacgtg agtatacgtg attaagcaca caaaggcagc ttggagtatg      3120
tctgttatta atttcacagg tagttctggt ccattggtga agtttgcgg cttgcagagc      3180 acagaggccg cagaatgtgc tctagattcc gatgctgact tgctgggtat tatatgtgtg      3240
cccaatagaa agagaacaat tgacccggtt attgcaagga aaatttcaag tcttgtaaaa      3300
gcatataaaa atagttcagg cactccgaaa tacttggttg gcgtgtttcg taatcaacct      3360
aaggaggatg ttttggctct ggtcaatgat tacggcattg atatcgtcca actgcacgga      3420
gatgagtcgt ggcaagaata ccaagagttc ctcggtttgc cagttattaa agactcgta      3480 tttccaaaag actgcaacat actactcagt gcagcttcac agaaacctca ttcgtttatt      3540
cccttgtttg attcagaagc aggtgggaca ggtgaacttt tggattggaa ctcgatttct      3600
gactgggttg aaggcaaga gagccccgag agcttacatt ttatgttagc tggtggactg       3660
acgccagaaa atgttggtga tgcgcttaga ttaaatggcg ttattggtgt tgatgtaagc      3720
ggaggtgtgg agacaaatgg tgtaaaagac tctaacaaaa tagcaaattt cgtcaaaaat      3780
gctaagaaat aggttattac tgagtagtat ttatttaagt attgtttgtg cacttgcctg      3840
cagcttctca atgatattcg aatacgcttt gaggagatac agcctaatat ccgacaaact      3900
gttttacaga tttacgatcg tacttgttac ccatcattga attttgaaca tccgaacctg      3960
ggagttttcc ctgaaacaga tagtatattt gaacctgtat aataatatat agtctagcgc      4020
tttacggaag acaatgtatg tatttcggtt cctggagaaa ctattgcatc tattgcatag      4080
gtaatcttgc acgtcgcatc cccggttcat tttctgcgtt tccatcttgc acttcaatag      4140
catatctttg ttaacgaagc atctgtgctt cattttgtag aacaaaaatg caacgcgaga      4200
gcgctaattt tcaaacaaa gaatctgagc tgcatttta cagaacagaa atgcaacgcg      4260
aaagcgctat tttaccaacg aagaatctgt gcttcatttt tgtaaaacaa aaatgcaacg      4320
```

```
cgagagcgct aatttttcaa acaaagaatc tgagctgcat ttttacagaa cagaaatgca    4380
acgcgagagc gctattttac caacaaagaa tctatacttc ttttttgttc tacaaaaatg    4440
catcccgaga gcgctatttt tctaacaaag catcttagat tacttttttt ctcctttgtg    4500
cgctctataa tgcagtctct tgataacttt ttgcactgta ggtccgttaa ggttagaaga    4560
aggctacttt ggtgtctatt ttctcttcca taaaaaagc ctgactccac ttcccgcgtt     4620
tactgattac tagcgaagct gcgggtgcat ttttcaaga taaaggcatc cccgattata    4680
ttctataccg atgtggattg cgcatacttt gtgaacagaa agtgatagcg ttgatgattc    4740
ttcattggtc agaaaattat gaacggtttc ttctattttg tctctatata ctacgtatag    4800
gaaatgttta cattttcgta ttgttttcga ttcactctat gaatagttct tactacaatt    4860
tttttgtcta aagagtaata ctagagataa acataaaaaa tgtagaggtc gagtttagat    4920
gcaagttcaa ggagcgaaag gtggatgggt aggttatata gggatatagc acagagatat    4980
atagcaaaga gatactttg agcaatgttt gtggaagcgg tattcgcaat gggaagctcc     5040
accccggttg ataatcagaa aagccccaaa aacaggaaga ttgtataagc aaatatttaa    5100
attgtaaacg ttaatatttt gttaaaattc gcgttaaatt tttgttaaat cagctcattt    5160
tttaacgaat agcccgaaat cggcaaaatc ccttataaat caaaagaata daccgagata    5220
gggttgagtg ttgttccagt ttccaacaag agtccactat taaagaacgt ggactccaac    5280
gtcaaagggc gaaaaaggt ctatcagggc gatggcccac tacgtgaacc atcaccctaa     5340
tcaagttttt tggggtcgag gtgccgtaaa gcagtaaatc ggaagggtaa acggatgccc    5400
ccatttagag cttgacgggg aaagccggcg aacgtggcga aaaggaagg gaagaaagcg     5460 aaaggagcgg gggctagggc ggtgggaagt gtagggtca cgctgggcgt aaccaccaca     5520
cccgccgcgc ttaatggggc gctacagggc gcgtgggat ga                       5562

<210> SEQ ID NO 37
<211> LENGTH: 40
<212> TYPE: DNA
<213> ORGANISM: Artificial Sequence
<220> FEATURE:
<223> OTHER INFORMATION: synthetic oligonucleotide primer

<400> SEQUENCE: 37
agaggaattc aggtcagact acaaggacga cgacgacaag                          40

<210> SEQ ID NO 38
<211> LENGTH: 27
<212> TYPE: DNA
<213> ORGANISM: Artificial Sequence
<220> FEATURE:
<223> OTHER INFORMATION: synthetic oligonucleotide primer

<400> SEQUENCE: 38
cagaagctta aggacgacga cgacaag                                        27

<210> SEQ ID NO 39
<211> LENGTH: 27
<212> TYPE: DNA
<213> ORGANISM: Artificial Sequence
<220> FEATURE:
<223> OTHER INFORMATION: synthetic oligonucleotide primer

<400> SEQUENCE: 39
caggaattca aggacgacga cgacaag                                        27
```

```
<210> SEQ ID NO 40
<211> LENGTH: 28
<212> TYPE: DNA
<213> ORGANISM: Artificial Sequence
<220> FEATURE:
<223> OTHER INFORMATION: synthetic oligonucleotide primer

<400> SEQUENCE: 40
caggaattcc aaggacgacg acgacaag                                28

<210> SEQ ID NO 41
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 41
caggaattca caaggacgac gacgacaag                               29

<210> SEQ ID NO 42
<211> LENGTH: 16
<212> TYPE: DNA
<213> ORGANISM: Artificial Sequence
<220> FEATURE:
<223> OTHER INFORMATION: synthetic adaptor oligonucleotide

<400> SEQUENCE: 42
aattcgaacc ccttcg                                             16

<210> SEQ ID NO 43
<211> LENGTH: 12
<212> TYPE: DNA
<213> ORGANISM: Artificial Sequence
<220> FEATURE:
<223> OTHER INFORMATION: synthetic adaptor oligonucleotide

<400> SEQUENCE: 43
cgaaggggtt cg                                                 12

<210> SEQ ID NO 44
<211> LENGTH: 17
<212> TYPE: DNA
<213> ORGANISM: Artificial Sequence
<220> FEATURE:
<223> OTHER INFORMATION: synthetic adaptor oligonucleotide

<400> SEQUENCE: 44
aattcgaacc ccttcgc                                            17

<210> SEQ ID NO 45
<211> LENGTH: 13
<212> TYPE: DNA
<213> ORGANISM: Artificial Sequence
<220> FEATURE:
<223> OTHER INFORMATION: synthetic adaptor oligonucleotide

<400> SEQUENCE: 45
gcgaaggggt tcg                                                13

<210> SEQ ID NO 46
<211> LENGTH: 18
<212> TYPE: DNA
<213> ORGANISM: Artificial Sequence
<220> FEATURE:
<223> OTHER INFORMATION: synthetic adaptor oligonucleotide
```

```
<400> SEQUENCE: 46
aattcgaacc ccttcgcg                                              18

<210> SEQ ID NO 47
<211> LENGTH: 13
<212> TYPE: DNA
<213> ORGANISM: Artificial Sequence
<220> FEATURE:
<223> OTHER INFORMATION: synthetic adaptor oligonucleotide

<400> SEQUENCE: 47
gcgaaggggt tcg                                                   13

<210> SEQ ID NO 48
<211> LENGTH: 16
<212> TYPE: DNA
<213> ORGANISM: Artificial Sequence
<220> FEATURE:
<223> OTHER INFORMATION: synthetic adaptor oligonucleotide

<400> SEQUENCE: 48
agctcgaagg ggttcg                                                16

<210> SEQ ID NO 49
<211> LENGTH: 12
<212> TYPE: DNA
<213> ORGANISM: Artificial Sequence
<220> FEATURE:
<223> OTHER INFORMATION: synthetic adaptor oligonucleotide

<400> SEQUENCE: 49 cgaaccccctt cg                                                   12

<210> SEQ ID NO 50
<211> LENGTH: 8
<212> TYPE: PRT
<213> ORGANISM: Artificial Sequence
<220> FEATURE:
<223> OTHER INFORMATION: synthetic FLAG epitope

<400> SEQUENCE: 50

Asp Tyr Lys Asp Asp Asp Asp Lys
1               5

<210> SEQ ID NO 51
<211> LENGTH: 31
<212> TYPE: DNA
<213> ORGANISM: Artificial Sequence
<220> FEATURE:
<223> OTHER INFORMATION: synthetic FLAG-encoding oligonucleotide

<400> SEQUENCE: 51
aattccgact acaaggacga cgatgacaag a                               31

<210> SEQ ID NO 52
<211> LENGTH: 31
<212> TYPE: DNA
<213> ORGANISM: Artificial Sequence
<220> FEATURE:
<223> OTHER INFORMATION: synthetic FLAG-encoding oligonucleotide

<400> SEQUENCE: 52
agcttcttgt catcgtcgtc cttgtagtcg g                               31
```

```
<210> SEQ ID NO 53
<211> LENGTH: 89
<212> TYPE: DNA
<213> ORGANISM: Artificial Sequence
<220> FEATURE:
<221> NAME/KEY: misc_feature
<222> LOCATION: 81, 82, 83, 84, 85, 86, 87, 88, 89
<223> OTHER INFORMATION: n = A,T,C or G
<220> FEATURE:
<223> OTHER INFORMATION: synthetic tagged random oligonucleotide

<400> SEQUENCE: 53
tttcccgaat tgtgagcgga taacaataga aataattttg tttaacttta agaaggagat      60
atatccatgg actacaaaga nnnnnnnnn                                       89

<210> SEQ ID NO 54
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 54
ggggccaagc agtaataata cgagtcacta tagggagacc acaacggttt cccgaattgt      60
g                                                                     61

<210> SEQ ID NO 55
<211> LENGTH: 23
<212> TYPE: DNA
<213> ORGANISM: Artificial Sequence
<220> FEATURE:
<223> OTHER INFORMATION: synthetic adaptor oligonucleotide

<400> SEQUENCE: 55
tttaagcagc tcgatagcag cac                                             23

<210> SEQ ID NO 56
<211> LENGTH: 23
<212> TYPE: DNA
<213> ORGANISM: Artificial Sequence
<220> FEATURE:
<223> OTHER INFORMATION: synthetic adaptor oligonucleotide

<400> SEQUENCE: 56
gtgctgctat cgagctgctt aaa                                             23

<210> SEQ ID NO 57
<211> LENGTH: 51
<212> TYPE: DNA
<213> ORGANISM: Artificial Sequence
<220> FEATURE:
<223> OTHER INFORMATION: synthetic lipoprotein terminator
      oligonucleotide

<400> SEQUENCE: 57
agacccgttt agaggcccca agggttatg gaattcacct ttaagcagct c                51

<210> SEQ ID NO 58
<211> LENGTH: 26
<212> TYPE: DNA
<213> ORGANISM: Artificial Sequence
<220> FEATURE:
<223> OTHER INFORMATION: synthetic M13 gene III oligonucleotide

<400> SEQUENCE: 58
cgtgaaaaaa ttattattcg caattc                                          26
```

<210> SEQ ID NO 59
<211> LENGTH: 30
<212> TYPE: DNA
<213> ORGANISM: Artificial Sequence
<220> FEATURE:
<223> OTHER INFORMATION: synthetic M13 gene III oligonucleotide

<400> SEQUENCE: 59
ttaagactcc ttattacgca gtatgttagc                                       30

<210> SEQ ID NO 60
<211> LENGTH: 7551
<212> TYPE: DNA
<213> ORGANISM: Artificial Sequence
<220> FEATURE:
<223> OTHER INFORMATION: synthetic pJFK vector

<400> SEQUENCE: 60
ccccattatc ttagcctaaa aaaccttct ctttggaact ttcagtaata cgcttaactg      60
ctcattgcta tattgaagta cggattagaa gccgccgagc gggtgacagc cctccgaagg    120
aagactctcc tccgtgcgtc ctcgtcttca ccggtcgcgt tcctgaaacg cagatgtgcc    180
tcgcgccgca ctgctccgaa caataaagat tctacaatac tagcttttat ggttatgaag    240
aggaaaaatt ggcagtaacc tggccccaca accttcaaa tgaacgaatc aaattaacaa     300
ccataggatg ataatgcgat tagtttttta gccttatttc tggggtaatt aatcagcgaa    360
gcgatgattt ttgatctatt aacagatata taaatgcaaa aactgcataa ccactttaac    420
taatactttc aacattttcg gtttgtatta cttcttattc aaatgtaata aaagtatcaa    480
caaaaaattg ttaatatacc tctatacttt aacgtcaagg aggaattaag cttatgggtg    540
ctcctccaaa aaagaagaga aaggtagctg gtatcaataa agatatcgag gagtgcaatg    600
ccatcattga gcagtttatc gactacctgc gcaccggaca ggagatgccg atggaaatgg    660
cggatcaggc gattaacgtg gtgccgggca tgacgccgaa aaccattctt cacgccgggc    720
cgccgatcca gctgactggc tgaaatcga atggttttca tgaaattgaa gcggatgtta    780
acgataccag cctcttgctg agtggagatg cctcctaccc ttatgatgtg ccagattatg    840
cctctcccga attcggccga ctcgagaagc tttggacttc ttcgccagag gtttggtcaa    900
gtctccaatc aaggttgtcg gcttgtctac cttgccagaa atttacgaaa agatggaaaa    960
gggtcaaatc gttggtagat acgttgttga cacttctaaa taagcgaatt tcttatgatt   1020
tatgattttt attattaaat aagttataaa aaaataagt gtatacaaat tttaaagtga   1080
ctcttaggtt ttaaaacgaa aattcttgtt cttgagtaac tctttcctgt aggtcaggtt   1140
gctttctcag gtatagcatg aggtcgctct tattgaccac acctctaccg gcatgccgag   1200
caaatgcctg caaatcgctc ccatttcac ccaattgtag atatgctaac tccagcaatg    1260
agttgatgaa tctcggtgtg tatttatgt cctcagagga caacacctgt tgtaatcgtt     1320
cttccacacg gatcctctag agtcgactag cggccgcttc gacctgcagc aattctgaac   1380
cagtcctaaa acgagtaaat aggaccggca attcttcaag caataaacag gaataccaat   1440
tattaaaaga taacttagtc agatcgtaca ataaagcttt gaagaaaat gcgccttatt   1500 caatctttgc tataaaaaat ggcccaaat ctcacattgg aagacatttg atgacctcat    1560
ttctttcaat gaagggccta acggagttga ctaatgttgt gggaaattgg agcgataagc   1620
gtgcttctgc cgtggccagg acaacgtata ctcatcagat aacagcaata cctgatcact   1680

```
acttcgcact agtttctcgg tactatgcat atgatccaat atcaaaggaa atgatagcat    1740
tgaaggatga gactaatcca attgaggagt ggcagcatat agaacagcta aagggtagtg    1800
ctgaaggaag catacgatac cccgcatgga atgggataat atcacaggag gtactagact    1860
acctttcatc ctacataaat agacgcatat aagtacgcat ttaagcataa acacgcacta    1920
tgccgttctt ctcatgtata tatatataca ggcaacacgc agatataggt gcgacgtgaa    1980
cagtgagctg tatgtgcgca gctcgcgttg cattttcgga agcgctcgtt ttcggaaacg    2040
ctttgaagtt cctattccga agttcctatt ctctagaaag tataggaact tcagagcgct    2100
tttgaaaacc aaaagcgctc tgaagacgca ctttcaaaaa accaaaaacg caccggactg    2160
taacgagcta ctaaaatatt gcgaataccg cttccacaaa cattgctcaa agtatctct    2220 ttgctatata tctctgtgct atatccctat ataacctacc catccacctt tcgctccttg    2280
aacttgcatc taaactcgac ctctacattt tttatgttta tctctagtat tactctttag    2340
acaaaaaaat tgtagtaaga actattcata gagtgaatcg aaaacaatac gaaaatgtaa    2400
acatttccta tacgtagtat atagagacaa aatagaagaa accgttcata attttctgac    2460
caatgaagaa tcatcaacgc tatcactttc tgttcacaaa gtatgcgcaa tccacatcgg    2520
tatagaatat aatcggggat gcctttatct tgaaaaaatg cacccgcagc ttcgctagta    2580
atcagtaaac gcgggaagtg gagtcaggct ttttttatgg aagagaaaat agacaccaaa    2640
gtagccttct tctaaccttta acggacctac agtgcaaaaa gttatcaaga gactgcatta    2700
tagagcgcac aaaggagaaa aaagtaatc taagatgctt tgttagaaaa atagcgctct    2760
cgggatgcat ttttgtagaa caaaaagaa gtatagattc tttgttggta aaatagcgct    2820
ctcgcgttgc atttctgttc tgtaaaaatg cagctcagat tctttgtttg aaaaattagc    2880
gctctcgcgt tgcatttttg ttttacaaaa atgaagcaca gattcttcgt tggtaaaata    2940 gcgcttcgc gttgcatttc tgttctgtaa aaatgcagct cagattcttt gtttgaaaaa    3000
ttagcgctct cgcgttgcat ttttgttcta caaaatgaag cacagatgct tcgttaacaa    3060
agatatgcta ttgaagtgca agatggaaac gcagaaaatg aaccgggat gcgacgtgca    3120 agattaccta tgcaatagat gcaatagttt ctccaggaac cgaaatacat acattgtctt    3180
ccgtaaagcg ctagactata tattattata caggttcaaa tatactatct gtttcaggga    3240
aaactcccag gttcggatgt tcaaaattca atgatgggta acaagtacga tcgtaaatct    3300
gtaaaacagt ttgtcggata ttaggctgta tctcctcaaa gcgtattcga tctgtctttc    3360
gccgaaacct gtttgatgac tacttcatca attttttttt tttctgccgc attccaaagg    3420
tcataacttt gcaaaaataa agggtaaatg gttaaaaatt gttatcataa ataaggtgac    3480
cggttatatt gagacctttc ctggacagta actaatacag aagccattgg taatgcaata    3540
atttatttga tcatgtgact acgatccggg tgagactatt caaaaaagga gtcaagcatt    3600
gaaataatta atgactaatc cgaagttaat tgttaggagt caattgtttt ttccaatgaa    3660
tggaatctga gatgactaaa ctaccaattt tcaatagttc atggtatagt gacgtagtta    3720 gtgcttttt ttcttggatc tgttgactca cttcaattga tgtttcttac cctgacatga    3780
catacttgat attttatctc tcacgttata taacttgaaa aggatgcaca cagttctgtt    3840
caatataccc tccaatatgt aaaaacagtt tttccattga ttactcttaa tttgtttcct    3900
gctaaaccag cagtacgtgt gtgccgtata tattaaaatt acactatggt ttttgatttg    3960
aaaagaattg ttagaccaaa aatttataac ttggaacctt atcgctgtgc aagagatgat    4020
ttcaccgagg gtatattgct agacgccaat gaaaatgccc atggacctac tccagttgaa    4080
```

-continued

```
ttgagcaaga ccaatttaca tcgttacccg gatcctcacc aattggagtt caagaccgca   4140
atgacgaaat acaggaacaa acaagcagt tatgccaatg acccagaggt aaaacctta    4200 actgctgaca atctgtgcct aggtgtggga tctgatgaga gtattgatgc tattattaga   4260
gcatgctgtg ttcccgggaa agaaaagatt ctggttcttc caccaacata ttctatgtac   4320
tctgtttgtg caaacattaa tgatatagaa gtcgtccaat gtcctttaac tgtttccgac   4380
ggttcttttc aaatggatac cgaagctgta ttaaccattt tgaaaaacga ctcgctaatt   4440
aagttgatgt tcgttacttc accaggtaat ccaaccggag ccaaaattaa gaccagttta   4500
atcgaaaagg tcttacagaa ttgggacaat gggttagtcg ttgttgatga agcttacgta   4560 gattttgtg gtggctctac agctccacta gtcaccaagt atcctaactt ggttactttg    4620
caaactctat ccaagtcatt cggtttagcc gggattaggt tgggtatgac atatgcaaca   4680
gcagagttgg ccagaatttt aaatgcaatg aaggcgcctt ataatattc ctccctagcc    4740 tctgaatatg cactaaaagc tgttcaagac agtaatctaa agaagatgga agccacttcg   4800
aaaataatca atgaagagaa aatgcgcctc ttaaaggaat taactgcttt ggattacgtt   4860
gatgaccaat atgttggtgg attagatgct aattttcttt taatacggat caacgggggt   4920
gacaatgtct tggcaaagaa gttatattac caattggcta ctcaatctgg ggttgtcgtc   4980
agatttagag gtaacgaatt aggctgttcc ggatgtttga gaattaccgt tggaacccat   5040
gaggagaaca cacatttgat aaagtacttc aaggagacgt tatataagct ggccaatgaa   5100
taaatagacg tcaacaaaat tcagaagaac tcgtcaagaa ggcgatagaa ggcgatgcgc   5160
tgcgaatcgg gagcggcgat accgtaaagc acgaggaagc ggtcagccca ttcgccgcca   5220
agctcttcag caatatcacg ggtagccaac gctatgtcct gatagcggtc cgccacaccc   5280
agccggccac agtcgatgaa tccagaaaag cggccatttt ccaccatgat attcggcaag   5340
caggcatcgc catgggtcac gacgagatcc tcgccgtcgg catgctcgc cttgagcctg    5400 gcgaacagtt cggctggcgc gagcccctga tgctcttcgt ccagatcatc ctgatcgaca   5460
agaccggctt ccatccgagt acgtgctcgc tcgatgcgat gtttcgcttg gtggtcgaat   5520
gggcaggtag ccggatcaag cgtatgcagc cgccgcattg catcagccat gatggatact   5580
ttctcggcag gagcaaggtg agatgacagg agatcctgcc ccggcacttc gcccaatagc   5640
agccagtccc ttcccgcttc agtgacaacg tcgagcacag ctgcgcaagg aacgcccgtc   5700
gtggccagcc acgatagccg cgctgcctcg tcttgcagtt cattcagggc accggacagg   5760
tcggtcttga caaaaagaac cgggcgcccc tgcgctgaca gccggaacac ggcggcatca   5820
gagcagccga ttgtctgttg tgcccagtca tagccgaata gcctctccac ccaagcggcc   5880
ggagaacctg cgtgcaatcc atcttgttca atcatgcgaa acgatcctca tcctgtctct   5940
tgatcagatc ttgatcccct gcgccatcag atccttggcg gcgagaaagc catccagttt   6000
actttgcagg gcttcccaac cttaccagag ggcgccccag ctggcaattc cggttcgctt   6060
gctgtccata aaaccgccca gtctagctat cgccatgtaa gcccactgca agctacctgc   6120
tttctctttg cgcttgcgtt ttcccttgtc cagatagccc agtagctgac attcatccgg   6180
ggtcagcacc gttctgcgg actggctttc tacgtgaaaa ggatctaggt gaagatcctt   6240
tttgataatc tcatgaccaa atcccttaa cgtgagtttt cgtgactccc cgtcaggcaa    6300
ctatggatga acgaaataga cagatcgctg agataggtgc ctcactgatt aagcattggt   6360
aactgtcaga ccaagtttac tcatatatac tttagattga tttaaaactt catttttaat   6420
```

-continued

| | |
|---|---|
| ttaaaaggat ctaggtgaag atccttttg ataatctcat gaccaaaatc ccttaacgtg | 6480 |
| agttttcgtt ccactgagcg tcagacccg tagaaaagat caaaggatct tcttgagatc | 6540 |
| cttttttct gcgcgtaatc tgctgcttgc aaacaaaaaa accaccgcta ccagcggtgg | 6600 |
| tttgtttgcc ggatcaagag ctaccaactc ttttccgaa ggtaactggc ttcagcagag | 6660 |
| cgcagatacc aaatactgtc cttctagtgt agccgtagtt aggccaccac ttcaagaact | 6720 |
| ctgtagcacc gcctacatac ctcgctctgc taatcctgtt accagtggct gctgccagtg | 6780 |
| gcgataagtc gtgtcttacc gggttggact caagacgata gttaccggat aaggcgcagc | 6840 |
| ggtcgggctg aacggggggt tcgtgcacac agcccagctt ggagcgaacg acctacaccg | 6900 |
| aactgagata cctacagcgt gagctatgag aaagcgccac gcttcccgaa gggagaaagg | 6960 |
| cggacaggta tccggtaagc ggcagggtcg aacaggaga gcgcacgagg gagcttccag | 7020 |
| ggggaaacgc ctggtatctt tatagtcctg tcgggtttcg ccacctctga cttgagcgtc | 7080 |
| gatttttgtg atgctcgtca gggggcgga gcctatggaa aaacgccagc aacgcggcct | 7140 |
| ttttacggtt cctggccttt tgctggcctt ttgctcacat gttctttcct gcgttatccc | 7200 |
| ctgattctgt ggataaccgt attaccgcct ttgagtgagc tgataccgct cgccgcagcc | 7260 |
| gaacgaccga gcgcagcgag tcagtgagcg aggaagcgga agagcgccca atacgcaaac | 7320 |
| cgcctctccc cgcgcgttgg ccgattcatt aatgcagctg gcacgacagg tttcccgact | 7380 |
| ggaaagcggg cagtgagcgc aacgcaatta atgtgagtta gctcactcat taggcacccc | 7440 |
| aggctttaca ctttatgctt ccggctcgta tgttgtgtgg aattgtgagc ggataacaat | 7500 |
| ttcacacagg aaacagctat gacatgatta cgaattaatt cgagctcggt a | 7551 |

<210> SEQ ID NO 61
<211> LENGTH: 7308
<212> TYPE: DNA
<213> ORGANISM: Artificial Sequence
<220> FEATURE:
<223> OTHER INFORMATION: synthetic pDD vector

<400> SEQUENCE: 61

| | |
|---|---|
| cttgaatttt caaaaattct tactttttt ttggatggac gcaaagaagt ttaataatca | 60 |
| tattacatgg cattaccacc atatacatat ccatatacat atccatatct aatcttactt | 120 |
| atatgttgtg gaaatgtaaa gagccccatt atcttagcct aaaaaaacct tctctttgga | 180 |
| actttcagta atacgcttaa ctgctcattg ctatattgaa gtacggatta gaagccgccg | 240 |
| agcgggtgac agccctccga aggaagactc tcctccgtgc gtcctcgtct tcaccggtcg | 300 |
| cgttcctgaa acgcagatgt gcctcgcgcc gcactgctcc gaacaataaa gattctacaa | 360 |
| tactagcttt tatggttatg aagaggaaaa attggcagta acctggcccc acaaaccttc | 420 |
| aaatgaacga atcaaattaa caaccatagg atgataatgc gattagtttt ttagccttat | 480 |
| ttctggggta attaatcagc gaagcgatga ttttgatct attaacagat atataaatgc | 540 |
| aaaaactgca taaccacttt aactaatact ttcaacattt tcggtttgta ttacttctta | 600 |
| ttcaaatgta ataaaagtat caacaaaaaa ttgttaatat acctctatac tttaacgtca | 660 |
| aggagaaaaa accccggatc aagggtgcga tatgaaagcg ttaacggcca gcaacaaga | 720 |
| ggtgtttgat ctcatccgtg atcacatcag ccagacaggt atgccgccga cgcgtgcgga | 780 |
| aatcgcgcag cgtttggggt tccgttcccc aaacgcggct gaagaacatc tgaaggcgct | 840 |
| ggcacgcaaa ggcgttattg aaattgtttc cggcgcatca cgcggattc gtctgttgca | 900 |
| ggaagaggaa gaagggttgc cgctggtagg tcgtgtggct gccggtgaac cacttctggc | 960 |

-continued

```
gcaacagcat attgaaggtc attatcaggt cgatccttcc ttattcaagc cgaatgctga    1020
tttcctgctg cgcgtcagcg ggatgtcgat gaaagatatc ggcattatgg atggtgactt    1080
gctggcagtg cataaaactc aggatgtacg taacggtcag gtcgttgtcg cacgtattga    1140
tgacgaagtt accgttaagc gcctgaaaaa acagggcaat aaagtcgaac tgttgccaga    1200
aaatagcgag tttaaaccaa ttgtcgtaga tcttcgtcag cagagcttca ccattgaagg    1260
gctggcggtt ggggttattc gcaacggcga ctggctggaa ttcccgggga tccgtcgacc    1320
atggcggccg ctcgagtcga cctgcagcca agctaattcc gggcgaattt cttatgattt    1380 atgatttta ttattaaata agttataaaa aaataagtg tatacaaatt ttaaagtgac    1440
tcttaggttt taaaacgaaa attcttgttc ttgagtaact ctttcctgta ggtcaggttg    1500
ctttctcagg tatagcatga ggtcgctctt attgaccaca cctctaccgg catgccgagc    1560
aaatgcctgc aaatcgctcc ccatttcacc caattgtaga tatgctaact ccagcaatga    1620
gttgatgaat ctcggtgtgt attttatgtc ctcagaggac aacacctgtt gtaatccgtc    1680
cgagctccaa ttcgccctat agtgagtcgt attacaattc actggccgtc gttttacaac    1740
gtcgtgactg ggaaaaccct ggcgttaccc aacttaatcg ccttgcagca catccccctt    1800
tcgccagctg gcgtaatagc gaagaggccc gcaccgatcg cccttcccaa cagttgcgca    1860
gcctgaatgg cgaatggcgc gacgcgccct gtagcggcgc attaagcgcg gcgggtgtgg    1920
tggttacgcg cagcgtgacc gctacacttg ccagcgccct agcgcccgct cctttcgctt    1980
tcttcccttc ctttctcgcc acgttcgccg gctttccccg tcaagctcta aatcggggggc    2040 tccctttagg gttccgattt agtgctttac ggcacctcga cccccaaaaaa cttgattagg    2100 gtgatggttc acgtagtggg ccatcgccct gatagacggt ttttcgccct ttgacgttgg    2160
agtccacgtt ctttaatagt ggactcttgt tccaaactgg aacaacactc aaccctatct    2220
cggtctattc ttttgattta agggggattt tgccgatttc ggcctattgg ttaaaaaatg    2280
agctgattta acaaaaattt aacgcgaatt ttaacaaaat attaacgttt acaatttcct    2340
gatgcggtat tttctcctta cgcatctgtg cggtatttca caccgcatat gatccgtcga    2400
gttcaagaga aaaaaaaga aaagcaaaa agaaaaaagg aaagcgcgcc tcgttcagaa    2460
tgacacgtat agaatgatgc attaccttgt catcttcagt atcatactgt tcgtatacat    2520
acttactgac attcataggt atacatatat acacatgtat atatatcgta tgctgcagct    2580
ttaaataatc ggtgtcacta cataagaaca cctttggtgg agggaacatc gttggtacca    2640
ttgggcgagg tggcttctct tatggcaacc gcaagagcct gaacgcact ctcactacgg    2700 tgatgatcat tcttgcctcg cagacaatca acgtggaggg taattctgct agcctctgca    2760 aagcttttcaa gaaatgcgg gatcatctcg caagagagat ctcctacttt ctcccctttgc    2820 aaaccaagtt cgacaactgc gtacggcctg ttcgaaagat ctaccaccgc tctggaaagt    2880
gcctcatcca aaggcgcaaa tcctgatcca aacctttta ctccacgcgc cagtagggcc    2940
tctttaaaag cttgaccgag agcaatcccg cagtcttcag tggtgtgatg gtcgtctatg    3000
tgtaagtcac caatgcactc aacgattagc gaccagccgg aatgcttggc cagagcatgt    3060
atcatatggt ccagaaaccc tatacctgtg tggacgttaa tcacttgcga ttgtgtggcc    3120
tgttctgcta ctgcttctgc ctcttttttct gggaagatcg agtgctctat cgctagggga    3180
ccacccttta aagagatcgc aatctgaatc ttggtttcat ttgtaatacg ctttactagg    3240
gctttctgct ctgtcatctt tgccttcgtt tatcttgcct gctcatttttt tagtatattc    3300
```

-continued

```
ttcgaagaaa tcacattact ttatataatg tataattcat tatgtgataa tgccaatcgc    3360
taagaaaaaa aaagagtcat ccgctaggtg gaaaaaaaaa aatgaaaatc attaccgagg    3420
cataaaaaaa tatagagtgt actagaggag gccaagagta atagaaaaag aaaattgcgg    3480
gaaaggactg tgttatgact tccctgacta atgccgtgtt caaacgatac ctggcagtga    3540
ctcctagcgc tcaccaagct cttaaaacgg aattatggtg cactctcagt acaatctgct    3600
ctgatgccgc atagttaagc cagccccgac acccgccaac acccgctgac gcgccctgac    3660
gggcttgtct gctcccggca tccgcttaca gacaagctgt gaccgtctcc gggagctgca    3720
tgtgtcagag gttttcaccg tcatcaccga acgcgcgag acgaaagggc ctcgtgatac    3780
gcctattttt ataggttaat gtcatgataa taatggtttc ttaggacgga tcgcttgcct    3840
gtaacttaca cgcgcctcgt atcttttaat gatggaataa tttgggaatt tactctgtgt    3900
ttatttattt ttatgttttg tatttggatt ttagaaagta aataaagaag gtagaagagt    3960 tacgaatga agaaaaaaaa ataaacaaag gtttaaaaaa tttcaacaaa aagcgtactt    4020
tacatatata tttattagac aagaaaagca gattaaatag atatacattc gattaacgat    4080
aagtaaaatg taaaatcaca ggattttcgt gtgtggtctt ctacacagac aagatgaaac    4140
aattcggcat taatacctga gagcaggaag agcaagataa aaggtagtat tgttggcga    4200 tcccctaga gtcttttaca tcttcggaaa acaaaaacta ttttttcttt aatttctttt    4260
tttactttct atttttaatt tatatattta tattaaaaaa tttaaattat aattattttt    4320
atagcacgtg atgaaaagga cccaggtggc acttttcggg gaaatgtgcg cggaacccct    4380
atttgtttat ttttctaaat acattcaaat atgtatccgc tcatgagaca ataaccctga    4440
taaatgcttc aataaattgg tcacccggcc agcgacatgg aggcccagaa taccctcctt    4500
gacagtcttg acgtgcgcag ctcaggggca tgatgtgact gtcgcccgta catttagccc    4560
atacatcccc atgtataatc atttgcatcc atacattttg atggccgcac ggcgcgaagc    4620
aaaaattacg gctcctcgct gcagacctgc gagcagggaa acgctcccct cacagacgcg    4680
ttgaattgtc cccacgccgc gcccctgtag agaaatataa aaggttagga tttgccactg    4740
aggttcttct ttcatatact tccttttaaa atcttgctag gatacagttc tcacatcaca    4800
tccgaacata aacaaccatg ggtaaggaaa agactcacgt ttcgaggccg cgattaaatt    4860
ccaacatgga tgctgattta tatgggtata atgggctcg cgataatgtc gggcaatcag    4920
gtgcgacaat ctatcgattg tatgggaagc ccgatgcgcc agagttgttt ctgaaacatg    4980
gcaaaggtag cgttgccaat gatgttacag atgagatggt cagactaaac tggctgacgg    5040
aatttatgcc tcttccgacc atcaagcatt ttatccgtac tcctgatgat gcatggttac    5100
tcaccactgc gatccccggc aaaacagcat tccaggtatt agaagaatat cctgattcag    5160
gtgaaaatat tgttgatgcg ctggcagtgt tcctgcgccg gttgcattcg attcctgttt    5220
gtaattgtcc ttttaacagc gatcgcgtat ttcgtctcgc tcaggcgcaa tcacgaatga    5280
ataacggttt ggttgatgcg agtgattttg atgacgagcg taatggctgg cctgttgaac    5340
aagtctggaa agaaatgcat aagcttttgc cattctcacc ggattcagtc gtcactcatg    5400
gtgatttctc acttgataac cttattttg acgaggggaa attaataggt tgtattgatg    5460
ttggacgagt cggaatcgca gaccgatacc aggatcttgc catcctatgg aactgcctcg    5520
gtgagttttc tccttcatta cagaaacggc ttttttcaaaa atatggtatt gataatcctg    5580
atatgaataa attgcagttt catttgatgc tcgatgagtt tttctaatca gtcctcggag    5640
atccgtcccc cttttccttt gtcgatatca tgtaattagt tatgtcacgc ttacattcac    5700
```

-continued

```
gccctccccc cacatccgct ctaaccgaaa aggaaggagt tagacaacct gaagtctagg    5760
tccctattta ttttttttata gttatgttag tattaagaac gttatttata tttcaaattt    5820 ttctttttttt tctgtacaga cgcgtgtacg catgtaacat tatactgaaa accttgcttg    5880
agaaggtttt gggacgctcg aaggctttaa tttgcaagct ggggtctcgc ggtcggtatc    5940
attgcagcac tggggccaga tggtaagccc tcccgtatcg tagttatcta cacgacgggc    6000
agtcaggcaa ctatggatga acgaaataga cagatcgctg agataggtgc ctcactgatt    6060
aagcattggt aactgtcaga ccaagtttac tcatatatac tttagattga tttaaaactt    6120 cattttttaat ttaaaaggat ctaggtgaag atccttttttg ataatctcat gaccaaaatc    6180
ccttaacgtg agttttcgtt ccactgagcg tcagacccccg tagaaaagat caaaggatct    6240
tcttgagatc cttttttttct gcgcgtaatc tgctgcttgc aaacaaaaaa accaccgcta    6300
ccagcggtgg tttgtttgcc ggatcaagag ctaccaactc tttttccgaa ggtaactggc    6360
ttcagcagag cgcagatacc aaatactgtc cttctagtgt agccgtagtt aggccaccac    6420
ttcaagaact ctgtagcacc gcctacatac ctcgctctgc taatcctgtt accagtggct    6480
gctgccagtg gcgataagtc gtgtcttacc gggttggact caagacgata gttaccggat    6540
aaggcgcagc ggtcgggctg aacggggggt tcgtgcacac agcccagctt ggagcgaacg    6600
acctacaccg aactgagata cctacagcgt gagcattgag aaagcgccac gcttcccgaa    6660
gggagaaagg cggacaggta tccggtaagc ggcagggtcg gaacaggaga gcgcacgagg    6720
gagcttccag gggggaacgc ctggtatctt tatagtcctg tcgggtttcg ccacctctga    6780
cttgagcgtc gatttttgtg atgctcgtca ggggggccga gcctatggaa aaacgccagc    6840
aacgcggcct ttttacggtt cctggccttt tgctggcctt tgctcacat gttctttcct    6900 gcgttatccc ctgattctgt ggataaccgt attaccgcct ttgagtgagc tgataccgct    6960
cgccgcagcc gaacgaccga gcgcagcgag tcagtgagcg aggaagcgga agagcgccca    7020
atacgcaaac cgcctctccc cgcgcgttgg ccgattcatt aatgcagctg gcacgacagg    7080
tttcccgact ggaaagcggg cagtgagcgc aacgcaatta atgtgagtta gctcactcat    7140 taggcaccccc aggctttaca ctttatgctt ccggctcgta tgttgtgtgg aattgtgagc    7200
ggataacaat ttcacacagg aaacagctat gaccatgatt accccaagct cgaaattaac    7260
cctcactaaa gggaacaaaa gctggtaccg ggccccccct cgaaattc              7308
```

<210> SEQ ID NO 62
<211> LENGTH: 289
<212> TYPE: DNA
<213> ORGANISM: Artificial Sequence
<220> FEATURE:
<221> NAME/KEY: CDS
<222> LOCATION: (1)...(165)
<220> FEATURE:
<223> OTHER INFORMATION: synthetic clone BGF05 with first open reading
      frame

<400> SEQUENCE: 62

```
atg ggt aag cct atc cct aac cct ctc ctc ggt ctc gat tct aca caa      48
Met Gly Lys Pro Ile Pro Asn Pro Leu Leu Gly Leu Asp Ser Thr Gln
1               5                   10                  15 gct atg ggt gct cct cca aaa aag aag aga aag gta gct gaa ttc gca      96
Ala Met Gly Ala Pro Pro Lys Lys Lys Arg Lys Val Ala Glu Phe Ala
            20                  25                  30 agg acg acg acg aca agg ctt atc aat caa tca gtg gtt aga aaa ata     144
Arg Thr Thr Thr Thr Arg Leu Ile Asn Gln Ser Val Val Arg Lys Ile
```

```
              35                  40                  45
tgg cta tat cga gat gca agg taacgaaacg ttcaaattgg cagttcgtga          195
Trp Leu Tyr Arg Asp Ala Arg
        50                  55 actttcaaat gtggtggaag aaacactttt agccaataat ttagataaaa aagatttaga    255
ctggcttgtc gtcgtcgtcc ttgtagtctg acct                                289

<210> SEQ ID NO 63
<211> LENGTH: 55
<212> TYPE: PRT
<213> ORGANISM: Artificial Sequence
<220> FEATURE:
<223> OTHER INFORMATION: synthetic clone BGF05 with first open reading
      frame

<400> SEQUENCE: 63

Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Ala
            20                  25                  30

Arg Thr Thr Thr Thr Arg Leu Ile Asn Gln Ser Val Val Arg Lys Ile
        35                  40                  45

Trp Leu Tyr Arg Asp Ala Arg
    50                  55

<210> SEQ ID NO 64
<211> LENGTH: 196
<212> TYPE: DNA
<213> ORGANISM: Artificial Sequence
<220> FEATURE:
<223> OTHER INFORMATION: synthetic BGF05 H. influenzae insertion

<400> SEQUENCE: 64
gcaaggacga cgacgacaag gcttatcaat caatcagtgg ttagaaaaat atggctatat    60
cgagatgcaa ggtaacgaaa cgttcaaatt ggcagttcgt gaactttcaa atgtggtgga    120
agaaacactt ttagccaata atttagataa aaagattta gactggcttg tcgtcgtcgt    180
ccttgtagtc tgacct                                                     196

<210> SEQ ID NO 65
<211> LENGTH: 24
<212> TYPE: PRT
<213> ORGANISM: Artificial Sequence
<220> FEATURE:
<223> OTHER INFORMATION: synthetic SCL-E47 antagonist encoded by
      BGF05 H. influenzae insertion

<400> SEQUENCE: 65

Ala Arg Thr Thr Thr Thr Arg Leu Ile Asn Gln Ser Val Val Arg Lys
1               5                   10                  15

Ile Trp Leu Tyr Arg Asp Ala Arg
            20

<210> SEQ ID NO 66
<211> LENGTH: 419
<212> TYPE: DNA
<213> ORGANISM: Artificial Sequence
<220> FEATURE:
<223> OTHER INFORMATION: synthetic clone BGF06 with first open reading
      frame
<220> FEATURE:
<221> NAME/KEY: CDS
<222> LOCATION: (1)...(165)
```

```
<220> FEATURE:
<221> NAME/KEY: misc_feature
<222> LOCATION: 307, 355, 357
<223> OTHER INFORMATION: n = A,T,C or G

<400> SEQUENCE: 66 atg ggt aag cct atc cct aac cct ctc ctc ggt ctc gat tct aca caa      48
Met Gly Lys Pro Ile Pro Asn Pro Leu Leu Gly Leu Asp Ser Thr Gln
1               5                   10                  15 gct atg ggt gct cct cca aaa aag aag aga aag gta gct gaa ttc agg      96
Ala Met Gly Ala Pro Pro Lys Lys Lys Arg Lys Val Ala Glu Phe Arg
            20                  25                  30 tca gac tac aag gac gac gac gac aag gct tat cac ata att gct gtt     144
Ser Asp Tyr Lys Asp Asp Asp Asp Lys Ala Tyr His Ile Ile Ala Val
        35                  40                  45 tgt ttt tta atc aag gta tca tgacatgtcc caacctcgcc cactgctctc        195
Cys Phe Leu Ile Lys Val Ser
    50                  55 tcctcccgaa actgaagaac agttgttagc gcaagcacag caactttctg gttatacatt   255
gggagaactg gcggcacttg tcgggctggt tacgccagag aatttaaaac gngataaagg   315
ctggattggc gtgttactgg agatctggct aggtgccagn gnagggagta aacctgagca   375
agattttgct gttaatacac ctgattgat tgataaccttgtcg                      419

<210> SEQ ID NO 67
<211> LENGTH: 55
<212> TYPE: PRT
<213> ORGANISM: Artificial Sequence
<220> FEATURE:
<223> OTHER INFORMATION: synthetic clone BGF06 with first open reading
      frame

<400> SEQUENCE: 67

Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Arg
            20                  25                  30

Ser Asp Tyr Lys Asp Asp Asp Asp Lys Ala Tyr His Ile Ile Ala Val
        35                  40                  45

Cys Phe Leu Ile Lys Val Ser
    50                  55

<210> SEQ ID NO 68
<211> LENGTH: 326
<212> TYPE: DNA
<213> ORGANISM: Artificial Sequence
<220> FEATURE:
<221> NAME/KEY: misc_feature
<222> LOCATION: 214, 262, 264
<223> OTHER INFORMATION: n = A,T,C or G
<220> FEATURE:
<223> OTHER INFORMATION: synthetic clone BGF06 A. aeolicus insertion

<400> SEQUENCE: 68
aggtcagact acaaggacga cgacgacaag gcttatcaca taattgctgt ttgtttttta    60
atcaaggtat catgacatgt cccaacctcg cccactgctc tctcctcccg aaactgaaga   120
acagttgtta gcgcaagcac agcaactttc tggttataca ttgggagaac tggcggcact   180
tgtcgggctg gttacgccag agaatttaaa acgngataaa ggctggattg cgtgttact    240 ggagatctgg ctaggtgcca gngnagggag taaacctgag caagattttg ctgttgaata   300
cacctgattg attgataacc ttgtcg                                        326
```

<210> SEQ ID NO 69
<211> LENGTH: 24
<212> TYPE: PRT
<213> ORGANISM: Artificial Sequence
<220> FEATURE:
<223> OTHER INFORMATION: synthetic SCL-E47 antagonist encoded by clone
      BGF06 A. aeolicus insertion

<400> SEQUENCE: 69

```
Arg Ser Asp Tyr Lys Asp Asp Asp Lys Ala Tyr His Ile Ile Ala
1               5                   10                  15

Val Cys Phe Leu Ile Lys Val Ser
            20
```

<210> SEQ ID NO 70
<211> LENGTH: 220
<212> TYPE: DNA
<213> ORGANISM: Artificial Sequence
<220> FEATURE:
<221> NAME/KEY: CDS
<222> LOCATION: (1)...(123)
<220> FEATURE:
<223> OTHER INFORMATION: synthetic clone BGF13 with first open reading
      frame

<400> SEQUENCE: 70

```
atg ggt aag cct atc cct aac cct ctc ctc ggt ctc gat tct aca caa        48
Met Gly Lys Pro Ile Pro Asn Pro Leu Leu Gly Leu Asp Ser Thr Gln
1               5                   10                  15 gct atg ggt gct cct cca aaa aag aag aga aag gta gct gaa ttc gga        96
Ala Met Gly Ala Pro Pro Lys Lys Lys Arg Lys Val Ala Glu Phe Gly
            20                  25                  30 ttt tgc tct aat caa atg aga gaa atg taaaatgaag ccacgaacat              143
Phe Cys Ser Asn Gln Met Arg Glu Met
        35                  40 attaataata gcctaccact gcaaccatta gttcctgatc aggagaacaa aaataagaga      203
aatgaagaga aatccgt                                                     220
```

<210> SEQ ID NO 71
<211> LENGTH: 41
<212> TYPE: PRT
<213> ORGANISM: Artificial Sequence
<220> FEATURE:
<223> OTHER INFORMATION: synthetic clone BGF13 with first open reading
      frame

<400> SEQUENCE: 71

```
Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Gly
            20                  25                  30

Phe Cys Ser Asn Gln Met Arg Glu Met
        35                  40
```

<210> SEQ ID NO 72
<211> LENGTH: 127
<212> TYPE: DNA
<213> ORGANISM: Artificial Sequence
<220> FEATURE:
<223> OTHER INFORMATION: synthetic clone BGF13 H. influenzae insertion

<400> SEQUENCE: 72

```
ggattttgct ctaatcaaat gagagaaatg taaaatgaag ccacgaacat attaataata      60
```

```
gcctaccact gcaaccatta gttcctgatc aggagaacaa aaataagaga aatgaagaga      120
aatccgt                                                               127
```

<210> SEQ ID NO 73
<211> LENGTH: 10
<212> TYPE: PRT
<213> ORGANISM: Artificial Sequence
<220> FEATURE:
<223> OTHER INFORMATION: synthetic SCL-E47 antagonist encoded by clone
      BGF13 H. influenzae insertion

<400> SEQUENCE: 73

Gly Phe Cys Ser Asn Gln Met Arg Glu Met
1               5                   10

<210> SEQ ID NO 74
<211> LENGTH: 273
<212> TYPE: DNA
<213> ORGANISM: Artificial Sequence
<220> FEATURE:
<221> NAME/KEY: CDS
<222> LOCATION: (1)...(171)
<220> FEATURE:
<223> OTHER INFORMATION: synthetic clone BGF24 with first open reading
      frame

<400> SEQUENCE: 74

```
atg ggt aag cct atc cct aac cct ctc ctc ggt ctc gat tct aca caa       48
Met Gly Lys Pro Ile Pro Asn Pro Leu Leu Gly Leu Asp Ser Thr Gln
1               5                   10                  15 gct atg ggt gct cct cca aaa aag aag aga aag gta gct gaa ttc agg       96
Ala Met Gly Ala Pro Pro Lys Lys Lys Arg Lys Val Ala Glu Phe Arg
                20                  25                  30 tca gac tac aag gac gac gac gac aag ctt atc aaa cat cac tgg gtg      144
Ser Asp Tyr Lys Asp Asp Asp Asp Lys Leu Ile Lys His His Trp Val
        35                  40                  45 ctt tca atc atc acc acc gcg tct cgc taacctgttt caaataccac            191
Leu Ser Ile Ile Thr Thr Ala Ser Arg
    50                  55 catgaactcc tctccaccgt atcttgacta caagggatga ttgattgata agccttgtcg    251
tcgtcgtcct tgtagtctga ct                                             273
```

<210> SEQ ID NO 75
<211> LENGTH: 57
<212> TYPE: PRT
<213> ORGANISM: Artificial Sequence
<220> FEATURE:
<223> OTHER INFORMATION: synthetic clone BGF24 with first open reading
      frame

<400> SEQUENCE: 75

Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Arg
                20                  25                  30

Ser Asp Tyr Lys Asp Asp Asp Asp Lys Leu Ile Lys His His Trp Val
        35                  40                  45

Leu Ser Ile Ile Thr Thr Ala Ser Arg
    50                  55

<210> SEQ ID NO 76
<211> LENGTH: 180

<212> TYPE: DNA
<213> ORGANISM: Artificial Sequence
<220> FEATURE:
<223> OTHER INFORMATION: synthetic clone BGF24 T. maritima insertion

<400> SEQUENCE: 76

```
aggtcagact acaaggacga cgacgacaag cttatcaaac atcactgggt gctttcaatc      60
atcaccaccg cgtctcgcta acctgtttca aataccacca tgaactcctc tccaccgtat    120
cttgactaca aggatgatt gattgataag ccttgtcgtc gtcgtccttg tagtctgact      180
```

<210> SEQ ID NO 77
<211> LENGTH: 26
<212> TYPE: PRT
<213> ORGANISM: Artificial Sequence
<220> FEATURE:
<223> OTHER INFORMATION: synthetic SCL-E47 antagonist encoded by clone
      BGF24 T. maritima insertion

<400> SEQUENCE: 77

```
Arg Ser Asp Tyr Lys Asp Asp Asp Lys Leu Ile Lys His His Trp
1               5                   10                  15
Val Leu Ser Ile Ile Thr Thr Ala Ser Arg
            20                  25
```

<210> SEQ ID NO 78
<211> LENGTH: 288
<212> TYPE: DNA
<213> ORGANISM: Artificial Sequence
<220> FEATURE:
<221> NAME/KEY: CDS
<222> LOCATION: (1)...(282)
<220> FEATURE:
<223> OTHER INFORMATION: synthetic clone BGF35 with first open reading
      frame

<400> SEQUENCE: 78

```
atg ggt aag cct atc cct aac cct ctc ctc ggt ctc gat tct aca caa      48
Met Gly Lys Pro Ile Pro Asn Pro Leu Leu Gly Leu Asp Ser Thr Gln
1               5                   10                  15 gct atg ggt gct cct cca aaa aag aag aga aag gta gct gaa ttc caa      96
Ala Met Gly Ala Pro Pro Lys Lys Lys Arg Lys Val Ala Glu Phe Gln
                20                  25                  30 gga cga cga cga caa ggc tta tca atc aat cag tgg tta gaa aaa tat     144
Gly Arg Arg Arg Gln Gly Leu Ser Ile Asn Gln Trp Leu Glu Lys Tyr
            35                  40                  45 ggc tat atc gag atg caa ggt aac gaa acg ttc aaa ttg gca gtt cgt     192
Gly Tyr Ile Glu Met Gln Gly Asn Glu Thr Phe Lys Leu Ala Val Arg
        50                  55                  60 gaa ctt tca aat gtg gtg gaa gaa aca ctt tta gcc aat aat tta gat     240
Glu Leu Ser Asn Val Val Glu Glu Thr Leu Leu Ala Asn Asn Leu Asp
65                  70                  75                  80 aaa aaa gat tta gac tgg ctt gtc gtc gtc gtc ctt gta gtc                282
Lys Lys Asp Leu Asp Trp Leu Val Val Val Val Leu Val Val
                85                  90 tgacct                                                                288
```

<210> SEQ ID NO 79
<211> LENGTH: 94
<212> TYPE: PRT
<213> ORGANISM: Artificial Sequence
<220> FEATURE:
<223> OTHER INFORMATION: synthetic clone BGF35 with first open reading
      frame

<400> SEQUENCE: 79

-continued

```
Met Gly Lys Pro Ile Pro Asn Pro Leu Leu Gly Leu Asp Ser Thr Gln
1               5                   10                  15

Ala Met Gly Ala Pro Pro Lys Lys Lys Arg Lys Val Ala Glu Phe Gln
                20                  25                  30

Gly Arg Arg Arg Gln Gly Leu Ser Ile Asn Gln Trp Leu Glu Lys Tyr
            35                  40                  45

Gly Tyr Ile Glu Met Gln Gly Asn Glu Thr Phe Lys Leu Ala Val Arg
        50                  55                  60

Glu Leu Ser Asn Val Val Glu Glu Thr Leu Leu Ala Asn Asn Leu Asp
65                  70                  75                  80

Lys Lys Asp Leu Asp Trp Leu Val Val Val Val Leu Val Val
                85                  90
```

<210> SEQ ID NO 80
<211> LENGTH: 195
<212> TYPE: DNA
<213> ORGANISM: Artificial Sequence
<220> FEATURE:
<223> OTHER INFORMATION: synthetic clone BGF35 H. influenzae insertion

<400> SEQUENCE: 80

```
caaggacgac gacgacaagg cttatcaatc aatcagtggt tagaaaaata tggctatatc      60
gagatgcaag gtaacgaaac gttcaaattg gcagttcgtg aactttcaaa tgtggtggaa     120
gaaacacttt tagccaataa tttagataaa aaagatttag actggcttgt cgtcgtcgtc     180
cttgtagtct gacct                                                      195
```

<210> SEQ ID NO 81
<211> LENGTH: 63
<212> TYPE: PRT
<213> ORGANISM: Artificial Sequence
<220> FEATURE:
<223> OTHER INFORMATION: synthetic SCL-E47 antagonist encoded by clone
      BGF35 H. influenzae insertion

<400> SEQUENCE: 81

```
Gln Gly Arg Arg Arg Gln Gly Leu Ser Ile Asn Gln Trp Leu Glu Lys
1               5                   10                  15

Tyr Gly Tyr Ile Glu Met Gln Gly Asn Glu Thr Phe Lys Leu Ala Val
                20                  25                  30

Arg Glu Leu Ser Asn Val Val Glu Glu Thr Leu Leu Ala Asn Asn Leu
            35                  40                  45

Asp Lys Lys Asp Leu Asp Trp Leu Val Val Val Val Leu Val Val
        50                  55                  60
```